United States Patent
Lavi et al.

(10) Patent No.: US 12,236,600 B2
(45) Date of Patent: Feb. 25, 2025

(54) VASCULAR CHARACTERISTIC DETERMINATION BASED ON MULTIPLE IMAGES IDENTIFYING A COMMON VASCULAR SEGMENT WITH CORRESPONDENCE MODELING OF A VASCULAR TREE

(71) Applicant: CathWorks Ltd, Kfar-Saba (IL)

(72) Inventors: Guy Lavi, Moshav Mishmeret (IL); Uri Merhav, Rechovot (IL); Ifat Lavi, Moshav Mishmeret (IL)

(73) Assignee: CathWorks, Ltd., Kfar-Saba (IL)

( * ) Notice: Subject to any disclaimer, the term of this patent is extended or adjusted under 35 U.S.C. 154(b) by 0 days.

(21) Appl. No.: 18/482,811

(22) Filed: Oct. 6, 2023

(65) Prior Publication Data
US 2024/0153087 A1    May 9, 2024

Related U.S. Application Data

(63) Continuation of application No. 17/493,518, filed on Oct. 4, 2021, now Pat. No. 11,816,837, which is a
(Continued)

(51) Int. Cl.
*G06T 7/00* (2017.01)
*A61B 5/02* (2006.01)
(Continued)

(52) U.S. Cl.
CPC ........ *G06T 7/0014* (2013.01); *A61B 5/02007* (2013.01); *A61B 6/022* (2013.01);
(Continued)

(58) Field of Classification Search
None
See application file for complete search history.

(56) References Cited

U.S. PATENT DOCUMENTS

| 5,150,292 A | 9/1992 | Hoffmann et al. |
| 5,638,823 A | 6/1997 | Akay et al. |
| | (Continued) | |

FOREIGN PATENT DOCUMENTS

| AU | 2010298333 | 1/2012 |
| CN | 104282009 | 1/2015 |
| | (Continued) | |

OTHER PUBLICATIONS

Abraham et al., "Alternative routes in road networks", ACM Journal of Experimental Algorithmics, Association of Computing Machinery, vol. 18(1):1.3:2-1.3:17 (2013).
(Continued)

*Primary Examiner* — Tahmina N Ansari
(74) *Attorney, Agent, or Firm* — Knobbe, Martens, Olson, & Bear, LLP

(57) ABSTRACT

Automated image analysis used in vascular state modeling. Coronary vasculature in particular is modeled in some embodiments. Methods of "virtual revascularization" of a presently stenotic vasculature are described; useful, for example, as a reference in disease state determinations. Structure and uses of a model which relates records comprising acquired images or other structured data to a vascular tree representation are described.

20 Claims, 29 Drawing Sheets

Related U.S. Application Data continuation of application No. 16/578,839, filed on Sep. 23, 2019, now Pat. No. 11,138,733, which is a continuation of application No. 15/031,815, filed as application No. PCT/IL2014/050923 on Oct. 23, 2014, now Pat. No. 10,424,063, which is a continuation-in-part of application No. PCT/IL2014/050044, filed on Jan. 15, 2014, and a continuation-in-part of application No. PCT/IL2014/050039, filed on Jan. 15, 2014, and a continuation-in-part of application No. PCT/IL2014/050043, filed on Jan. 15, 2014, and a continuation-in-part of application No. PCT/IL2013/050869, filed on Oct. 24, 2013.

(60) Provisional application No. 61/986,218, filed on Apr. 30, 2014.

(51) Int. Cl.

| | | |
|---|---|---|
| *A61B 6/00* | (2006.01) | |
| *A61B 6/02* | (2006.01) | |
| *A61B 6/46* | (2024.01) | |
| *A61B 6/50* | (2024.01) | |
| *A61B 8/00* | (2006.01) | |
| *G06T 11/00* | (2006.01) | |
| *G16H 50/30* | (2018.01) | |
| *G16H 50/50* | (2018.01) | |
| *A61B 6/03* | (2006.01) | |
| *A61B 8/06* | (2006.01) | |
| *A61B 8/08* | (2006.01) | |
| *A61B 8/12* | (2006.01) | |
| *A61B 34/10* | (2016.01) | |

(52) U.S. Cl.
CPC .............. *A61B 6/466* (2013.01); *A61B 6/503* (2013.01); *A61B 6/504* (2013.01); *A61B 6/507* (2013.01); *A61B 6/5217* (2013.01); *A61B 8/5223* (2013.01); *G06T 11/006* (2013.01); *G16H 50/30* (2018.01); *G16H 50/50* (2018.01); *A61B 6/032* (2013.01); *A61B 6/037* (2013.01); *A61B 8/06* (2013.01); *A61B 8/0883* (2013.01); *A61B 8/12* (2013.01); *A61B 2034/104* (2016.02); *A61B 2034/105* (2016.02); *A61B 2034/108* (2016.02); *G06T 2207/10116* (2013.01); *G06T 2207/30104* (2013.01); *G06T 2211/421* (2013.01)

(56) References Cited

U.S. PATENT DOCUMENTS

| | | | |
|---|---|---|---|
| 6,047,080 | A | 4/2000 | Chen et al. |
| 6,186,948 | B1 | 2/2001 | Kamiyama et al. |
| 6,236,878 | B1 | 5/2001 | Taylor et al. |
| 6,842,638 | B1 | 1/2005 | Suri et al. |
| 7,113,623 | B2 | 9/2006 | Chen et al. |
| 7,339,585 | B2 | 3/2008 | Verstraelen et al. |
| 7,369,691 | B2 | 5/2008 | Kondo et al. |
| 7,574,026 | B2 | 8/2009 | Rasche et al. |
| 7,657,299 | B2 | 2/2010 | Huizenga et al. |
| 7,693,315 | B2 | 4/2010 | Krishnan et al. |
| 7,738,626 | B2 | 6/2010 | Weese et al. |
| 7,808,503 | B2 | 10/2010 | Duluk, Jr. et al. |
| 7,864,997 | B2 | 1/2011 | Aben |
| 7,912,260 | B2 | 3/2011 | Breeuwer et al. |
| 7,970,187 | B2 | 6/2011 | Puts et al. |
| 8,073,224 | B2 | 12/2011 | Strobel et al. |
| 8,086,000 | B2 | 12/2011 | Weijers et al. |
| 8,090,164 | B2 | 1/2012 | Bullitt et al. |
| 8,155,411 | B2 | 4/2012 | Hof et al. |
| 8,298,147 | B2 | 10/2012 | Huennekens et al. |
| 8,311,748 | B2 | 11/2012 | Taylor et al. |
| 8,311,750 | B2 | 11/2012 | Taylor |
| 8,315,812 | B2 | 11/2012 | Taylor |
| 8,321,150 | B2 | 11/2012 | Taylor |
| 8,331,314 | B2 | 12/2012 | Quiang et al. |
| 8,496,594 | B2 | 7/2013 | Taylor et al. |
| 8,523,779 | B2 | 9/2013 | Taylor et al. |
| 8,548,778 | B1 | 10/2013 | Hart et al. |
| 8,554,490 | B2 | 10/2013 | Tang et al. |
| 8,560,968 | B1 | 10/2013 | Nair |
| 8,768,669 | B1 | 7/2014 | Hart et al. |
| 8,771,195 | B2 | 7/2014 | Kim et al. |
| 8,787,641 | B2 | 7/2014 | Hof et al. |
| 8,812,246 | B2 * | 8/2014 | Taylor ............... A61B 6/503 382/128 |
| 8,824,752 | B1 | 9/2014 | Fonte et al. |
| 8,861,820 | B2 | 10/2014 | Fonte et al. |
| 8,970,578 | B2 | 3/2015 | Voros et al. |
| 9,008,405 | B2 | 4/2015 | Fonte et al. |
| 9,042,613 | B2 | 5/2015 | Spilker et al. |
| 9,078,564 | B2 | 7/2015 | Taylor |
| 9,129,418 | B2 | 9/2015 | Schormans et al. |
| 9,138,147 | B2 | 9/2015 | Schmitt et al. |
| 9,189,600 | B2 | 11/2015 | Spilker et al. |
| 9,256,936 | B2 | 2/2016 | Jacobs et al. |
| 9,314,584 | B1 | 4/2016 | Riley et al. |
| 9,375,191 | B2 | 6/2016 | Verstraelen et al. |
| 9,406,141 | B2 | 8/2016 | Kelm et al. |
| 9,430,827 | B2 | 8/2016 | Kelm et al. |
| 9,466,117 | B2 | 10/2016 | Habets et al. |
| 9,471,999 | B2 | 10/2016 | Ishii et al. |
| 9,572,495 | B2 | 2/2017 | Schmitt et al. |
| 9,576,360 | B2 | 2/2017 | Schormans et al. |
| 9,615,755 | B2 | 4/2017 | Riley et al. |
| 9,706,925 | B2 | 7/2017 | Taylor |
| 9,743,835 | B2 | 8/2017 | Taylor |
| 9,786,068 | B2 | 10/2017 | Ishii et al. |
| 9,801,689 | B2 | 10/2017 | Taylor |
| 9,805,465 | B2 * | 10/2017 | Kyriakou ............... A61B 6/504 |
| 9,814,433 | B2 | 11/2017 | Benishti et al. |
| 9,858,387 | B2 | 1/2018 | Lavi et al. |
| 9,870,634 | B2 | 1/2018 | Grady et al. |
| 9,940,736 | B2 | 4/2018 | Ishii et al. |
| 9,943,233 | B2 | 4/2018 | Lavi et al. |
| 9,968,256 | B2 | 5/2018 | Taokowsky et al. |
| 9,977,869 | B2 | 5/2018 | Lavi et al. |
| 9,999,361 | B2 | 6/2018 | Sharma et al. |
| 10,141,074 | B2 | 11/2018 | Lavi et al. |
| 10,159,529 | B2 | 12/2018 | Taylor |
| 10,210,956 | B2 | 2/2019 | Lavi et al. |
| 10,219,704 | B2 | 3/2019 | Lavi et al. |
| 10,342,442 | B2 * | 7/2019 | Hattangadi ........ A61B 5/02755 |
| 10,354,744 | B2 | 7/2019 | Sharma et al. |
| 10,373,700 | B2 | 8/2019 | Sharma et al. |
| 10,395,774 | B2 | 8/2019 | Lavi et al. |
| 10,424,063 | B2 | 9/2019 | Lavi et al. |
| 10,456,094 | B2 | 10/2019 | Fonte et al. |
| 10,470,730 | B2 | 11/2019 | Benishti et al. |
| 10,559,388 | B2 | 2/2020 | Lavi et al. |
| 10,595,807 | B2 | 3/2020 | Lavi et al. |
| 10,631,737 | B2 | 4/2020 | Lavi et al. |
| 10,682,180 | B2 * | 6/2020 | Taylor ............... A61B 34/25 |
| 10,702,339 | B2 | 7/2020 | Taylor |
| 10,748,285 | B2 | 8/2020 | Igarashi et al. |
| 11,081,237 | B2 | 8/2021 | Lavi et al. |
| 11,083,524 | B2 | 8/2021 | Taylor |
| 11,087,884 | B2 | 8/2021 | Sankaran et al. |
| 11,090,118 | B2 | 8/2021 | Taylor |
| 11,116,575 | B2 | 9/2021 | Taylor |
| 11,138,733 | B2 | 10/2021 | Lavi et al. |
| 11,185,368 | B2 | 11/2021 | Spilker et al. |
| 11,202,612 | B2 | 12/2021 | Sakaguchi |
| 11,272,845 | B2 | 3/2022 | Cheline et al. |
| 11,278,208 | B2 | 3/2022 | Lavi et al. |
| 11,295,864 | B2 | 4/2022 | Benishti et al. |
| 11,298,187 | B2 | 4/2022 | Taylor |
| 11,304,665 | B2 | 4/2022 | Sharma et al. |
| 11,382,569 | B2 | 7/2022 | Grady et al. |
| 11,406,337 | B2 | 8/2022 | Lavi et al. |

(56) References Cited

U.S. PATENT DOCUMENTS

| | | | |
|---|---|---|---|
| 11,423,532 B2 | 8/2022 | Takahashi et al. | |
| 11,538,161 B2 | 12/2022 | Wang et al. | |
| 11,557,069 B2 | 1/2023 | Senzig et al. | |
| 11,564,746 B2 | 1/2023 | Spilker et al. | |
| 11,576,626 B2 | 2/2023 | Fonte et al. | |
| 11,583,340 B2 | 2/2023 | Taylor | |
| 11,615,894 B2 | 3/2023 | Lavi et al. | |
| 11,666,236 B2 | 6/2023 | Lavi et al. | |
| 11,707,196 B2 | 7/2023 | Lavi et al. | |
| 11,728,037 B2 | 8/2023 | Lavi et al. | |
| 11,793,575 B2 | 10/2023 | Taylor | |
| 11,810,661 B2 | 11/2023 | Barley et al. | |
| 11,816,837 B2 | 11/2023 | Lavi et al. | |
| 11,826,106 B2 | 11/2023 | Hart et al. | |
| 12,016,635 B2 | 6/2024 | Taylor | |
| 2003/0105401 A1 | 6/2003 | Jago et al. | |
| 2004/0019264 A1 | 1/2004 | Suurmond et al. | |
| 2004/0066958 A1 | 4/2004 | Chen et al. | |
| 2005/0041842 A1 | 2/2005 | Frakes et al. | |
| 2005/0043614 A1 | 2/2005 | Huizenga et al. | |
| 2005/0249327 A1 | 11/2005 | Wink et al. | |
| 2005/0272992 A1 | 12/2005 | O'Donnell et al. | |
| 2006/0036167 A1 | 2/2006 | Shina | |
| 2006/0074285 A1 | 4/2006 | Zarkh et al. | |
| 2006/0084862 A1 | 4/2006 | Suurmond et al. | |
| 2007/0031019 A1 | 2/2007 | Lesage et al. | |
| 2007/0167833 A1 | 7/2007 | Redel et al. | |
| 2008/0020362 A1 | 1/2008 | Cotin et al. | |
| 2008/0187199 A1 | 8/2008 | Gulsun et al. | |
| 2008/0205722 A1* | 8/2008 | Schaefer | G06T 7/11 382/128 |
| 2009/0016483 A1 | 1/2009 | Kawasaki et al. | |
| 2009/0171321 A1 | 7/2009 | Callaghan | |
| 2009/0299640 A1 | 12/2009 | Ellis et al. | |
| 2009/0312648 A1 | 12/2009 | Zhang et al. | |
| 2010/0010428 A1 | 1/2010 | Yu et al. | |
| 2010/0017171 A1 | 1/2010 | Spilker et al. | |
| 2010/0021025 A1 | 1/2010 | Hof et al. | |
| 2010/0067760 A1 | 3/2010 | Zhang et al. | |
| 2010/0125197 A1 | 5/2010 | Fishel | |
| 2010/0160764 A1 | 6/2010 | Steinberg et al. | |
| 2010/0220917 A1 | 9/2010 | Steinberg et al. | |
| 2010/0296709 A1 | 11/2010 | Ostrovsky-Berman et al. | |
| 2010/0298719 A1 | 11/2010 | Thrysoe et al. | |
| 2011/0015530 A1 | 1/2011 | Misawa | |
| 2011/0096907 A1 | 4/2011 | Mohamed | |
| 2011/0134433 A1* | 6/2011 | Yamada | A61B 5/0073 359/344 |
| 2011/0135175 A1 | 6/2011 | Ostrovsky-Berman et al. | |
| 2011/0142313 A1* | 6/2011 | Pack | G06T 7/246 378/4 |
| 2011/0182492 A1 | 7/2011 | Grass et al. | |
| 2012/0014574 A1 | 1/2012 | Ferschel et al. | |
| 2012/0041318 A1 | 2/2012 | Taylor | |
| 2012/0041739 A1 | 2/2012 | Taylor | |
| 2012/0053918 A1 | 3/2012 | Taylor | |
| 2012/0053919 A1 | 3/2012 | Taylor | |
| 2012/0053921 A1 | 3/2012 | Taylor | |
| 2012/0059246 A1 | 3/2012 | Taylor | |
| 2012/0059249 A1 | 3/2012 | Verard et al. | |
| 2012/0062841 A1 | 3/2012 | Stetson et al. | |
| 2012/0072190 A1 | 3/2012 | Sharma et al. | |
| 2012/0075284 A1 | 3/2012 | Rivers et al. | |
| 2012/0150048 A1 | 6/2012 | Kang et al. | |
| 2012/0177275 A1 | 7/2012 | Suri | |
| 2012/0230565 A1 | 9/2012 | Steinberg et al. | |
| 2012/0236032 A1 | 9/2012 | Arvidsson | |
| 2012/0243761 A1 | 9/2012 | Senzig et al. | |
| 2013/0060133 A1 | 3/2013 | Kassab et al. | |
| 2013/0094745 A1 | 4/2013 | Sundar | |
| 2013/0158476 A1 | 6/2013 | Olson | |
| 2013/0226003 A1* | 8/2013 | Edic | A61B 6/507 600/504 |
| 2013/0229621 A1 | 9/2013 | Stetson et al. | |
| 2013/0324842 A1 | 12/2013 | Mittal et al. | |
| 2014/0005535 A1 | 1/2014 | Edic et al. | |
| 2014/0046642 A1 | 2/2014 | Hart et al. | |
| 2014/0086461 A1 | 3/2014 | Yao et al. | |
| 2014/0094693 A1 | 4/2014 | Cohen et al. | |
| 2014/0100451 A1 | 4/2014 | Tolkowsky et al. | |
| 2014/0121513 A1 | 5/2014 | Tolkowsky et al. | |
| 2014/0142398 A1 | 5/2014 | Patil et al. | |
| 2014/0200867 A1 | 7/2014 | Lavi et al. | |
| 2014/0249790 A1 | 9/2014 | Spilker et al. | |
| 2014/0303495 A1 | 10/2014 | Fonte et al. | |
| 2014/0371578 A1 | 12/2014 | Auvray et al. | |
| 2015/0201897 A1 | 7/2015 | Kyriakou | |
| 2015/0213600 A1* | 7/2015 | Kyriakou | G06T 7/0012 345/424 |
| 2015/0265162 A1 | 9/2015 | Lavi et al. | |
| 2015/0335304 A1* | 11/2015 | Lavi | G16H 50/30 600/407 |
| 2015/0339847 A1* | 11/2015 | Benishti | A61B 5/026 382/131 |
| 2015/0342551 A1* | 12/2015 | Lavi | G16H 50/50 600/407 |
| 2016/0007945 A1 | 1/2016 | Taylor | |
| 2016/0073928 A1 | 3/2016 | Soper et al. | |
| 2016/0110866 A1 | 4/2016 | Taylor | |
| 2016/0110867 A1 | 4/2016 | Taylor | |
| 2016/0128661 A1 | 5/2016 | Taylor | |
| 2016/0247279 A1* | 8/2016 | Lavi | A61B 6/466 |
| 2018/0182096 A1* | 6/2018 | Grady | G06T 7/0012 |
| 2018/0268941 A1 | 9/2018 | Lavi et al. | |
| 2018/0344174 A9 | 12/2018 | Schmitt et al. | |
| 2020/0126229 A1* | 4/2020 | Lavi | G06T 7/0014 |
| 2020/0349708 A1 | 11/2020 | Igarashi et al. | |
| 2021/0244475 A1 | 8/2021 | Taylor | |
| 2021/0267690 A1 | 9/2021 | Taylor | |
| 2021/0272030 A1 | 9/2021 | Sankaran et al. | |
| 2021/0282860 A1 | 9/2021 | Taylor | |
| 2021/0358634 A1 | 11/2021 | Sankaran et al. | |
| 2021/0375474 A1 | 12/2021 | Lavi et al. | |
| 2022/0028080 A1 | 1/2022 | Lavi et al. | |
| 2022/0079563 A1 | 3/2022 | Kemp | |
| 2022/0087544 A1 | 3/2022 | Schmitt et al. | |
| 2022/0110687 A1 | 4/2022 | Spilker et al. | |
| 2022/0211280 A1 | 7/2022 | Lavi et al. | |
| 2022/0230312 A1 | 7/2022 | Choi et al. | |
| 2022/0233081 A1 | 7/2022 | Cheline et al. | |
| 2022/0277447 A1 | 9/2022 | Wang et al. | |
| 2022/0285034 A1 | 9/2022 | Lavi et al. | |
| 2023/0084748 A1 | 3/2023 | Lavi et al. | |
| 2023/0148977 A1 | 5/2023 | Fonte et al. | |
| 2023/0282365 A1 | 9/2023 | Lavi et al. | |
| 2023/0298176 A1 | 9/2023 | Choi et al. | |
| 2023/0352152 A1 | 11/2023 | Grady et al. | |
| 2024/0050159 A1 | 2/2024 | Hart et al. | |
| 2024/0099589 A1 | 3/2024 | Lavi et al. | |
| 2024/0130796 A1 | 4/2024 | Song et al. | |

FOREIGN PATENT DOCUMENTS

| | | |
|---|---|---|
| EP | 1396274 | 3/2004 |
| EP | 2163272 | 3/2010 |
| EP | 2633815 A1 | 9/2013 |
| EP | 2779907 | 9/2014 |
| EP | 2873371 | 5/2015 |
| EP | 2633815 B1 | 6/2017 |
| EP | 3363350 | 8/2018 |
| EP | 3460688 | 3/2019 |
| EP | 2776960 | 9/2021 |
| EP | 3534372 | 9/2021 |
| EP | 3282380 | 11/2021 |
| EP | 3282381 | 11/2021 |
| EP | 3903672 | 11/2021 |
| EP | 3664026 | 2/2022 |
| EP | 3076854 | 4/2022 |
| EP | 3979259 | 4/2022 |
| EP | 3258446 | 5/2022 |
| EP | 3298959 | 9/2022 |
| JP | H08-131429 | 5/1996 |
| JP | 2003-508152 | 3/2003 |

(56) References Cited

FOREIGN PATENT DOCUMENTS

| | | |
|---|---|---|
| JP | 2003-514600 | 4/2003 |
| JP | 2004-243117 | 9/2004 |
| JP | 2007-502644 | 2/2007 |
| JP | 2007-325920 | 12/2007 |
| JP | 4177217 B2 | 11/2008 |
| JP | 2010-042247 | 2/2010 |
| JP | 2011-212314 | 10/2011 |
| JP | 2013-090799 | 5/2013 |
| JP | 2010-505493 | 7/2013 |
| JP | 2013-534154 | 9/2013 |
| JP | 2014-064915 | 4/2014 |
| JP | 2015-527901 | 9/2015 |
| NL | 2012324 | 8/2015 |
| WO | WO 2001/21057 | 3/2001 |
| WO | WO 2007/066249 | 6/2007 |
| WO | WO 2010/033971 | 3/2010 |
| WO | WO 2011/038044 | 3/2011 |
| WO | WO 2011/039685 | 4/2011 |
| WO | WO 2012/021037 | 2/2012 |
| WO | WO 2012/021307 | 2/2012 |
| WO | WO 2012/173697 | 12/2012 |
| WO | WO 2013/102880 | 7/2013 |
| WO | WO 2014/027692 | 2/2014 |
| WO | WO 2014/064702 | 5/2014 |
| WO | WO 2014/111927 | 7/2014 |
| WO | WO 2014/111929 | 7/2014 |
| WO | WO 2014/111930 | 7/2014 |
| WO | WO 2015/059706 | 4/2015 |

OTHER PUBLICATIONS

Andriotis et al., "A new method of three-dimensional coronary artery reconstruction from X-Ray angiography: Validation against a virtual phantom and multislice computed tomography", Catheterization and Cardiovascular Interventions, vol. 71:28-43 (2008).
Barnea, "Model-based estimation of coronary vessel diameter in angiographic images", Proceedings of the 20th Annual International Conference of the IEEE Engineering in Medicine and Biology Society, vol. 20:513-516 (1998).
Barratt et al., "Reconstruction and quantification of the carotid artery bifurcation from 3-D ultrasound images", IEEE Transactions on Medical Imaging, vol. 23(5):567-583 (2004).
Bullitt et al., "Determining malignancy of brain tumors by analysis of vessel shape", Medical Image Computing and Computer-Assisted Intervention, MICCAI 2004 Conference Proceedings, Lecture notes in Computer Science, LNCS, 3217:645-653.
Caiati et al., "New noninvasive method for coronary flow reserve assessment: Contrast-enhanced transthoracic second harmonic echo doppler", Circulation, vol. 99:771-778 (1999).
Caiati et al., "Detection, location, and severity assessment of left anterior descneding coronary artery stenoses by means of contrast-enhanced transthoracic harmonic echo dopper", European Heart Journal, vol. 30:1797-1806 (2009).
Chung, "Image segmentation methods for detecting blood vessels in angiography", 2006 9th International Conference on Control, Automation, Robotics and Vision, Singapore, pp. 1-6 (2006).
Dickie et al., "Live-vessel: interactive vascular image segmentation with simultaneous extraction of optimal medial and boundary paths", Technical Report TR 2009-23, School of Computing Science, Simon Fraser University, Burnaby, BC, Canada, Nov. 2009.
Frangi et al., "Multiscale vessel and enhancement filtering", Medical Image Computing and Computer-Assisted Intervention, MICCA '98 Lecture Notes in Computer Science, vol. 1496:130-137 (1998).
Fraz, "Blood vessel segmentation methodologies, in retinal images—a survey", Computer Methods and Programs in Biomedicine, vol. 108:407-433 (2012).
Fusejima, "Noninvasive measurement of coronary artery blood flow using combined two-dimensional and doppler echocardiography", JACC vol. 10(5):1024-1031 (1987).
Hawkes et al., "Validation of volume blood flow measurements using three-dimensional distance-concentration functions detived from digital X-Ray angiograms", Investigative Radiology, vol. 29(4):434-442 (1994).
Hoffmann et al., "Determination of instantaneous and average blood flow rates from digital angiograms of vessel phantoms using distance-density curves", Investigative Radiology, vol. 26(3):207-212 (1991).
Holdsworth et al., "Quantitative angiographic blood-flow measurement using pulsed intra-arterial injection", Medical Physics, vol. 26(10):2168-2175 (1999).
Huo et al., "Intraspecific scaling laws of vascular trees", J.R. Soc. Interface vol. 9:190-200 (2012).
Janssen et al., "New approaches for the assessment of vessel sizes in quantitative (cardio-)vascular X-ray analysis", Int J Cardiovasc Imaging vol. 26:259-271 (2010).
Jiang et al., "Vascular tree reconstruction by minimizing a physiological functional cost", 2010 IEEE Computer Society Conference on Computer Vision and Pattern Recognition—workshops, San Francisco, CA, pp. 178-185, doi: 10.1109/CVPRW.2010.5543593.
Kappetein et al, "Current percutaneous coronary intervention and coronary artery bypass grafting practices for three-vessel and left main coronary artery disease: Insights from the Syntax run-in phase", European Journal of Cardio-Thoracic Surgery, vol. 29:486-491 (2010).
Kass et al., "Snakes: active contour models", Int. J. Comput. Vis. vol. 1:321-331 (1987).
Kirkeeide, "Coronary obstructions, morphology and physiologic significance", Quantitative Coronary Arteriography, Chap. 11:229-244 (1991).
Lethen et al., "Validation of noninvasive assessment of coronary flow velocity reserve in the right coronary artery—A comparison of transthoracic echocardiographic results with intracoronary doppler flow wire measurements", European Heart Journal, vol. 24:1567-1575 (2003).
Li et al, "Minimization of region-scalable fitting energy for image segmentation", in IEEE Transactions on Image Processing, vol. 17(10):1940-1949 (2008).
Meimoun et al., "Non-invasive assessment of coronary flow and coronary flow reserve by transthoracic doppler echocardiography: a magic tool for the real world", European Journal of Echocardiography, vol. 9:449-457 (2008).
Mercer-Rosa et al., "Illustration of the additional value of real-time 3-dimensional echocardiography to conventional transthoracic and transesophageal 2-dimensional echocardiography in imaging muscular ventricular septal defects: does this have any impact on individual patient treatment", Journal of the American Society of Echocardiography, vol. 19(12):1511-1519 (2006).
Molloi et al., "Quantification of fractional flow reserve using angiographic image data", World Congress on Medical Physics and Biomedical Engineering, Munich, Germany, Sep. 7-12, 2009.
Molloi et al., "Estimation of coronary artery hyperemic blood flow based on arterial lumen volume using angiographic images", Int J Cardiovasc Imaging, vol. 28:1-11 (2012).
Ng et al., "Novel QCA methodologies and angiographic scores", Int J Cardiovasc Imaging vol. 27:157-165 (2011).
Pellot et al., "A 3D reconstruction of vascular structures from two X-Ray angiograms using an adapted simulated annealing algorithm", IEEE Transactions of Medical Imaging, vol. 13(1):48-60 (1994).
Pinho et al., "Assessment and stenting of tracheal stenosis using deformable shape models", Medical Image Analysis, vol. 15(2):250-266 (2010).
Polytimi et al., "Close to transplant renal artery stenosis and percutaneous transluminal treatment", Journal of Transplantation, vol. 2011, 7 pages (2011).
Sarwal et al., "3-D reconstruction of coronary arteries", Proceedings of the 16th Annual Intl. Conference of the IEEE Engineering in Medicine and Biology Society, Engineering Advances: New Opportunities for Biomedical Engineers, Nov. 3, 1994, pp. 504-505.
Sato et al., "A viewpoint determination system for stenosis diagnosis and quantification in coronary angiogrphic image acquisition", IEEE Transactions on Medical Imaging, vol. 17(1):121-137 (1998).

(56) References Cited

OTHER PUBLICATIONS

Seifalian et al., "A new algorithm for deriving pulsatile blood flow waveforms tested using simulated dynamic angiographic data", Neuroradiology, vol. 31:263-269 (1989).
Seifalian et al., "Blood flow measurements using 3D distance-concentration functions derived from digital x-ray angiograms", Cardiovascular Imaging, Chap. 33:425-442 (1996).
Seifalian et al., "Validation of a quantitative radiographic technique to estimate pulsatile blood flow waveforms using digital subtraction angiographic data", Journal of Biomedical Engineering, vol. 13(3):225-233 (1991).
Shang et al., "Vascular active contour for vessel tree segmentation", in IEEE Transactions on Biomedical Engineering, vol. 58(4):1023-1032 (2011).
Shpilfoygel et al., "Comparison of methods for instantaneous angiographic blood flow measurement", Medical Physics, vol. 26(6):862-871 (1999).
Sianos et al., "The Syntax score: an angiographic tool grading the complexity of coronary artery disease", Euro Intervention, vol. 1(2):219-227 (2005).
Siogkas et al., "Quantification of the effect of percutaneous coronary angioplasty on a stenosed right coronary artery", 2010 10th IEEE Intl. Conference on Information Technology and Applications in Biomedicine, Nov. 3-5, 210, pp. 1-4 (2010).
Slomka et al., "Fully automated wall motion and thickening scoring system for myocardial perfusion Spect: Method development and validation in large population", Journal of Nuclear Cardiology, vol. 19(2):291-302 (2012).
Sprague et al., "Coronary x-ray angiographic reconstruction and image orientation", Medical Physics, vol. 33(3):707-718 (2006).
Sun et al., "Coronary CT angiography: current status and continuing challenges", The British Journal of Radiology, vol. 85:495-510 (2012).
Takarada et al., "An angiographic technique for coronary fractional flow reserve measurement: in vivo validation", International Journal of Cardiovascular Imaging, published online pp. 1-10, Aug. 31, 2012.
Termeer et al., "Visualization of myocardial perfusion derived from coronary anatomy", IEEE Transactions on Visualization and Computer Graphics, vol. 14(6):1595-1602 (2008).
Tomasello et al., "Quantitative coronary angiography in the interventional cardiology", Advances in the Diagnosis of Coronary Atherosclerosis, Chap. 14:255-272 (2011).
Tu et al., Assessment of obstruction length and optimal viewing angle from biplane X-ray angiograms, Int J Cardiovasc Imaging, vol. 26:5-17 (2010).
Tu et al., "In vivo assessment of optimal viewing angles from X-ray coronary angiography", EuroIntervention, vol. 7:112-120 (2011).
Tu et al., "In vivo assessment of bifurcation optimal viewing angles and bifurcation angles by three-dimentional (3D) quantitative coronary angiography", Int J Cardiovasc Imaging, published online Dec. 15, 2011, in 9 pages.
Tu et al., "The impact of acquisition angle differences on three-dimensional quantitative coronary angiography", Catheterization and Cardiovascular Interventions, vol. 78:214-222 (2011).
Tuinenburg et al., "Dedicated bifurcation analysis: basic principles", Int J Cardiovasc Imaging, vol. 27:167-174 (2001).
Voci et al., "Coronary flow: a new asset for the echo lab?", European Heart Journal, vol. 25:1867-1879 (2004).
Weickert et al., "A scheme for coherence-enhancing diffusion filtering with optimized rotation invariance", Computer Vision, Graphics, and Pattern Recognition Group, Technical Report, Computer Science Series, pp. 1-20 (2000).
Weickert, "Anisotropic diffusion in image processing", ECMI, published by Teubner Stuttgart, Germany, 181 pages (2008).
Weickert et al., "A scheme for coherence-enhancing diffusion filtering with optimized rotation invariance", Journal of Visual Communication and Image Representation, vol. 13(1-2):103-118 (2002).
Wong et al., "Quantification of fractional flow reserve based on angiographic image data", The International Journal of Cardiac Imaging, vol. 28(1):13-22 (2012).
Wong et al., "Determination of fractional flow reserve (FFR) based on scaling laws: a simulation study", Physics in Medicine and Biology, vol. 53:3995-4011 (2008).
Wong et al., "Automated technique for angiographic determination of coronary blood flow and lumen volume", Acad. Radiol. vol. 13:186-194 (2006).
Xu et al., "Snakes, shapes, and gradient vector flow", IEEE Transactions on Image Processing, vol. 7:359-369 (1998).
Yang et al., "Novel approach for 3-D reconstruction of coronary arteries from two uncalibrated angiographic images", IEEE Transactions on Image Processing, vol. 18(7):1563-1572 (2009).
Youssef et al., "Role of computed tomography coronary angiography in the detection of vulnerable plaque, where does it stand among others?", Angiology, vol. 1(2):1000111-1-1000111-8 (2013).
Zhang et al., "Quantification of coronary microvascular resistance using angiographic images for volumetric blood flow measurement: in vivo validation", Am J Physio Heart Circ vol. 300(6):H2096-H2104 (2011).
Invitation to Pay Additional Fees in Application No. PCT/IB2023/051186, mailed on May 25, 2023, in 33 pages.
Office Action in European Application No. 1959185, dated Jul. 15, 2022.
International Search Report and Written Opinion in application No. PCT/IB20/52879, mailed on Sep. 3, 2020, in 9 pages.
International Preliminary Report on Patentability and Written Opinion in application No. PCT/IB20/52879, dated Jul. 3, 2020, in 6 pages.
Invitation to Pay Additional Fees in Application No. PCT/IL2013/050869, mailed on Jan. 30, 2014, in 6 pages.
Supplementary European Search Report in application No. EP 17798881.3, dated Oct. 15, 2019, in 8 pages.
European Search Report in application No. EP 14708097.2, dated Aug. 3, 2017, in 7 pages.
European Search Report in application No. EP 14710059.8, dated Aug. 1, 2017, in 7 pages.
Supplementary European Search Report in application No. EP 17798882.1, dated Aug. 6, 2020, in 15 pages.
Invitation to Pay Additional Fees in Application No. PCT/IL2014/050923, mailed on Feb. 6, 2015, in 8 pages.
International Search Report and Written Opinion in application No. PCT/IL2014/050923, mailed on Jul. 10, 2015, in 17 pages.
International Preliminary Report on Patentability and Written Opinion in application No. PCT/IL2014/050923, mailed on May 6, 2016.
International Preliminary Report on Patentability and Written Opinion in application No. PCT/IL2013/050869, mailed on May 7, 2015.
International Search Report and Written Opinion in application No. PCT/IL2013/050869, dated May 23, 2014.
International Search Report and Written Opinion in application No. PCT/IL2014/050043, dated May 16, 2014.
International Preliminary Report on Patentability in application No. PCT/IL2014/050043, dated Jul. 30, 2015.
International Search Report and Written Opinion in application No. PCT/IL2014/050044, dated May 16, 2014.
International Preliminary Report on Patentability in application No. PCT/IL2014/050044, dated Jul. 30, 2015.
International Search Report and Written Opinion in application No. PCT/IL2014/050039, dated May 28, 2014.
International Preliminary Report on Patentability in application No. PCT/IL2014/050039, dated Jul. 30, 2015.
Barrett et al., "Interactive live-wire 1-3 boundary extraction", Medical Image Analysis, Oxford University Press, vol. 1(4):331-341 (1997).
Chen et al., "3-D reconstruction of coronary arterial tree to optimize angiographic visualization", IEEE Transactions on Medical Imaging, vol. 19(4):318-336 (2000).
Marchenko, et al., "Vascular editor: from angiographic images to 3D vascular models", Journal of Digital Imaging, vol. 23:386-398 (2010).
Pijls et al., "Experimental basis of determining maximum coronary, myocardial, and collateral blood flow by pressure measurements for

(56) References Cited

OTHER PUBLICATIONS assessing functional stenosis severity before and after percutaneous transluminal coronary angioplasty", Circulation, vol. 87:1354-1367 (1993).

Wang et al., "Optimal viewing angle determination for multiple vessel segments in coronary angiographic image", IEEE Transactions on Nuclear Science, vol. 61(3):1290-1303 (2014).

Wang et al., "Global optimization angiographic viewing angles for coronary arteries with multiple segments", 35th Annual International Conference of the IEEE EMBS, pp. 2640-2643, Osaka, Japan, Jul. 3-7, 2013.

European Search Report in application No. 20162040.8, dated Dec. 14, 2023, in 6 pages.

Office Action with English translation in Japanese application No. 2022-124490, dated Feb. 27, 2024, in 18 pages.

Communication in European application No. 20190353.1, dated Apr. 3, 2024, in 5 pages.

\* cited by examiner

Do "A" or "B" to improve "X"?

If "A" is done, how much will "X" improve?

How should "A" be done, to improve "X"?

Was "A" done as planned?

Did doing "A" improve "X" as expected?

When is doing "A" to improve "X" likely to be needed?

VASCULAR CHARACTERISTIC DETERMINATION BASED ON MULTIPLE IMAGES IDENTIFYING A COMMON VASCULAR SEGMENT WITH CORRESPONDENCE MODELING OF A VASCULAR TREE

PRIORITY CLAIM

This application claims priority to and the benefit as a continuation of U.S. patent application Ser. No. 17/493,518, filed on Oct. 4, 2021, which is a continuation of U.S. patent application Ser. No. 16/578,839, filed on Sep. 23, 2019, which is a continuation of U.S. patent application Ser. No. 15/031,815, filed on Apr. 25, 2016, now U.S. Pat. No. 10,424,063, which is a National Phase of PCT Patent Application No. PCT/IL2014/050923, having an international filing date of Oct. 23, 2014, which is a Continuation-in-Part (CIP) of International Patent Application No. PCT/IL2013/050869 filed on Oct. 24, 2013 and International Patent Application Nos. PCT/IL2014/050043 filed on Jan. 15, 2014, PCT/IL2014/050044 filed on Jan. 15, 2014, and PCT/IL2014/050039 filed on Jan. 15, 2014. International Patent Application No. PCT/IL2014/050923 also claims the benefit of and priority to U.S. Provisional Patent Application No. 61/986,218 filed on Apr. 30, 2014. The contents of the above applications are all incorporated by reference as if fully set forth herein in their entirety.

FIELD AND BACKGROUND

The present invention, in some embodiments thereof, relates to vascular modeling, and, more particularly, but not exclusively, to methods and systems for producing a vascular model which relates vascular portion data according to homologies determined at from feature-level (for example, vascular segment) to sample-level (for example, segment offset) scale, according a level of detail needed to relate data for calculating vascular parameters.

Arterial stenosis is one of the most serious forms of arterial disease. In clinical practice, stenosis severity is estimated by using either simple geometrical parameters, such as determining the percent diameter of a stenosis, or by measuring hemodynamically based parameters, such as the pressure-based myocardial Fractional Flow Reserve (FFR). FFR is an invasive measurement of the functional significance of coronary stenoses. The FFR measurement represents the ratio between the maximal blood flow in the area of stenosis and the maximal blood flow in the same territory without stenosis. Earlier studies showed that FFR <0.75 is an accurate predictor of ischemia and deferral of percutaneous coronary intervention for lesions with FFR ≥0.75 appeared to be safe.

Modeling vascular flow to assess vascular flow is described, for example, in U.S. published patent application number 2012/0059246 of Taylor, to a "Method And System For Patient-Specific Modeling Of Blood Flow", which describes embodiments which include a system for determining cardiovascular information for a patient. The system may include at least one computer system configured to receive patient-specific data regarding a geometry of at least a portion of an anatomical structure of the patient. The portion of the anatomical structure may include at least a portion of the patient's aorta and at least a portion of a plurality of coronary arteries emanating from the portion of the aorta. The at least one computer system may also be configured to create a three-dimensional model representing the portion of the anatomical structure based on the patient-specific data, create a physics-based model relating to a blood flow characteristic within the portion of the anatomical structure, and determine a fractional flow reserve within the portion of the anatomical structure based on the three-dimensional model and the physics-based model.

Additional background art includes:
U.S. Published Patent Application No. 2012/053918 of Taylor;
U.S. Published Patent Application No. 2012/0072190 of Sharma et al.;
U.S. Published Patent Application No. 2012/0053921 of Taylor;
U.S. Published Patent Application No. 2010/0220917 of Steinberg et al.;
U.S. Published Patent Application No. 2010/0160764 of Steinberg et al.;
U.S. Published Patent Application No. 2012/0072190 of Sharma et al.;
U.S. Published Patent Application No. 2012/0230565 of Steinberg et al.;
U.S. Published Patent Application No. 2012/0150048 of Kang et al.;
U.S. Published Patent Application No. 2013/0226003 of Edie at al.;
U.S. Published Patent Application No. 2013/0060133 of Kassab et al.;
U.S. Published Patent Application No. 2013/0324842 of Mittal et al.;
U.S. Published Patent Application No. 2012/0177275 of Sufi and Jasjit;
U.S. Pat. No. 6,236,878 to Taylor et al.;
U.S. Pat. No. 8,311,750 to Taylor;
U.S. Pat. No. 7,657,299 to Hizenga et al.;
U.S. Pat. No. 8,090,164 to Bullitt et al.;
U.S. Pat. No. 8,554,490 to Tang et al.;
U.S. Pat. No. 7,738,626 to Weese et al.;
U.S. Pat. No. 8,548,778 to Hart et al.;
an article titled: "Determination of fractional flow reserve (FFR) based on scaling laws: a simulation study" by Jerry T. Wong and Sabee Molloi, published in Phys. Med. Biol. 53 (2008) 3995-4011;
an article titled: "A Scheme for Coherence-Enhancing Diffusion Filtering with Optimized Rotation Invariance", by Weickert, published in Journal of Visual Communication and Image Representation; Volume 13, Issues 1-2, March 2002, Pages 103-118 (2002);
a thesis in a book titled "Anisotropic Diffusion in Image Processing", by J. Weickert, published by B. G. Teubner (Stuttgart) in 1998;
an article titled: "Multiscale vessel enhancement filtering", by AF Frangi, W. J. Niessen, K. L. Vincken, M. A. Viergever, published in Medical Image Computing and Computer-Assisted Intervention-MICCA'98;
an article titled: "Determination of fractional flow reserve (FFR) based on scaling laws: a simulation study", by Jerry T Wong and Sabee Molloi, published in Phys. Med. Biol. 53 (2008) 3995-4011;
an article titled: "Quantification of Fractional Flow Reserve Using Angiographic Image Data", by S. Molloi, J. T. Wong, D. A Chalyan, and H. Le, published in 0. Dossel and W. C. Schlegel (Eds.): WC 2009, IFMBE Proceedings 25/11, pp. 901-904, 2009;
an article titled: "Quantification of fractional flow reserve based on angiographic image data", by Jerry T. Wong, Huy Le, William M. Suh, David A Chalyan, Toufan Mehraien, Morton J. Kern, Ghassan S. Kassab, and Sabee Molloi, published in Int J Cardiovasc Imaging (2012) 28:13-22;

an article titled: "An angiographic technique for coronary fractional flow reserve measurement: in vivo validation", by Shigeho Takarada, Zhang Zhang and Sabee Molloi, published online on 31 Aug. 2012 in Int J Cardiovasc Imaging;

an article titled: "A new algorithm for deriving pulsatile blood flow waveforms tested using stimulated dynamic angiographic data", by A M. Seifalian, D. J. Hawkes, A C. Colchester, and K. E. Hobbs, published in Neuroradiology, vol. 31, 263-269, 1989;

an article titled: "Validation of a quantitative radiographic technique to estimate pulsatile blood flow waveforms using digital subtraction angiographic data", by A M. Seifalian, D. J. Hawkes, C. R. Hardingham, A C. Colchester, and J. F. Reidy, published in J. Biomed. Eng., vol. 13, no. 3, pp. 225-233, May 1991;

an article titled: "Validation of volume blood flow measurements using three dimensional distance-concentration functions derived from digital X-ray angiograms", by D. J. Hawkes, A M. Seifalian, A C. Colchester, N. Iqbal, C. R. Hardingham, C. F. Bladin, and K. E. Hobbs, published in Invest. Radiol, vol. 29, no. 4, pp. 434-442, April 1994;

an article titled: "Blood flow measurements using 3D distance-concentration functions derived from digital X-ray angiograms", by A M. Seifalian, D. J. Hawkes, C. Bladin, A C. F. Colchester, and K. E. F. Hobbs, published in Cardiovascular Imaging, J. H. C. Reiber and E. E. van der Wall, Eds. Norwell, MA, The Netherlands: Kluwer Academic, 1996, pp. 425-442;

an article titled: "Determination of instantaneous and average blood flow rates from digital angiograms of vessel phantoms using distance-density curves", by K. R. Hoffmann, K. Doi, and L. E. Fencil, published in Invest. Radiol, vol. 26, no. 3, pp. 207212, March 1991;

an article titled: "Comparison of methods for instantaneous angiographic blood flow measurement", by S. D. Shpilfoygel, R. Jahan, R. A Close, G. R. Duckwiler, and D. J. Valentino, published in Med. Phys., vol. 26, no. 6, pp. 862-871, June 1999;

an article titled: "Quantitative angiographic blood flow measurement using pulsed intra-arterial injection", by D. W. Holdsworth, M. Drangova, and A Fenster, published in Med. Phys., vol. 26, no. 10, pp. 2168-2175, October 1999;

an article titled: "Dedicated bifurcation analysis: basic principles", by Joan C. Tuinenburg, Gerhard Koning, Andrei Rares, Johannes P. Janssen, Alexandra J. Lansky, Johan H. C. Reiber, published in Int J Cardiovasc Imaging (2011) 27:167-174;

an article titled: "Quantitative Coronary Angiography in the Interventional Cardiology", by Salvatore Davide Tomasello, Luca Costanzo and Alfredo Ruggero Galassi, published in Advances in the Diagnosis of Coronary Atherosclerosis;

an article titled: "New approaches for the assessment of vessel sizes m quantitative (cardio-)vascular X-ray analysis", by Johannes P. Janssen, *Andrei* Rares, Joan C. Tuinenburg, Gerhard Koning, Alexandra J. Lansky, Johan H. C. Reiber, published in Int J Cardiovasc Imaging (2010) 26:259-271;

an article titled: "Coronary obstructions, morphology and physiologic significance Quantitative Coronary Arteriography" by Kirkeeide R L. ed. Reiber J H C and Serruys P W, published by The Netherlands: Kluwer, 1991, pp 229-244;

an article titled: "Coronary x-ray angiographic reconstruction and image orientation", by Kevin Sprague, Maria Drangova, Glen Lehmann, Piotr Slomka, David Levin, Benjamin Chow and Robert deKemp, published in Med Phys, 2006 March; 33(3):707-718;

an article titled: "A New Method of Three-dimensional Coronary Artery Reconstruction From X-Ray Angiography: Validation Against a Virtual Phantom and Multislice Computed Tomography", by Adamantios Andriotis, Ali Zifan, Manolis Gavaises, Panos Liatsis, Ioannis Pantos, Andreas Theodorakakos, Efstathios P. Efstathopoulos, and Demosthenes Katritsis, published in Catheter Cardiovasc Interv, 2008, January 1; 71(1): 28-43;

an article titled: "Noninvasive Measurement of Coronary Artery Blood Flow Using Combined Two-Dimensional and Doppler Echocardiography", by Kenji Fusejima, MD, published in JACC Vol. 10, No. 5, November 1987: 1024-31;

an article titled: "New Noninvasive Method for Coronary Flow Reserve Assessment: Contrast-Enhanced Transthoracic Second Harmonic Echo Doppler", by Carlo Caiati, Cristiana Montaldo, Norma Zedda, Alessandro Bina and Sabino Iliceto, published in Circulation, by the American Heart Association, 1999; 99:771-778;

an article titled: "Validation of noninvasive assessment of coronary flow velocity reserve in the right coronary artery-A comparison of transthoracic echocardiographic results with intracoronary Doppler flow wire measurements", by Harald Lethena, Hans P Triesa, Stefan Kerstinga and Heinz Lambertza, published in European Heart Journal (2003) 24, 1567-1575;

an article titled: "Coronary flow: a new asset for the echo lab?" by Paolo Vocia, Francesco Pizzutoa and Francesco Romeob, published in European Heart Journal (2004) 25, 1867-1879;

an abstract titled: "Quantification of the effect of Percutaneous Coronary Angioplasty on a stenosed Right Coronary Artery" by Siogkas et al., published in Information Technology and Applications in Biomedicine (ITAB), 2010 10th IEEE International Conference on;

a review paper titled: "Non-invasive assessment of coronary flow and coronary flow reserve by transthoracic Doppler echocardiography: a magic tool for the real world", by Patrick Meimoun and Christophe Tribouilloy, published in European Journal of Echocardiography (2008) 9, 449-457;

an article titled: "Detection, location, and severity assessment of left anterior descending coronary artery stenoses by means of contrast-enhanced transthoracic harmonic echo Doppler", by Carlo Caiati, Norma Zedda, Mauro Cadeddu, Lijun Chen, Cristiana Montaldo, Sabino Iliceto, Mario Erminio Lepera and Stefano Favale, published in European Heart Journal (2009) 30, 1797-1806;

an abstract titled "Determining malignancy of brain tumors by analysis of vessel shape" by Bullitt et al., published in Medical Image Computing and Computer-Assisted Intervention-MICCAI 2004.

The disclosures of all references mentioned above and throughout the present specification, as well as the disclosures of all references mentioned in those references, are hereby incorporated herein by reference.

SUMMARY OF THE INVENTION

According to an aspect of some embodiments of the present invention, there is provided a method of calculating a fractional flow reserve, comprising: receiving a plurality of 2-D images, each image comprising a plurality of regions each containing a vascular segment image; determining groups of the image regions based on comparison of the image regions, the image regions of each group imaging a vascular segment in common; selecting at least one image region from each of a plurality of the groups, the plurality of groups comprising a group for a stenotic vascular segment, and groups for one or more vascular segments comprising vascular branches in the crown of the stenotic segment; measuring vascular characteristics from the selected image regions; and calculating fractional flow reserve of the stenotic vascular segment, based on the vascular characteristics.

According to some embodiments of the invention, the vascular characteristics comprise vascular width.

According to some embodiments of the invention, the vascular characteristics comprise vascular width as a function of position along the length of a vascular segment.

According to some embodiments of the invention, the vascular characteristics comprise vascular resistance.

According to some embodiments of the invention, the 2-D images are X-ray angiography images.

According to some embodiments of the invention, the selecting comprises determination of the image region of least foreshortening.

According to some embodiments of the invention, comparison of the image regions comprises determining parameters of rays projecting from respective planes at which the image regions were acquired to a radiant imaging source.

According to some embodiments of the invention, comparison of the image regions comprises registration of the image regions.

According to some embodiments of the invention, comparison of the image regions comprises comparison of characteristics of the contained vascular segment images.

According to some embodiments of the invention, the vascular segment image comprises an image of a branch of the cardiac artery.

According to an aspect of some embodiments of the present invention, there is provided a method of identifying vascular segments represented in common by different regions of 2-D projection images of a vasculature, comprising: determining the back-projection parameters of a group of rays from identified vascular segments in each of a plurality of the images; and identifying as commonly-represented in each region the represented vascular segment corresponding to groups of back-projecting rays which most nearly intersect each other; wherein a portion of the nearest intersections are at a distance of at least twice the sampling resolution of the 2-D projection images.

According to some embodiments of the invention, the back-projecting is performed according to imaging configuration parameters describing the conditions of image acquisition.

According to some embodiments of the invention, at least one individual ray in one of the groups of rays comprises the ray of closest approach for more than one ray from another of the groups of rays.

According to some embodiments of the invention, the back-projected rays are back-projected by determining parameters describing the path between an image position in a projection plane, and a position of a radiation source.

According to an aspect of some embodiments of the present invention, there is provided a method of calculating a vascular characteristic from a model of a vasculature, comprising: providing a model including: a plurality of groups of samples, the samples being arranged with respect to one another, wherein each group represents a modeled location in the vasculature; selecting from the model one or more of the vascular location for the calculation of the vascular characteristic; selecting for each selected vascular location at least one of the sample groups associated to the vascular location; and determining automatically the vascular characteristic by calculation based on the selected sample groups.

According to some embodiments of the invention, each of the plurality of sample groups comprises at least a portion of a 2-D image of the vasculature.

According to some embodiments of the invention, each of the plurality of sample groups comprises vascular measurements indexed as a function of distance along a pathway through a blood vessel.

According to some embodiments of the invention, the vascular characteristics comprise estimates of fractional flow reserve.

According to some embodiments of the invention, the vascular characteristics comprise estimates of vascular width.

According to some embodiments of the invention, the vascular width comprises a modeled estimate of an unstenosed vascular width.

According to some embodiments of the invention, the vascular characteristics comprise measurements of vascular tortuosity based on the curvature of a pathway between two or more regions in the 2-D image, the pathway substantially following the course of samples comprised in a vascular segment region.

According to some embodiments of the invention, the vasculature comprises cardiac arterial branches.

According to some embodiments of the invention, the selecting, receiving, and/or determining are automatically performed by a digital computer, based on digital representations of the samples.

According to an aspect of some embodiments of the present invention, there is provided a method of relating additional data samples to a vascular tree representation of a vasculature, comprising: generating a first record of an image region of samples projected from a vasculature, the first record having a plurality of entries, each individually mapped to the vascular tree representation; generating a second record of an image region of samples projected from the vasculature; and updating automatically the first record to reflect differences from it found in the second record, based on 3-D projected epipolar mapping between samples of the first and the second record.

According to some embodiments of the invention, the update of the first record is inserted into the vascular tree representation according to the individual mapping.

According to some embodiments of the invention, the update of the first record is inserted into the vascular tree representation in place of the first record.

According to an aspect of some embodiments of the present invention, there is provided a method of relating segment-associated values calculated based on new image data to a vascular tree representation of a vasculature, comprising: determining that a region of a first digital image and a region of a second digital image record a common segment of a vascular tree representation, the region of the first digital region being already identified as recording a particular segment; calculating a vascular characteristic from the region of the second digital image; and associating the vascular characteristic to the particular segment.

According to some embodiments of the invention, the determining comprises automatic calculation by a digital computer, based on comparison of vascular characteristics derived from each region.

According to some embodiments of the invention, the determining comprises automatic calculation by a digital computer, based on calculation from imaging configuration parameters of the possible positions of the common segment region during acquisition of the digital images.

According to an aspect of some embodiments of the present invention, there is provided a method of calculating and using vascular characteristics calculated from 2-D images of a vascular tree, comprising: associating by comparison to each other portions of the 2-D images comprising images of common segments of the vascular tree; performing calculations to generate the vascular characteristics from different groups of the associated portions; and using the vascular characteristics to estimate a functional parameter of the imaged vascular tree.

According to some embodiments of the invention, the associating, performing, and using is without reference to a 3-D reconstruction of the vascular tree.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system" Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system For example, hardware for performing selected tasks according to embodiments of the invention could be implemented as a chip or a circuit. As software, selected tasks according to embodiments of the invention could be implemented as a plurality of software instructions being executed by a computer using any suitable operating system.

In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
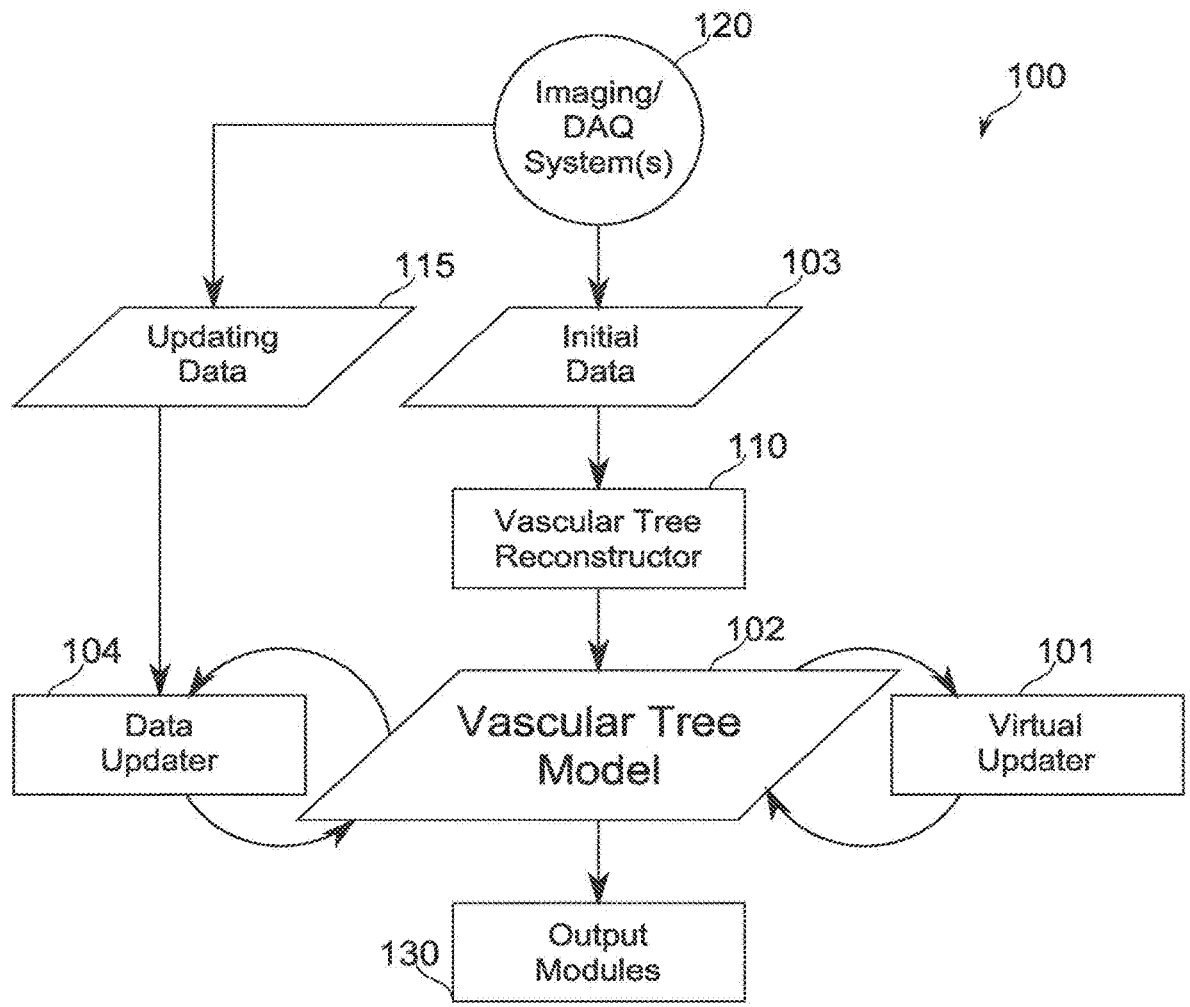
FIG. 1A is a block diagram of a system for production and use of a dynamically updatable vascular tree model, according to some exemplary embodiments of the invention.

The present invention, in some embodiments thereof, relates to vascular modeling, and, more particularly, but not exclusively, to methods and systems for producing a vascular model which relates vascular portion data according to homologies determined at from feature-level (for example, vascular segment) to sample-level (for example, segment offset) scale, according a level of detail needed to relate data for calculating vascular parameters.

Overview

An aspect of some embodiments of the invention relates to associating imaging data, and/or metrics derived from image data, to common regions of the imaged vasculature according to group homologies determined among subsets of the data.

In some embodiments of the invention, a model is structured such that certain high-level vascular tree model-related aspects are loosely coupled, the aspects including, for example: * metric and/or characteristic calculation (for segments, for example); * identity, correspondence and/or homology relationships among separate data groups (for example, images or regions thereof in their various relationships to views/portions of a vascular tree); and/or * overall structure of the vascular tree of interest.

Potentially, this allows freedom for the calculations supporting each such aspect of the model to be structured according to separate criteria, such as, for example, different balances of computational intensiveness and precision.

In some embodiments, for example, it is a potential advantage to calculate vascular metrics from data which is detailed but relatively unstructured (such as original 2-D images), while structuring the relationships among metrics calculated from a vascular tree more loosely than would be required if a reconstruction based on the full image data were required. This stands in potential contrast, for example, to methods which calculate a full 3-D vascular tree, and extract metrics and part relationships (directly or indirectly) from the fully generated tree. It should be understood, however, that the loosely-coupled structure does not preclude generation and/or use of a full or partial 3-D reconstruction.

In some embodiments, high resolution and/or high precision metric calculation tasks are preferably performed on 2-D data point arrays (pixelated images). Potentially, this reduces computational load by reducing a requirement for reconstructive processing to determine the relative 3-D spatial positions of data points, and/or by reducing the number of points for which relationships are determined.

The results, optionally, are globally associated to a vascular tree via (larger and/or sparsely distributed) anatomical structures appearing in-image that can themselves be identified as held in common (homologous) among different images. Optionally, the identification is according to one or more relatively low resolution, low accuracy, and/or low precision (or otherwise rough but computationally inexpensive) techniques.

Thus, a vascular tree model's canonical or overall representation is optionally constructed of relationships among images and/or parts thereof, rather than or m addition to comprising a volumetric representation derived from such images.

Potentially, this even increases accuracy of final results, since resolution-sensitive calculations are optionally carried out on raw or nearly-raw data, rather than on data which has passed through an extensive series of reconstruction steps, not necessarily aimed at optimizing and/or preserving available resolution of representation. This approach recognizes that 3-D mesh or other 3-D volumetric reconstruction, though powerfully general, is not necessarily the optimal starting point for all vascular tree measurements, nor always a necessary intermediate.

In some embodiments, a plurality of image datasets comprising views of a vascular tree of interest are received—for example, 2-D images (which can be projection images, such as produced by imaging of the tissue-transmitted emissions of an angiography X-ray source), which may be of a heart vasculature. From the perspective, in particular, of single-image resolution, there is a potential advantage to using X-ray angiography imaging, but in some embodiments another imaging modality is used such as CAT, MRI, or another imaging modality as known in the art of medical imaging.

In some embodiments, the views are: from different angles, obtained at different times, and/or including only partially mutually overlapping regions of the vascular tree of interest. Optionally—for example, for views obtained at different times—the imaged vascular tree of interest itself changes in shape and/or position. Such changes are, for example, due to heart motion, breathing motion, overall motion of the imaged subject, and/or changes in vascular state. Optionally, changes in vascular state include, for example, changes due to autoregulation, injection of a material affecting vascular function, stenting, and/or disease state (for example, progression between imaging sessions). Optionally, changes in vascular state are actual (for example, seen in original imaging data). Additionally or alternatively, changes in vascular state are modeled: for example, hypothetical progressions, expected results of treatment, and/or variations which model a range of situations to account for possible measurement errors.

In some embodiments of the invention, homology (correspondence) among features seen in the views of the plurality of image datasets is automatically determined at a coarse-grained level. Coarse-grained homology comprises, for example, the characterization of two image regions as representing and/or referencing the same object (such as a vascular segment) in common (though perhaps from different times and/or angles), optionally without additional reference to geometric details of their relationship to each other or the vascular segment represented. In an additional or alternative characteristic of coarse-grained homology, two datasets are treated as homologous as groups—for example, insofar as they refer, as groups of values (such as characteristics, samples, and/or metrics), to the same object-optionally without reference to homologies of parts, such as individual samples or pixels, within each dataset.

"Coarse-grained homology" includes reference to homologies among sparsely distributed features, and/or among features determined by image patterns over an extent of the image much larger than the sampling frequency. A coarse-grained level of homology is, for example, identification of two distinct image regions as imaging the same segment, furcation, stenotic region, vascular wall boundary, and/or other feature. Optionally, homology with respect to landmark features present in an image, but not of direct use for determination of vascular characteristics, are used to assist in the determination of the identities of vascular segments nearby.

However, coarse-grained homology can be established with reference to any general pattern of pixels having dependably identifiable similarities in two or more images. In some embodiments, coarse-grained homology is determined among features considered as patterns of features distributed (and, optionally, spatially separated) over an image plane (optionally, distributed according to a projection from a 3-D space).

In some embodiments, operations which calculate a vascular parameter, such as FFR, are guided in the choice of working data and/or the relationships used among intermediate results, by coarse-grained homologies: for example, to select of image dataset regions as a basis for calculation.

In some embodiments, a single 2-D image region is a sufficient basis for obtaining a metric of vascular anatomy or function (such as width, resistance to flow, and/or volume). Optionally, a plurality of single-region metrics are related to one another, according to their determined homologies (optionally, coarse-grained homologies), for further calculation. For example, segments are determined in some embodiments, to be linked to one another m a particular vascular tree topology. Optionally, measurements of single segment vascular characteristics are selected for further mathematical operations (such as the calculation of vascular resistance in a network of vascular segments) based on the position in the tree topology of the segment from which they were derived.

Additionally or alternatively, in some embodiments, two or more 2-D image regions having determined homology (optionally, coarse-grained homology linking two image regions through commonality in the vascular segment they image) are used for obtaining a metric (quantified characteristic) of vascular anatomy or function which is not purely calculated from single images, but involves combinations of separately acquired images. Uses of common-representation determinations include, without limitation, the following.

Metric combination: in some embodiments, such metrics are used in calculations which require knowledge of the relationships between the features of the source image, and the features of other images. For example, resistance of a single vessel is used as a parameter in calculating resistance of an overall vascular crown, one or more segments of which are themselves measured from another 2-D image.

Metric source selection: in some embodiments, knowledge of the feature homology relationships between a plurality of images is used to determine a list of candidate views, from which a view particularly favorable to a calculation is chosen as a basis for operation.

Metric refinement: in some embodiments, knowledge of feature homology relationships allows measurements of the same region made from different views to be related to one another. For example, measurements are statistically combined, selected from, or otherwise operated on as a homologous set of measurements.

Metric comparison: additionally or alternatively, homologous-region measurements obtained under different conditions are related according to differences among them—for example, to determine conditions before/after a treatment or manipulation, to assess vascular dynamics, and/or for another comparative, normalizing, or differential analysis purpose.

A potential advantage of using coarse-grained homology as a basis for metric combination, source selection, refinement, and/or comparison is that it allows avoiding, simplifying, and/or postponing the determination or re-determination of a "global state" for a vasculature. For example, recalculation of a functional parameter such as FFR (which potentially depends on the different resistances to flow within a multi-segment crown of blood vessels) is simplified, in some embodiments, by bypassing a requirement to regenerate a full 3-D reconstruction after change in a local region of the vasculature. Optionally, even a partial 3-D reconstruction of the changed region itself is avoided; for example, a vascular segment resistance is re-calculated from a single 2-D image region having coarse homology to a region it replaces, augments, combines with, and/or is compared to.

In some embodiments of the invention, coarse-grained homologies are determined by a "brute-force" 3-D reconstruction which relies primarily on predetermined parameters such as position and/or angle of imaging means, radiation sources, and/or image subject. Brute-force 3-D reconstruction comprises, for example, back projection of rays extending from features detected in the respective image planes to their spatial points of closest approach. In some embodiments, brute force 3-D reconstruction even avoids the "reconstruction" itself. For example, if parameters of crossing back-projected ray groups indicate that two images regions were projected from nearly the same region, this is optionally sufficient to establish their homology—even if the 3-D characteristics of region itself remain unresolved.

Without further refinements, such brute force reconstruction, m general, is expected to be insufficiently accurate and/or precise to generate such typical products of 3-D reconstruction as a 3-D mesh and/or vascular wall boundary positions. In some embodiments, brute-force 3-D reconstruction by back-projection of rays allows groups of rays to be identified as extending from homologous image regions, without sufficient precision and/or accuracy to directly allow individual samples to be reliably identified as themselves homologous. For example, the spatial fidelity of the matching of individual rays is larger than 2, 3, 4, and/or 5 sampling intervals of the 2-D image pixels, and/or another larger, smaller, or intermediate fidelity relative to sampling interval. In some embodiments, a matching method defining fidelity is, for example, according to the distance of closest ray approach. In some embodiments, the matching is such that the two rays are exclusively (each for the other) the rays of closest mutual approach.

In particular, 3-D reconstruction using just two images (for example, by back projection of rays) can result in ambiguities and/or inaccuracies for example: where more than one feature occupies a single pixel, where motion occurs between imaging periods, and/or simply due to imprecision in position calibrations.

In some embodiments, brute-force 3-D reconstruction provides sufficient hints to resolve homologies (such as a commonly imaged subject) among features of the source images. For example, bifurcations of blood vessels are distributed relatively sparsely in a vascular image; closest bifurcations in a brute force projection can thus in general be identified as homologous. Optionally, considerations of vascular segment connectivity, fill times (where dye injection time course is imaged), vascular width (which can include stenoses), length, and/or other vascular features are used to resolve ambiguities in the 3-D reconstruction, and/or to find the original homologies themselves.

In some embodiments, homologies are identified directly from 2-D images. For example, 2-D images obtained from slightly varying angles (for example, every 15°, 20°, 30°, or another greater, smaller, or intermediate angular difference) are treated as anisotropic distortions of one another. Homology is optionally assigned at least in part on the basis of "nearest neighbor" locations of salient features, and/or on the basis of correlations among such metrics as vascular length. Optionally, homology is extended through a full range of angular differences by applying such an operation transitively. Vascular length in images changes due to foreshortening effects; in some embodiments, consistency of change moving through three or more images is used in the identification of homology. In some embodiments, homology is constrained, and optionally determined, by analysis of vascular widths, branching patterns, bifurcation angles, and/or filling times.

It should be understood that within the context of a vascular tree, identification of a single region of homology is sometimes sufficient to identify homologies of other regions, and potentially of regions throughout the entire vascular tree of interest. For example, ray back-projection is used in some embodiments to identify a trunk artery (such as the main coronary artery), and all other vascular segments identified based on their branching points relative to the trunk segment. In some embodiments, human-guided selection is used to identify one or more homologies in the dataset, for example, to serve as a starting point, and/or to resolve ambiguities or errors in a machine-generated identification.

An aspect of some embodiments of the invention relates to the calculation of a fractional flow reserve directly from 2-D source data, without intermediate reference to 3-D structural details.

In some embodiments, portions of 2-D images are related to one another according to their common representation of portions of the vascular tree. For example, vascular segments between branch nodes are taken to be the vascular tree portions, and each 2-D image portion that corresponds to a particular such vascular segment is taken to be "homologous" in that sense.

In some embodiments, the establishment of homology is according to direct or indirect linkages made between 2-D data regions. Optionally, the data selected for use in the calculation is the data which most fully reflects the structure of the segment (for example, complete and least foreshortened). Optionally, calculations are performed on two or more visualizations of segments independently, and the results combined and/or selected from afterward.

Fractional flow reserve calculation, m some embodiments, comprises determination of individual vascular segment characteristics such as resistance to flow, and combination of the calculated values to produce an overall flow, according, for example, to the positions of the various vascular segments in the vascular tree (in particular, a stenotic segment, and the segments in the stenotic segment's crown). In some embodiments of the invention, a second state of one or more of the segments (in particular, of the stenotic segment as it is expected to be after an intervention, and/or as it apparently used to be based on characteristics of the lesion it contains) is also calculated, and used in a second determination of overall flow. Optionally, the two flows are compared (for example, as a ratio) to obtain the FFR value, as calculated directly from the 2-D data.

An aspect of some embodiments of the invention relates to the use of a model of vascular structure made of records comprising ordered samples, interrelated through a representation of the vascular tree.

In some embodiments of the invention, the model changes in use, for example, to extrapolate a healthy state, predict a disease progression, guide treatment, and/or assess the effects of treatment.

In some embodiments of the invention, model records comprise spatially and/or temporally structured sample data.

A record is, for example, an image, a data trace, or another unit of structured data acquisition; or data which is analyzed, transformed, and/or synthesized to form a spatial and/or temporal representation.

In some embodiments, the linking data structure is a distributed structure. For example, linking is by associating points relating to a common vascular position a common label. Optionally, the labels are separately associated to a data structure which provides an overall ordering of the labels within a frame of reference comprising the vasculature.

In some embodiments, the sample data of a record is sensed sample data acquired based on probing the physical properties of a vasculature; for example, by use of one or more imaging modalities. In some embodiments, sensed sample data is structured according to the conditions of its original acquisition—for example, as a 3-D image, 2-D image, or 1-D trace or image. Additionally or alternatively, sample data is structured by calibration information describing the conditions of acquisition; for example, the 3-D location of an image plane, and/or a rate of movement of a sampling and/or radiating device through or near the vasculature.

In some embodiments, sets of data samples from different records—but comprising information relating to a common region of the vasculature—are related to one another by superimposed structure. The superimposed structure comprises, for example, region-based tagging, and/or mapping to a common structure. Tagging comprises, in some embodiments, associating data samples with tokens denoting region, or another identifier. Mapping comprises association of data samples with regions of a common structure, for example by tokens, or by one or more rules establishing correspondence between a mapping space and the representational space of a record.

Optionally, a linking data structure is used, based on identified common features of the vasculature and/or surrounding structures. Linking is, for example, by association of samples with indexes into a data structure. In some embodiments, the association is sparse; for example, pixels in an image associated with a vascular centerline are indexed into a representation of the vascular tree centerline, while other pixels are of the image are related to the overall structure of the model as necessary through their arranged relationship to the indexed pixels of the same record.

In some embodiments of the invention, a superimposed and/or common structure comprises a vascular tree skeleton. Optionally, the vascular tree skeleton is represented as a branching set of ordered locations, for example with coordinates defined by segment, node, and or segment displacement coordinates. Additionally or alternatively, the ordered locations comprise 3-D coordinates. In some embodiments, the common structure comprises landmarks, comprising features of the vasculature and/or surrounding tissue used to associate data records containing the same landmarks to the overall model.

In some embodiments, 3-D coordinates are generated in the reconstruction of a vascular tree skeleton. Optionally, they are retained afterward. It should be noted, however, that the actual manipulation of and traversal among records of a relational model potentially is without reference to 3-D coordinates, a common mapping alone being sufficient information to connect samples in different records. For example, a linking-structure vascular tree in some embodiments comprises ordered lists of identifiers associated to segments and branch nodes, optionally without the association of Cartesian 3-D spatial coordinates.

In some embodiments, the vascular model is distinct from a model based on fully 3-D vascular reconstruction, in that not every point of the vasculature is assigned a 3-D representation. For example, a 3-D vascular centerline does not represent vascular wall positions in 3-D. Optionally, wall positions are determined based on 2-D operations on record data. Optionally, when a 3-D wall position is desired (for example, for a display), wall positions in a record are referenced to another position in the record, such as a vascular centerline position which is indexed to a 3-D position.

In some embodiments of the invention, there is no "canonical" representation of a vascular structure (3-D or otherwise), in the sense of a representation of the structure which has a preferred and/or central status in the model hierarchy. This potentially allows choice of representational dimensionality: for a given transformation or display operation, a 1-D, 2-D, or 3-D representation is optionally chosen as an input, based on the representation's convenience or suitability for particular operations on the model.

This is itself a potential advantage for allowing metrics to be calculated based on representations of the vasculature which are substantially copies of the raw sensed data. This contrasts, for example, with calculations based on a fully reconstructed 3-D vascular model, or even on a reduced model derived from a 3-D vascular model, in which assumptions and approximations made during the reconstruction procedure are potentially confused with the original data. Some embodiments of the invention may therefore be considered as "non-destructive" of raw data, while still serving to relate raw data directly or indirectly to a vascular reconstruction, and the organizing benefits it potentially allows.

Another potential advantage of a relational modeling approach is that a record reflecting a modified local portion of the model can co-exist with other records describing the same region. When multiple, potentially conflicting or inconsistent representations of a vascular region are available, the approximations and assumptions needed to choose a "best" representation are made, in some embodiments, at the level of a module performing the calculation. This potentially allows such choices to be tailored to the immediate requirements of the module. For example, calculations on a vascular segment can be performed based on an image where it is shown most clearly (parallel to the plane of imaging and in high contrast, for example), rather than based on an approximation comprising data comprised of multiple source images of potentially variable quality.

An aspect of some embodiments of the invention relates to partial-update modification using calculations on existing data in a model of vascular structure.

In some embodiments of the invention, partial updating of a model comprises modification of an existing structural level of the model, for example, replacement of samples within an array or list of samples with new sample locations or values. In some embodiments, a structure such as an array, list, or other collection of multiple samples itself comprises a "record" or "list record" of the model. Optionally, the record includes and/or is associated with calculations of measurements (metrics) or other characteristics determined based on and/or in relation to the data of the record. Optionally, an existing record is updated partially based on newly calculated, synthesized, and/or imaged data.

In some embodiments, partial updating of a model comprises insertion, removal, and/or replacement of new records into the model, for example, new views of the vasculature in the same or in a different state, based on computed, synthesized, and/or imaged data. In some embodiments of the invention, the data (for example, sample points) of a list record are partially modified, and the modified record added as a new list record to the model, rather than replacing the original list record.

In some embodiments, records in a relational model of a vasculature, are used by an updating module to produce vascular metrics and/or modified versions of the vasculature. In some embodiments, the updating module results are returned as an update to the relational model as a transformed or synthetic record. In some embodiments, the results are used in producing output related to past, present, and/or future vascular state.

A potential advantage of a relational model of vascular structure is a reduction in the computational cost of changes to the model. In embodiments where canonical representation is unimportant, updating is not required to maintain a consistent central representation. Thus, for example, modification of a record comprising an image of the vasculature is optionally performed without propagating the modification to a full 3-D version of the model in order to determine the relevant effects of the modification. Furthermore, refreshes or updates to the model can be based on partial information, for example, images of particular regions of concern, or models of vasculature behavior at only critical points.

It should be understood, nevertheless, that the effects of a local vascular tree modification are readily propagated, in some embodiments, to other records via the superimposed mapping structure. For example, modification of a record comprising a 1-D graph is readily propagated by traversal of mapping relationships to positions on one or more 2-D images. As necessary, effects are even optionally propagated, in some embodiments, to 3-D representations of the vascular tree. Such representations are used, for example, for display and/or more detailed computation of modification effects.

In some embodiments, transformed and/or synthesized sample data of a record is derived based on sensed sample data. In some embodiments, sample data is transformed without change in dimensionality. In some embodiments, an image record is transformed into another image record, for example, by translation, scaling, rotation, and/or anisotropic distortion.

Optionally, the transformation is comprised in a registration with one or more other images sharing some image features. This form of transformation can be useful, for example, for enabling direct 1:1 operations involving two or more images, such as image arithmetic, animated display, or for image import as described hereinbelow.

Optionally, the transformation is comprised in transforming the image to a virtual imaging plane in 3-D space. This form of transformation is useful, for example, in synthetically bringing nearby image planes to a single plane for direct image comparison, and/or as an operation during determination of a common mapping between images.

In some embodiments, a transformation of sample data comprises a change in dimensionality. For example, a 2-D image region comprising a segment of vasculature is analyzed to produce a graph of vascular width (or another parameter) as a function of position along the length of the vascular segment, the graph comprising a new record for the model of vascular structure.

In some embodiments, the sample data of a record is substantially synthesized; for example, constructed and/or manipulated to model a non-existent condition of the vasculature. The condition is, for example, the way a vasculature notionally used to appear ("virtual revascularization" in the case of a stenotic vasculature), the way it is predicted to become (age progression), and/or the way it would appear after medical intervention to open stenotic regions, for example by implantation of a stent.

In some embodiments, a synthesized record is constructed on the basis of one or more other records of the model. For example, anchor regions of a 2-D image record are chosen along a vascular wall region, the anchor regions being selected where they are likely to represent an unstenosed vascular wall state on either side of a potentially stenosed region. Interpolation between the anchor regions, in some embodiments, generates a synthetic wall profile which represents an unstenosed state of the vasculature along this wall. In some embodiments, the synthetic profile is returned to the model and/or propagated into the model as, for example, a 1-D graph of virtual vascular width, a 2-D image within which an image of the vessel lies, or another format related to the mapping frame of reference.

In another example of an embodiment, vascular metrics calculated from images obtained over a plurality of time points separated by, for example, months or years are obtained. Exemplary metrics measured in some embodiments of the invention include vascular width, tortuosity, flow resistivity, elasticity, and/or another measurement of vascular segment anatomy and/or function. In some embodiments, extrapolation of changes in metrics over time is used to synthesize an image or trace record. The record shows, for example, a potential future geometry of the vascular segment.

In yet another embodiment example, images of a vascular segment obtained separated in time by, for example, milliseconds, seconds, minutes, or hours are matched with one another, and compared to extract dynamic differences in vascular width. A record synthesized from this comparison, in some embodiments, comprises an index of vascular elasticity and/or capacity for autoregulation.

An aspect of some embodiments of the invention relates to partial-update modification based on newly acquired data to a multi-representational, relational model of vascular structure.

In some embodiments of the invention, data is made available to be added to a relational vascular model at one or more times after an initial model is constructed. The data is, for example, image data acquired to monitor and/or verify a procedure; or older or newer data which is to be added to the model for a purpose such as review, evaluation, and/or to provide structured documentation. In some embodiments, the data comprise images, and/or other data recorded based on a sensor and/or radiation source carried through the vasculature on a catheter. In some embodiments, data comprises time-varying data, such as heart- or pulse-monitoring data. Optionally monitor data is used to correlate the time of image acquisition to one or more aspects of a patient's physical state; for example, heartbeat phase, respiratory phase, or another state.

It is a potential advantage for a vascular model to be dynamically updatable from newly received data, without a requirement to update a whole representation of the vasculature based on the new data. Two different images which map to a shared region of vasculature, for example, are directly comparable to view changes and/or dynamics of that region, potentially without a requirement for an intermediate 3-D or other unified model representation comprising each image separately. Another aspect of this advantage is that partial image data is potentially sufficient to fulfill a requirement for information, such as verification of the implantation of a stent, while this information is also integrated into an overall representation of the vasculature.

In some embodiments, image data are mapped to the vascular tree (or another mapping and/or tagging scheme) indirectly, for example by registration to image data which has already been mapped, and propagating mapping information therefrom. In some embodiments, image data are mapped directly to a mapping schema; for example, by projecting rays from the image data acquisition plane to intersect with the region of a 3-D representation of a vascular tree, and mapping based on said intersections.

An aspect of some embodiments of the invention relates to the virtual revascularization of a vascular model.

In some embodiments, virtual revascularization comprises identifying portions of the vasculature relatively unaffected by disease. The disease comprises, for example, stenotic (narrow) regions of the vasculature. Optionally, the disease comprises aneurysm (widened) regions of the vasculature.

For example, the widest sections in a local region vasculature are considered "astenotic" or healthy in some embodiments. Construction of an astenotic, revascularized, and/or pre-stenotic vasculature (except where otherwise qualified, these terms are used interchangeably herein in reference to reconstructed vascular width estimations), in some embodiments, comprises estimation of a healthy vascular lumen size based on the healthiest vascular regions nearby which can be identified. Additionally or alternatively, identification of a healthy region comprises substitution of a homologous vessel—for example, a vessel from another portion of the same vascular tree, or a portion of another vascular tree which is matched to the modeled vascular tree in terms of one or more parameters such as age, gender, and/or body size.

In some embodiments, virtual revascularization comprises use of later- and an earlier-obtained images of a vascular tree. In some embodiments, the earlier images are used, in whole or in part, as an astenotic baseline, or as a basis for determining an astenotic state. In some embodiments, the astenotic vascular state is extrapolated, based, for example, on the determination that certain regions can be observed to close up over time, reflecting their stenotic character.

In some embodiments, revascularization comprises propagation of a healthy/normal/undiseased vessel region width estimation into a region of width change due to disease. The propagation comprises, for example, extrapolation between undiseased vascular regions, across regions which are or may be diseased. In some embodiments, propagation comprises weighting of the presumptively most healthy areas to be accordingly more important in setting a vascular width than other regions. Healthy vascular regions are, for example, relatively wide regions, and/or those nearest to an expected value based on location in the vasculature and/or other parameters such as patient vital statistics.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Mapped-Mode Vascular Tree Model

Figure 2A:
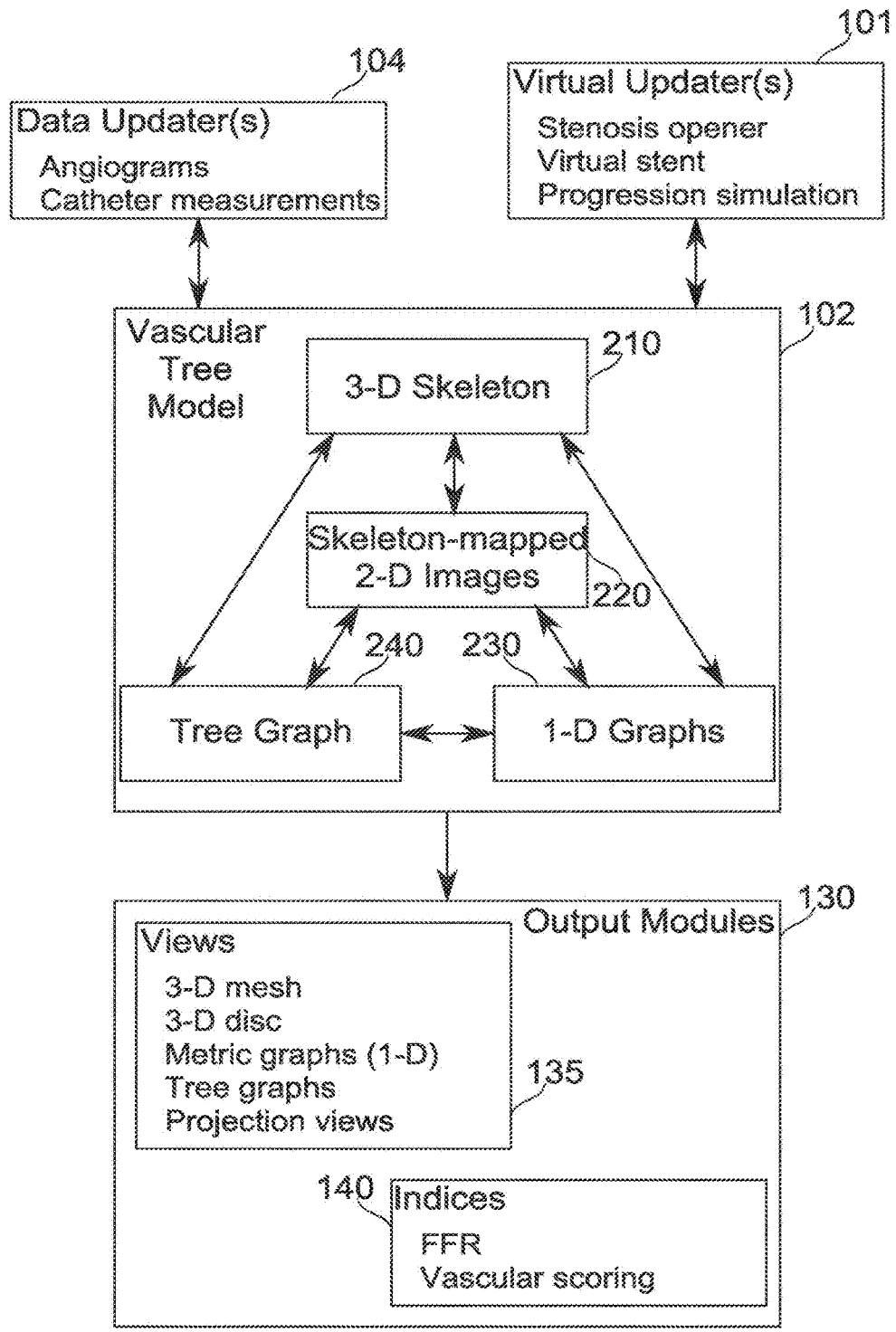
FIG. 2A is a block diagram listing particular examples by which some of the blocks of FIGS. 1A to JG are realized, according to some exemplary embodiments of the invention.
Figure 2B:
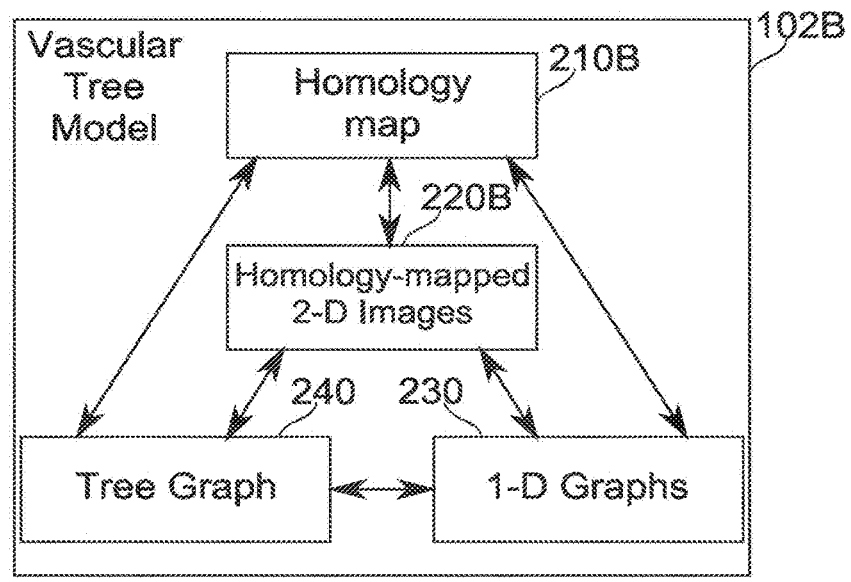
FIG. 2B is a block diagram giving an alternative example of a vascular tree model, according to some exemplary embodiments of the invention.

Reference is now made to FIG. 1A, which is a block diagram of a system 100 for production and use of a dynamically updatable vascular tree model, according to some exemplary embodiments of the invention. Reference is also made to FIG. 2A, which includes particular examples by which some of the blocks of FIG. 1A are realized, according to some exemplary embodiments of the invention; and to FIG. 2B, which is a block diagram giving an alternative example of a vascular tree model, according to some exemplary embodiments of the invention.

In some embodiments of the invention, initial image or other data 103 is provided to a vascular tree reconstructor 110, after acquisition by one or more imagers or data acquisition (DAQ) systems 120. In some embodiments, the image data is obtained, for example, by X-ray angiography, and/or from angiographic computed tomography (CT), magnetic resonance imaging (MRI), positron emission tomography (PET), optical coherence tomography (OCT), and/or intravascular ultrasound (IVUS). Optionally, the data provided comprises non-image data related to one or more locations of the vasculature; for example, data acquired from a catheter-mounted sensor and/or radiation source.

In some embodiments, the vascular tree reconstructor 110 reconstructs provided data 103 into a vascular tree model 102 of the vasculature. Herein, the system is described in relation to imaging of the vasculature of the mammalian heart—or more specifically the human heart-including, for example, the major arteries of the heart. It is to be understood that the system, changed as necessary, is applicable to the modeling of any other vasculature, according to the source of the initial data 103.

In some embodiments, the model 102 comprises a plurality of partial and/or complementary representations of the spatial relationships inherent in the initial data 103.

Reference is now made to FIGS. 5A-5E, which schematically illustrate a variety of representational modes for a vascular model 102.

Figure 5A:
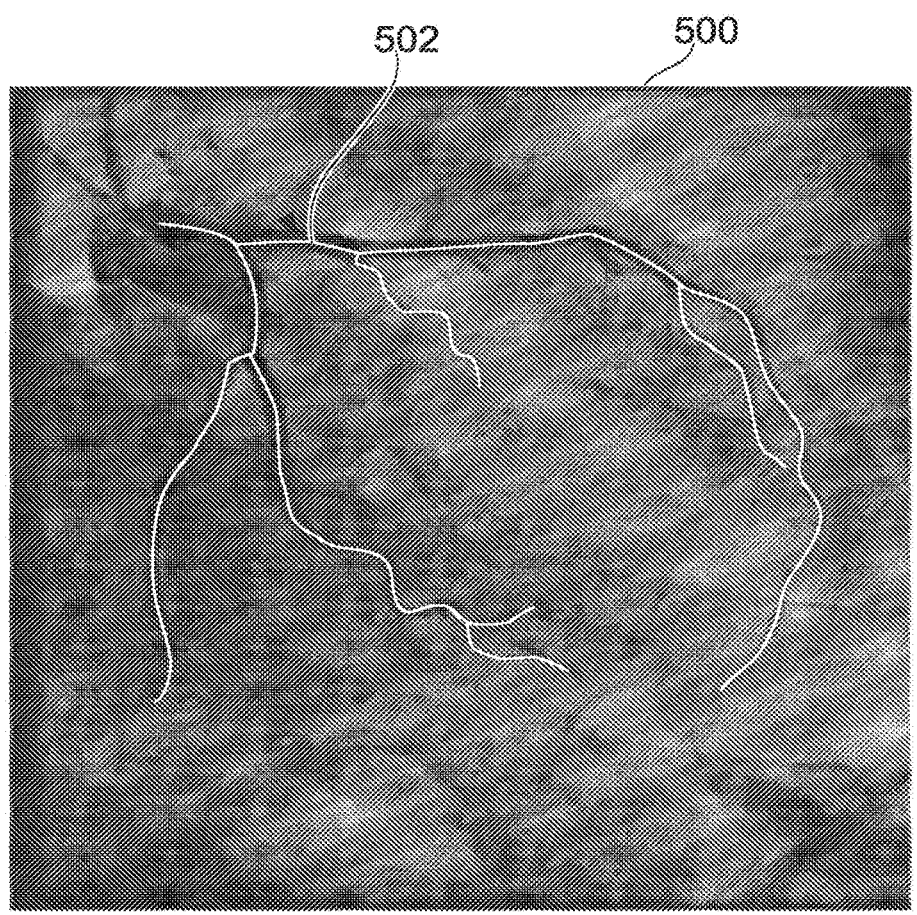
FIGS. 5A-5E schematically illustrate a variety of representational modes for a vascular model, according to some exemplary embodiments of the invention.
Figure 5B:
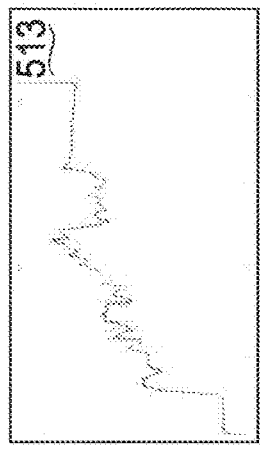
Figure 5B:
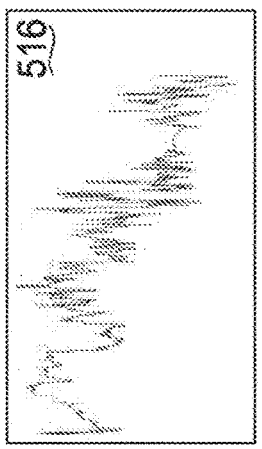
Figure 5B:
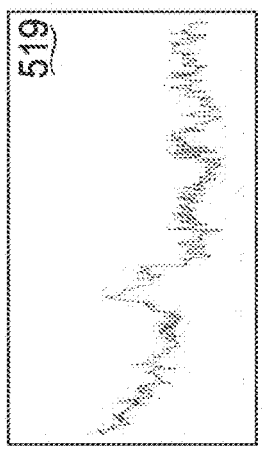
Figure 5B:
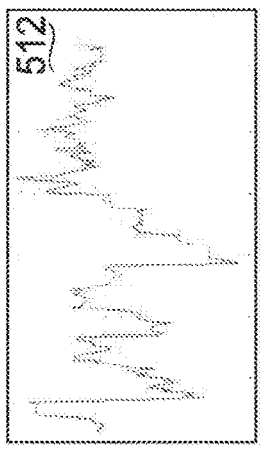
Figure 5B:
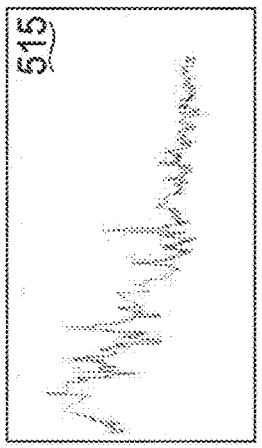
Figure 5B:
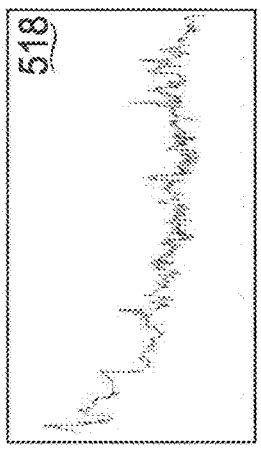
Figure 5B:
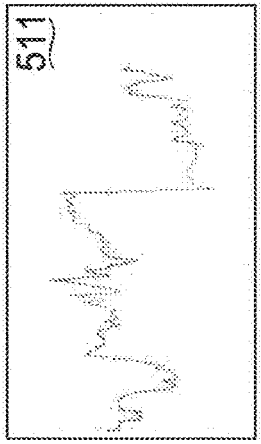
Figure 5B:
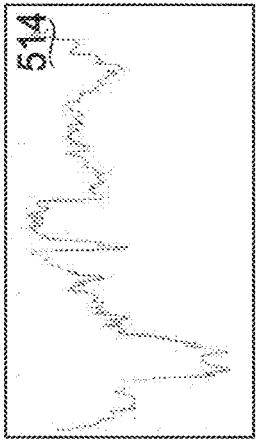
Figure 5B:
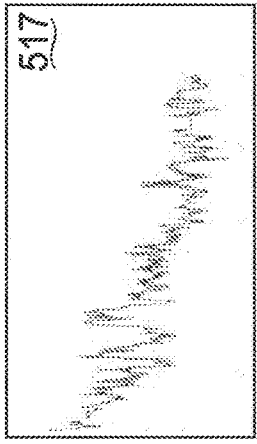
Figure 5C:
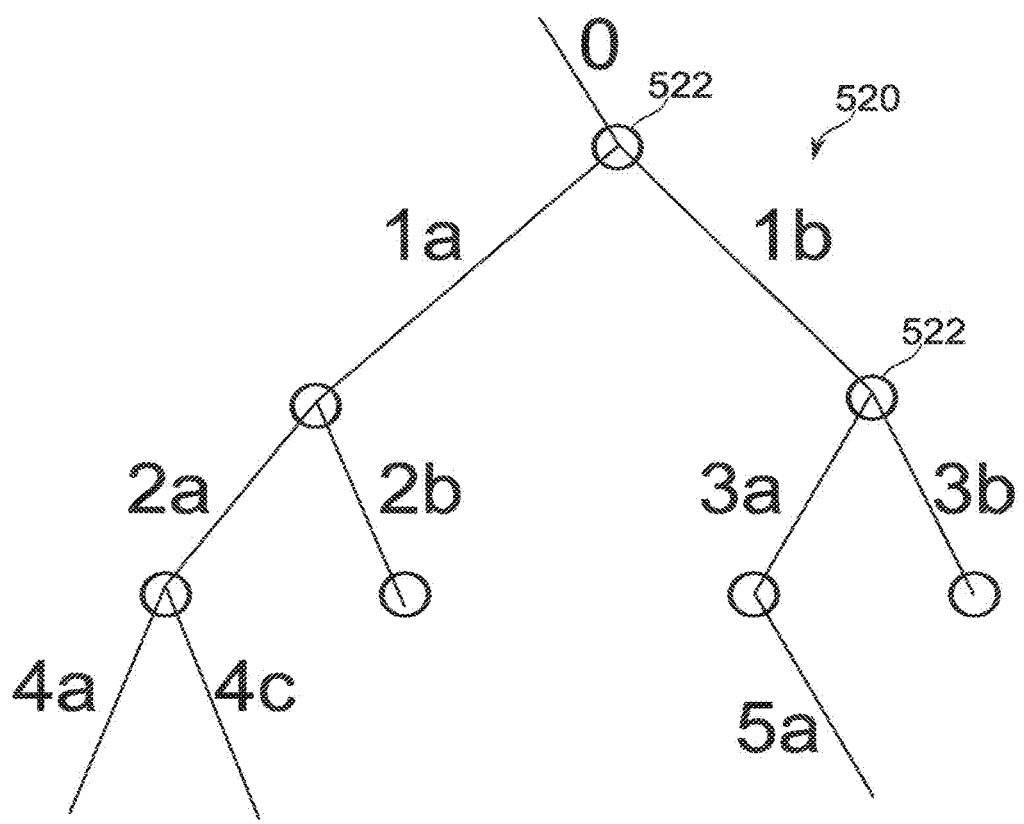
Figure 5D:
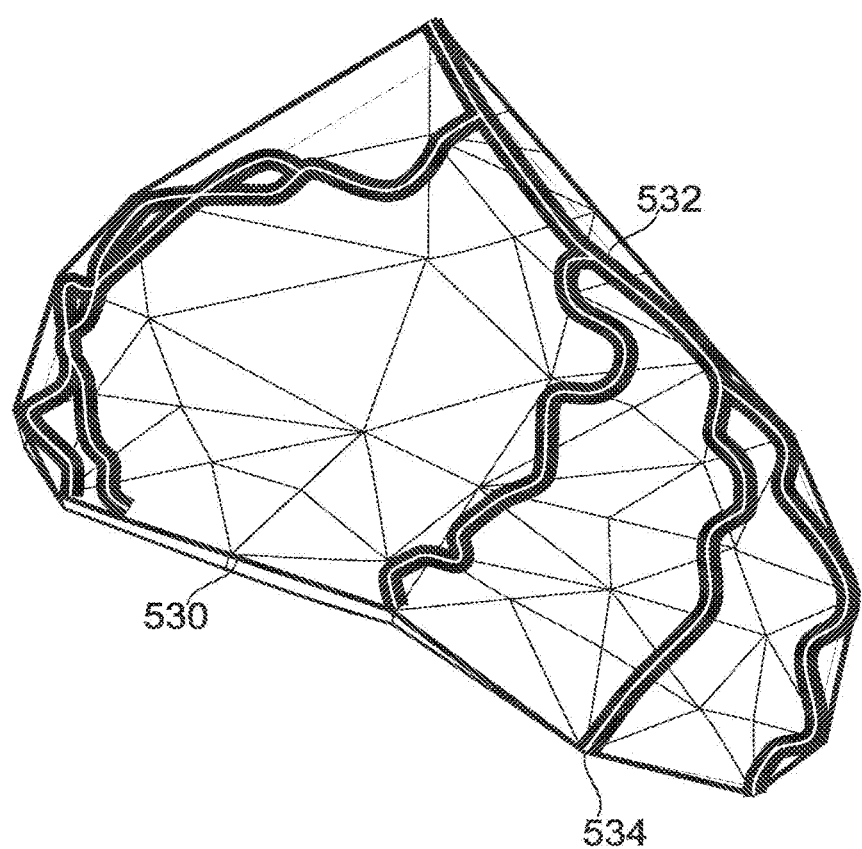

Representational modes comprise the capability to represent, for example:
- 2-D images 220, 500 of the vasculature (FIG. 5A) as provided with the initial data 103 and/or as derived by transformation thereof,
- a branched tree graph 240, 520 comprising a vascular co-ordinate system corresponding in lengths '0' and 'la-S a' (FIG. 5C) and/or branch points 522 to the skeletonized 3-D tree,
- 1-D graphs 230, 511-519 of one or more parameters varying along the length of segments of the modeled vasculature (FIG. 5B), and/or
- a skeletonized (thinned) 3-D tree 210, 534 which follows the routes of vasculature centerlines (FIG. 5D).

In some embodiments of the invention, a role performed by skeletonized 3-D tree 210 in providing a homology map is provided more generally in a model 102B by any data structure allowing determination of homologies among data regions (homology map 210B), and the skeleton-mapped 2-D images are more generally described as homology-mapped 2-D images 220B.

A data structure allowing determination of homologies comprises, for example, a structure in which parts of the vascular tree are represented, and these part representations in turn linked to other structures/data types which correspond to the represented part.

Parts are optionally defined at a level appropriate to the detail required by the further calculations which are to be performed. Represented parts of the vascular tree can be, for example, points along the vascular segments (as in a skeletonized 3-D tree, a 3-D mesh, or a 3-D volumetric representation), a branched tree structure having nodes and distances (optionally without associated 3-D location information), nodes and/or segments as such (with or without further detail such as centerline location), and/or another anatomically-anchored structure used as a basis for anchoring homology determinations.

In some embodiments, homology is represented without specific reference to a vascular tree representation as such, so that it comprises a "representational mode" only indirectly. For example, homologous data regions are, in some embodiments, tagged, listed, and/or otherwise associated together, optionally without the tags/listings/associations being themselves in direct relationships reflecting position and/or order.

The following examples serve as non-limiting indications the range of such homology representations contemplated. In embodiments of the invention where homology is represented at a fine scale (for example, at about the resolution of the data samples themselves, or with greater detail), data structure ordering which directly reflects positions of corresponding anatomical features is potentially advantageous as an organizational scheme (for example, by lending itself well to direct lookup). A skeletonized 3-D tree 210 exemplifies this case. In embodiments where homology is represented at a coarse, but still anatomically-anchored scale, a nodal homology structure has potential advantages. For example, vascular segment 2-D centerlines (for instance, vascular centerlines between adjacent bifurcations) are optionally associated as a whole to a specific nodal position in a simplified vascular tree characterized by linked nodes. In some embodiments, homology determination is independent of the global structure of a vascular tree. For example, projection mapping into three dimensions allows determinations of which segment centerlines "belong" together (according, for instance, to general features of proximity and/or orientation), optionally without first, and/or without directly determining the vascular tree relationships of the homology groups themselves.

Thus, in some embodiments of the invention, the problem of determining global structure, and the problem of determining which data reflect which part of the global structure, are treated separately, or in concert, to a degree appropriate to the particular metric or metrics which are to be calculated.

In particular, and with respect to the calculation of fractional flow reserve (FFR): calculations of vascular resistance based on individual 2-D images of vascular dimensions potentially provide sufficient sensitivity for reliable calculation of FFR based on the resistances of vessel segments measured in a vascular crown. Insofar as the resolution-intensive calculations of the FFR measurement can be confined to the raw 2-D data, 3-D calculation is potentially reduced to less intensive uses for other aspects of the FFR measurement, and/or replaced by non 3-D methods of determining the required information.

For example, determining which 2-D image to use for calculating a vascular resistance optionally comprises a selection from a homology group (for example, selection of a segment imaged at the most nearly orthogonal angle to the projection axis). At the scale, for example, of vascular segment identity, homology groups are calculated, in some embodiments, by "brute force" back-projection into three dimensions based on known image acquisition parameters, which potentially provides enough information, without further requirement for resolution of inconsistencies, to choose which segment images (recorded projections) are homologous. This is less stringent than a requirement to identify a well-defined 3-D centerline to which each imaged segment is mapped in detail. Alternatively or additionally, homologies are determined according to similarities among vascular structures in the original 2-D images.

Also for example, obtaining vascular tree detail sufficient to know which segments connect to which, and in what branching order, is not necessarily a problem requiring full 3-D reconstruction. In some embodiments (based, for instance, on knowledge of segment homology groups, feature registration, or another technique), partial 2-D images of a vascular tree are combined to form an overall model comprising vascular segments and their branch point connections.

It should be emphasized that the above-listed representational modes and homology structures are exemplary, and not proposed as limiting to the invention. In some embodiments, for example, model 102 comprises a representation, for example, of a 3-D mesh and/or 3-D disc model 540 of the walls 549 of the modeled vasculature (FIG. 5£). In some embodiments, spatial dimensionality comprises an alternative co-ordinate system; for example, the positions of vascular regions 532 are represented in two dimensions relative to a three-dimensional shell 530 representing the surface of the heart.

In some embodiments of the invention, representational modes are configured such that data represented under one mode relates to data represented under another mode by a mapping, for example:

from or to a three-dimensional space corresponding to a volume of imaged vasculature,
from or to the two-dimensional coordinate system of an image plane,
from or to the branched one-dimensional coordinate system of a vascular tree, from or to the one-dimensional coordinate system of a vascular segment,
or another mapping.

For example, a two-dimensional vascular centerline representation 502 corresponds m some embodiments to a three-dimensional representation of vascular centerlines 534. In some embodiments, mapping comprises temporal information. Temporal information is optionally cyclical, for example, the phase of a heartbeat and/or respiratory movement. Optionally, temporal information is non-cyclical, representing, for example, the absolute and/or relative time of data acquisition over any period from fractions of a second to years, according to the embodiment. Optionally, mapping comprises data in another dimension; for example, a condition of pharmacological and/or physiological manipulation.

In some embodiments, one or more of the representational modes comprises a set of tags. Optionally, this provides a means of mapping homologous regions among other representational modes, or optionally, within a representational mode—each homology group corresponding to a tag. For example, regions of 2-D images corresponding to a particular vascular segment are homology mapped to one another, through a tag corresponding to the vascular segment. Optionally, the designation of a region is explicit at a pixel level (for example, along a path). Additionally or alternatively, one or more metrics or parameters derived from a 2-D region are assigned to a tag, structuring the homology mapping without explicitly reference to spatial co-ordinates. The "tag" is, for example, an explicit label such as a string or number, membership (directly or by hash or indexing value) in an array or list structure, or any other structure expressing association of data structures as known to one skilled in the art.

This mapping style, in some embodiments, comprises establishing a form of coarse-grain homology. For example, (in contrast to assigning pixels of 2-D images to locations within a common 3-D representation), regions of 2-D images, and/or metrics derived therefrom, are tagged, without assignment to positions within a common spatial coordinate system Additionally or alternatively, tagging comprises spatial information, but the coordinate system is non-Cartesian; for example, it is according to branch order position.

Updates to the Vascular Tree Model

"Virtual" Updates

In some embodiments of the invention, one or more virtual updater modules 101 is provided. A virtual updater 101 is configured to receive information from vascular model 102, and transform it to create one or more new vascular representations in the mode of one or more of the representational modes of vascular model 102. Optionally, the new representation is passed back to the model and integrated therein—to replace and/or supplement the existing model representation. It should be noted that, for simplicity of discussion, this is the flow of modeling information laid out in FIGS. 1A to JG, 2A, and 2B, and generally adhered to in the descriptions herein. Optionally, however, a new model is created, and/or the transformed vascular model information is passed directly to an output module 103. Such variations on the flow and storage of calculated information are to be considered as equivalent alternative embodiments of the invention wherever applicable in accordance with the disclosures herein.

In some embodiments, vascular model 102 exposes 1-D or 2-D data representations of the vasculature to virtual updater 101, additionally or even alternatively to exposing 3-D representations of the data. Exemplary descriptions of vascular model data representations consumed and produced by virtual updaters 101 are provided, for example, in relation to FIGS. 3A-3F, hereinbelow.

In some embodiments of the invention, a virtual updater comprises a module for one or more of the following tasks:

determining an "unstenosed" state of a blood vessel segment, and in particular, an estimate of the geometry of a blood vessel as if a region of stenosis were opened therein;
modeling the effect on a blood vessel segment of the insertion of a stent therein; and/or
modeling changes within a blood vessel segment due to the progression of time.

Embodiments of virtual updaters are described hereinbelow, for example, in relation to FIGS. 6-9. The present discussion focuses on the use of images to model blood vessel geometry, in particular vascular lumen diameter, and/or modifications thereto. However, it is to be understood that one or more other parameters of interest are modeled in some embodiments, either together with or separately from vascular width. For example, modeling in some embodiments represents vascular tortuosity, vascular elasticity, vascular auto-regulatory capacity, vascular wall thickness, flow characteristics, and/or another functional and/or anatomical parameter of the vasculature.

Data Updates

In some embodiments of the invention, one or more data updater modules 104 is provided. A data updater module 104 is configured to receive image and/or other data 115 from an imaging means or other DAQ source, and to convert it into a form which can be provided to the vascular model 102. Image data is provided, for example, by X-ray angiography, and/or from CT, MRI, PET, OCT, and/or IVUS. In some embodiments, non-image data is provided, for example, by means of a sensor and/or sensed radiation source advanced through the vasculature on a catheter.

Figure 4A:
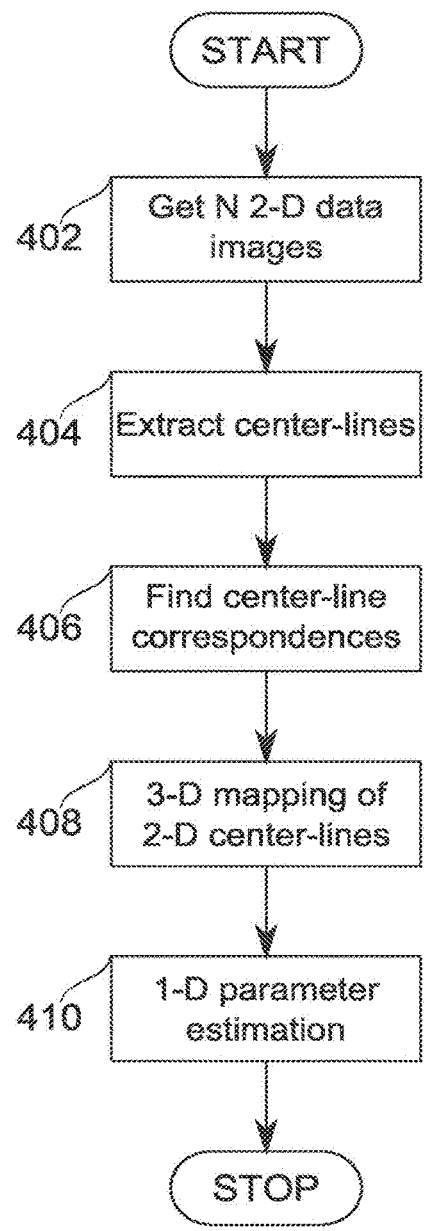
FIG. 4A schematically illustrates the operation of a vascular tree generator, according to some exemplary embodiments of the invention.

Description of how some embodiments of a data updater function is provided by first making reference to FIG. 4A, which schematically illustrates the operation of a vascular tree generator 110, according to some exemplary embodiments of the invention. Vascular tree generation is described, for example, in International Patent Application No. IL2014/050044 filed Jan. 15, 2014 by the Applicant, the contents of which are included herein by reference in their entirety.

At block 402, in some embodiments, vascular tree generator 110 receives a number of 2-D images from an imaging means. The images are received along with data describing the conditions of their acquisition, which comprises, for example, spatial calibration information, heartbeat phase information, and/or respiratory phase information. Initially, the images potentially comprise a number of inconsistencies in their representation of a common vascular tree. Inconsistencies can arise, for example, from motion (heart beat and respiration), and/or from uncertainty due to imprecision and/or error in alignment and calibration. Potentially, there are also ambiguities in the image, due, for example, to overlapping structures and/or signal-to-noise limitations.

From this point, a sequence of operations using the received data begins which is applicable to resolve the inconsistencies, ambiguities, or outright errors inherent therein. The method is also applicable to generate the mapped-mode vascular tree model described hereinabove. It is potentially convenient for model generation to proceed directly into a multi-modal representation which is suitable for manipulation, including updating. It is to be understood, however, that a multi-mode representation is derivable by other methods; for example, by analysis and transformation of a 3-D vascular model. Such a model might be the output of a 3-D imaging system, for example, which is provided as input data 103.

At block 404, in some embodiments, vascular centerlines are extracted from the provided 2-D images. Centerline extraction comprises, for example, anisotropic diffusion, followed by Frangi filtering, hysteresis thresholding, and thinning of the result until a one-pixel thick vascular skeleton is obtained. In further detail, these are described as follows.

Anisotropic diffusion of 2-D gray-scale images reduces image noise while preserving region edges-smoothing along the image edges, and removing gaps due to noise. In some embodiments, the basis of the method used is similar to that introduced by Weickert in "A Scheme for Coherence-Enhancing Diffusion Filtering with Optimized Rotation Invariance" and/or "Anisotropic Diffusion in Image Processing" (Thesis 1996).

A Frangi filter, based on Hessian eigenvectors, comprises computation of the likeliness of an image region to be within a vessel. Frangi filtering is described, for example, by Frangi, et al. "Multiscale vessel enhancement filtering", Medical Image Computing and Computer-Assisted Intervention-MICCA'98. In some embodiments, another filter is used, for example a threshold filter, or a hysteresis threshold filter, whereby pixels of an image are identified as belonging within an image region of a vessel.

A hysteresis threshold processes the image into a black-white figure (or other binary representation) representing vascular locations in the angiographic projection image. In general, a hysteresis threshold filter operates by applying at least two criteria to determine these locations: a first criterion of intensity set, for example, so that each pixel selected has a high certainty of being a vascular location; and a second criterion combining a less stringent intensity setting and proximity to now-known vascular locations. Thus, at least high and low thresholds are used. In an exemplary implementation, first the algorithm detects the pixels which are (for example) brighter than the higher threshold; these are labeled as vascular pixels. Next, the algorithm also labels as vascular those pixels with brightness higher than the low threshold, and also connected across the image to pixels already labeled as vascular pixels.

Thinning is, for example, by a thinning convolution, applied iteratively until the black-white image segments are reduced to lines representing the vascular centerlines.

The 2-D vascular centerlines thus found represent, for example, 2-D centerlines 502 of FIG. 5A. In some embodiments, these provide two-dimensional anchors for the relationships of 2-D blood vessel images, which find correspondence in the course of vascular tree reconstruction to positions in a three-dimensional vascular tree skeleton.

At block 406, in some embodiments, the centerline correspondences are found. Finding centerline correspondences comprises, for example, motion and other error compensation, constraining of vascular positions to the heart surface, and identification of homologous vascular segments.

In an exemplary method of motion compensation, a subset of images (comprising a plurality) with identified 2-D centerlines is selected for processing. What follows is a form of motion compensation, insofar as positional errors due to motion (though also other positional errors) are corrected by annealing to a position of consensus between several individual images. Centerlines are optionally dilated, and a centerline projection back into 3-D performed at block, based on the current best-known projection parameters for each image. Initially these are, for example, the parameters expected based on the known calibrations of the imaging device. The resulting projected volume is skeletonized, in some embodiments, to form a "consensus centerline". The consensus centerline is projected back into the coordinate systems of 2-D images not used in forming the consensus centerline. An optimization procedure then adjusts projection parameters for the 3-D centerline into each 2-D image to fit more closely centerlines found within the image itself. This adjustment is used to adjust the projection parameters associated with each image. The method is iterated on until a criterion for completion is met.

Refinement, in some embodiments, comprises the incorporation of one or more additional constrains. For example, the "heart shell", on which the arteries of the heart lie, can be determined in some embodiments by the intersections among 3-D projections of 2-D images. Images or regions of images wherein points fall off of this heart shell can be ignored, or constrained to fall upon it.

Although a rough correspondence mapping between 2-D and 3-D is created at this stage, the method continues, in some embodiments, with direct image-to-image mapping of centerline segment identities—that is, determination of their homologies. In some embodiments, a base 2-D image is selected for homology determination. The vascular centerlines of another image are projected into the plane of the base image. The projected vascular centerline is dynamically dilated, noting where intersections with the base image vascular centerline first occurs, and continuing, for example, until all homologies have been identified. Dynamic dilation comprises, as an example among equivalent alternatives, gradual expansion of the centerline, for example by application of a morphological operator to pixel values of the image.

The 3-D centerline region thus found (and/or as subsequently refined) could be used, in some embodiments, to represent the 3-D skeleton 210 of the vascular tree model. It is a potential advantage, however, to further refine the 3-D centerline positions.

At block 408, in some embodiments, homologous regions of 2-D centerlines are mapped back into 3-D to create a more refined 3-D centerline model.

An initial segment portion comprising a vascular centerline is chosen, along with an initial homologous group of centerline points along it (for example, a point from an end) in the different 2-D images. Selecting groups of candidate centerline points in order along the segment, each candidate pairing of homologous points is projected into 3-D. The pair which is most suitable to extend the 3-D centerline so-far established is chosen to continue the centerline to the next point. Suitability is determined by criteria such as distance and direction, for example.

The result corresponds, in some embodiments, to the 3-D skeleton 210 of the vascular tree model. In some embodiments, this skeleton is reduced to a tree graph 240, wherein position is encoded by distance along each segment of the 3-D skeleton, relative to notes at which branching occurs.

At block 410, in some embodiments, 1-D parameter estimation is performed. Details vary depending on the parameter to be estimated. In some embodiments, vascular width is the estimated parameter. Vascular width is estimated from 2-D images, for example, by generating for each wall of a vascular segment an edge graph, finding connected routes along the edge graphs, and then determining the distance separating the two connected routes as a function of position along the vascular centerline.

Edge graph generation begins with selection of a 2-D image (for example, an image where the vascular segment of interest is of maximum length). Starting vascular width is estimated, for example, by generating an orthogonal profile to the center line and choosing the peak of the weighted sum of the first and second derivatives of the image intensity along the profile. Profiles built at sampled points along and orthogonal to the vascular segment are assembled in a rectangular frame, forming the edge graph. Routes for each side are found along the edge graph at approximately the distance of the initial radius, for example, by minimizing the energy that corresponds to a weighted sum of the first and second horizontal derivatives. Distances between edge routes orthogonal to the centerline are then treated as the vascular widths, wall-to-wall, along the vascular segment. Optionally, the 2-D centerline is re-centered after determination of the wall positions.

The 1-D width graphs generated by this procedure correspond in some embodiments, to the 1-D graphs 230 which are part of the vascular tree model. In some embodiments, 1-D graphs are calculated for one or more additional vascular parameters such as resistivity to flow, roughness, elasticity, contrast density, or tortuosity.

Figure 4B:
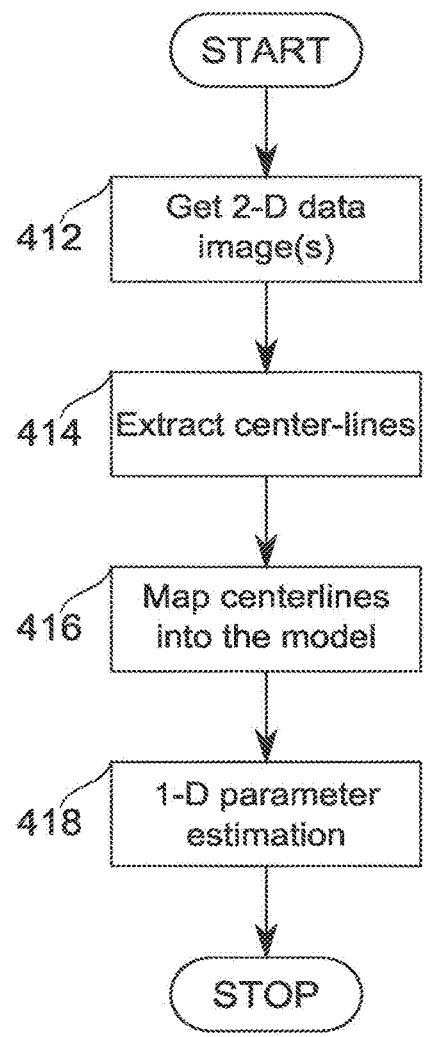
FIG. 4B illustrates the addition of new data to an existing vascular tree model, according to some exemplary embodiments of the invention.

Reference is now made to FIG. 4B, which illustrates the addition of new data to an existing vascular tree model, according to some exemplary embodiments of the invention.

The blocks of FIG. 4B describe an exemplary form of data updater module 104, but it is to be understood that a data updater module 104 is not limited to this description.

At block 412, in some embodiments, image data is obtained. The image data is from any source which has produced images of the modeled vasculature, and not necessarily the source which produced the images used to originally build the model.

At block 414, in some embodiments, 2-D vascular centerlines are determined for blood vessels in the newly provided images, for example, as described in relation to block 404.

At block 416, m some embodiments, the new 2-D vascular centerlines are mapped to the 3-D centerline of the model. In some embodiments, where sufficient information is available for projection of the centerlines into 3-D relative to the 3-D centerline space, the procedure for mapping comprises finding nearest intersections between the 3-D centerline space and the various projection lines.

Additionally or alternatively, 2-D centerlines can be matched between a new image and an already-mapped 2-D image, for example by geometrical transformation of one or both of the images to minimize centerline distances. The new image then takes its mapping to the common 3-D skeleton transitively from the transformed mapping of the previously-mapped image. In some embodiments, a likely matching image is selected based on metrics such as relative segment length. In some embodiments, registration of multiple previously-mapped images is attempted, and the result with the least matching error retained. This procedure is potentially advantageous when there is little or no 3-D calibration information available. It should be noted that a new image is potentially mapped to the 3-D centerline without explicit determination of the parameters of an image plane relative to this 3-D centerline space. However, it is a potential advantage of some embodiments that matching transformations used among images are equivalent to plane rotations, translations, and scalings.

In another additional or alternative procedure, the 3-D centerline is projected into the plane of the new image with variations in projection angle, rotation, and scaling, until a minimized-error fit is obtained.

In some embodiments, mapping of a new image into the model is relative to a non-3-D representation, such as the tree graph 240. For example, segment identification is performed by matching of nodes and relative segment lengths. It is to be understood that after initial import of an image with respect to one of the representational modes of the model, correspondences to additional representation modes can be established by taking advantage of correspondences known from previous calculations. In this way, direct or indirect homology-tracing pathways can be traveled among the data points available.

At block 418, m some embodiments, 1-D parameter estimation for the new images occurs, for example as described in relation to block 410.

In some embodiments, non-image data is imported to the vascular tree model. For example, in some embodiments, position of a catheter along a vascular segment is known in relation to data acquired by a sensor positioned on the catheter, or by another sensor which detects radiation emitted from a position on the catheter. In such embodiments, data is mapped into the model, for example, directly as a 1-D graph.

Scenarios in which a data updater module 104 is used are described, for example, in relation to FIGS. 12-14 hereinbelow.

Data Structures Supporting Within-Record Partial Model Updating

Figure 18A:
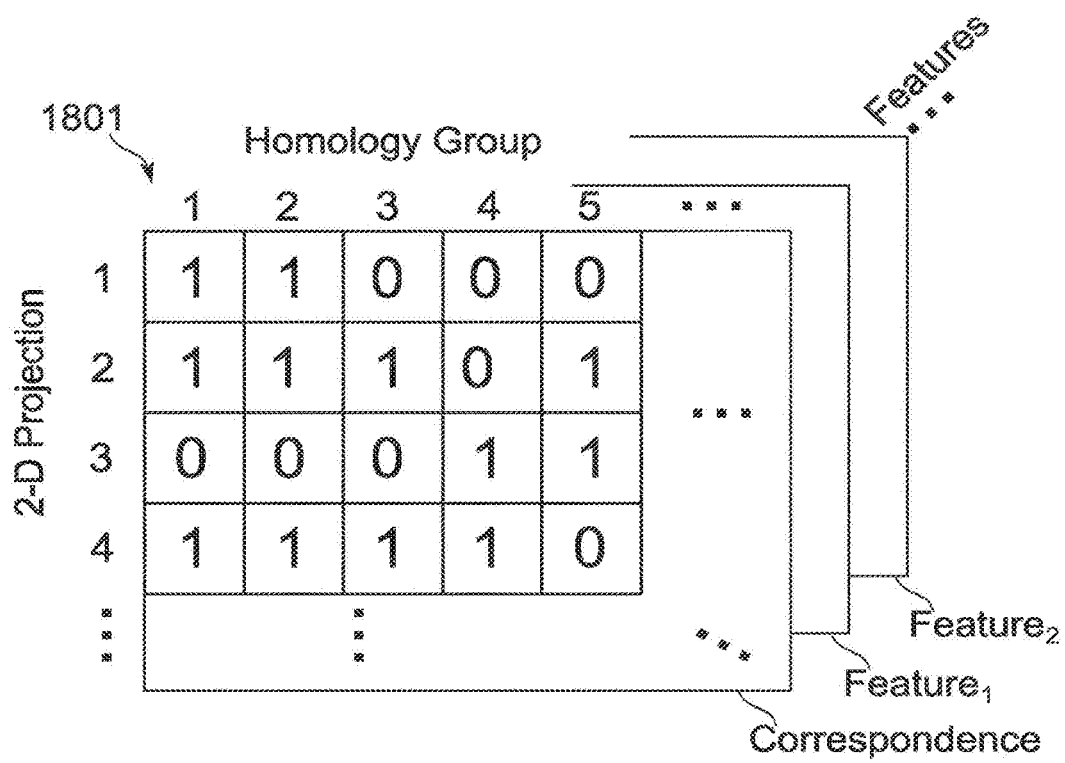
FIG. 18A shows a correspondence-indexed matrix data structure, according to some exemplary embodiments of the invention.
Figure 19:
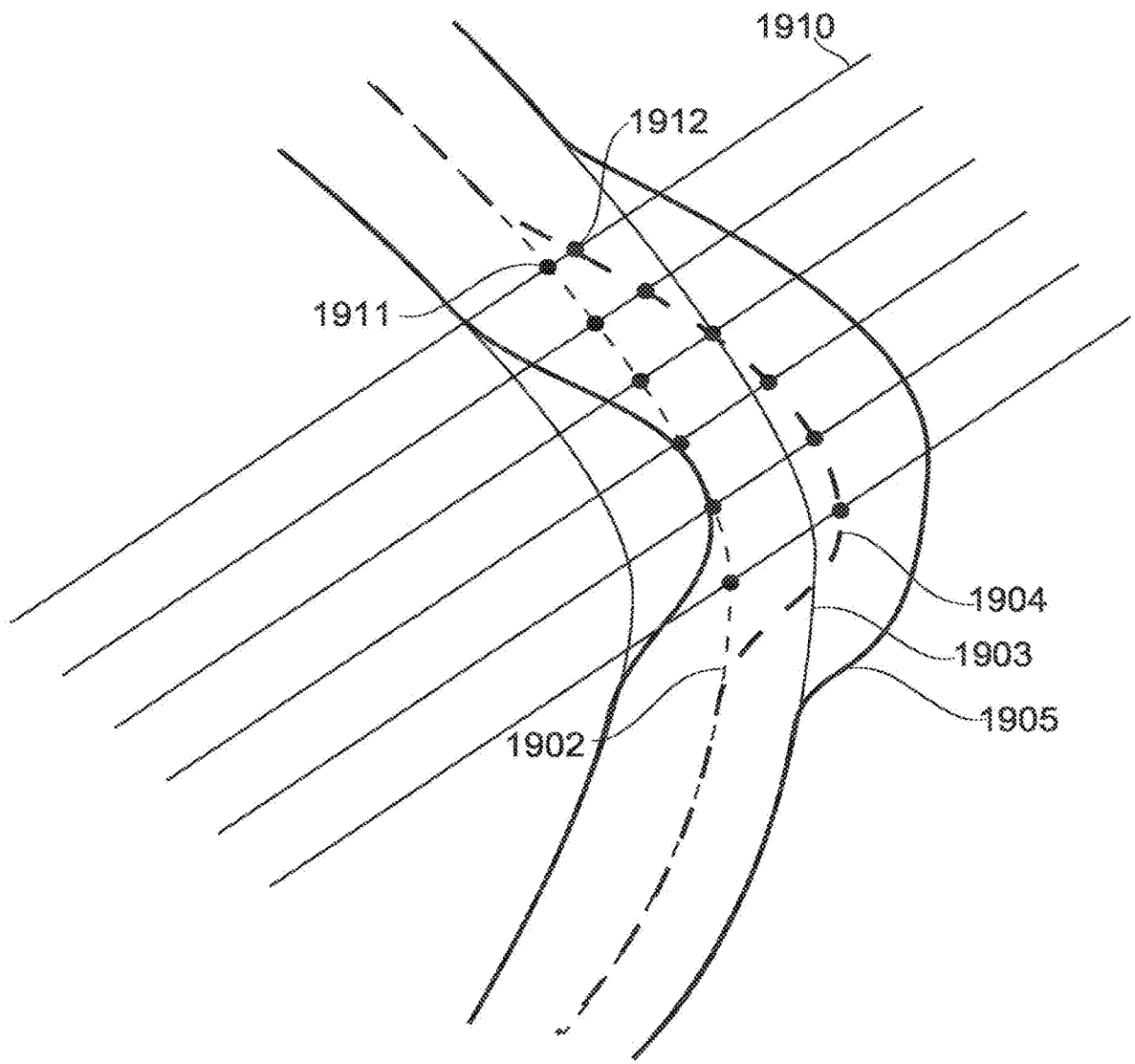
FIG. 19 shows partial updating at the level of a partial segment centerline, according to some exemplary embodiments of the invention.

Reference is now made to FIG. 18A, which shows a correspondence-indexed matrix data structure, according to some exemplary embodiments of the invention. Reference is also made to FIG. 19, which shows partial updating at the level of a partial segment centerline, according to some exemplary embodiments of the invention.

In some embodiments, the particular data structure or structures in which a vascular tree model is recorded are selected based in part on the resolution at which structural updating is desired. An embodiment allowing the option of fine control/updating of vascular structure updating is shown in FIG. 18A. The data block 1801 represented is a representation of a single vascular segment or branch, among a plurality of such branches represented by the whole model.

In some embodiments, the entries along the dimension of the matrix of the correspondence plane labeled "Homology Group" correspond to indexes in a 3-D centerline description of a vascular segment. Optionally, the "2-D projection" dimension corresponds to available 2-D projections (images) in which the corresponding 3-D centerline points appear (matrix value=1) or don't appear (matrix value=0). Optionally, the "Feature 1", "Feature 2" (and optional additional) planes comprises further matrices of equal dimensions, with each entry being a value such as a radius at the given centerline offset (for example, a radius estimated from either side of the centerline to the vascular wall). In some embodiments, there is such a structure available for each vascular segment in the vascular tree of interest.

In such an embodiment, details of the vascular anatomy are closely tied to representations of the various data sources that represent it. It should be understood, however, that a similar data structure could be developed which creates homology groups at a higher level of abstraction.

For example, each "Homology Group" (which can be, for example, different data for the same approximately sample-sized region in a vasculature, for the same segment region in a vasculature, or for another structure represented in common among different data representations), in some embodiments, corresponds to a whole vascular segment, with the "2-D Projection" correspondence matrix representing whether that segment is found within the corresponding set of image data. Feature entries in this case comprise, for example, vascular resistance and/or vascular volume; optionally, feature entries are whole arrays, for example, of associated image data, and/or of 2-D vascular centerline positions.

Turning to FIG. 19, an example of the modification of a row of the structure of block 1801 is shown. In the example, schematic projection images a first vascular segment state 1903 (thin walls) and a second vascular segment state 1905 (thick wall) are shown overlaid on one another. The segment states are associated with centerline representations 1902 and 1904, respectively.

In some embodiments of the invention, mapping of points from the new vascular state 1905 into the old vascular state 1903 is according to epipolar lines 1910, shared between the projections to a 3-D skeleton centerline of the points of centerlines 1902 and 1904 (for example, the epipolar line projection of new centerline 1904 onto the projection plane of old centerline 1902). Epipolar lines thus define homologies, for example, between old centerline point 1911, and new centerline point 1912.

In the model itself, the update optionally comprises wholesale replacement of original positions with new positions; additionally or alternatively, a new record is created reflecting the partial update. One use of such a partial update is to enhance the resolution of a portion of a vascular segment. In particular, in some embodiments, a stenotic region is analyzed (for example, re-imaged) with higher resolution than is available for the vascular tree as a whole, potentially allowing the dominant flow-resistance features of that vascular portion to be modeled with greater detail. The ability to perform partial updates allows the detailed model to be grafted into a low-resolution—but potentially more complete in extent-model of the vasculature region of interest.

Data Structures Supporting Record-Level Partial Updating

Figure 18B:
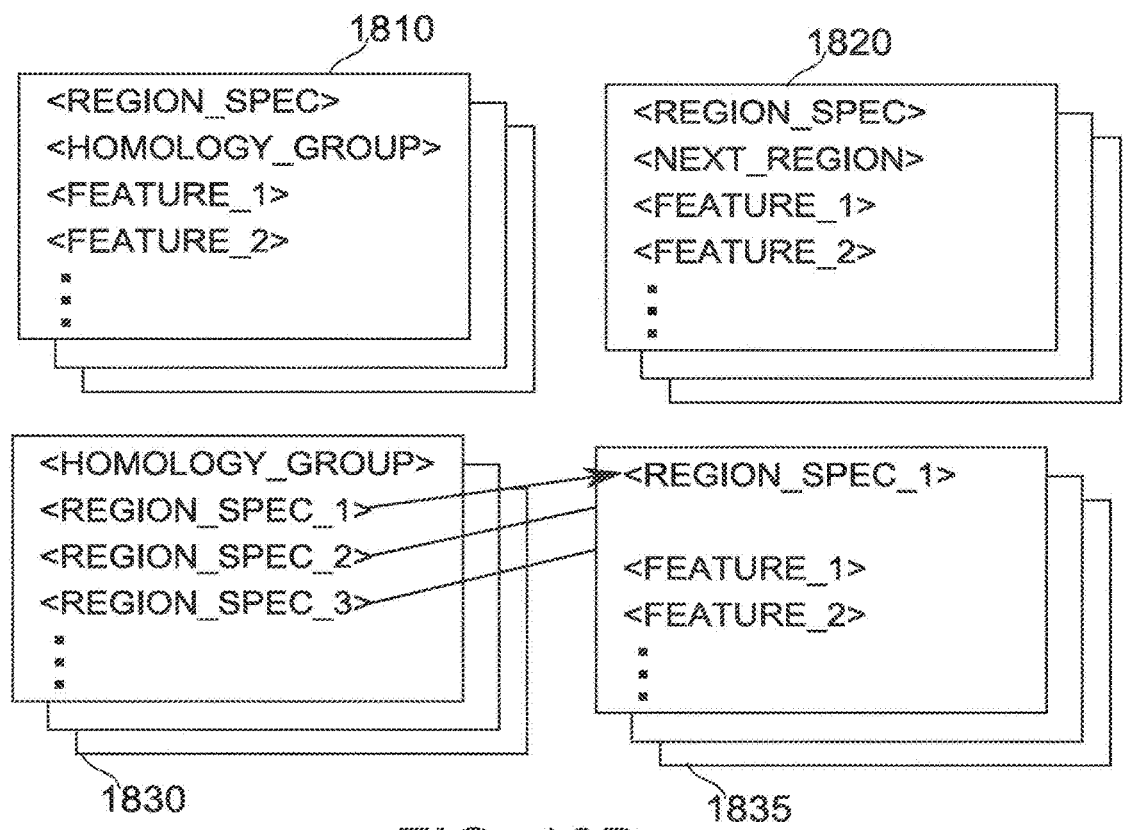
FIG. 18B schematically illustrates a selection of partially updatable model data structures, according to some exemplary embodiments of the invention.

Reference is now made to FIG. 18B, which schematically illustrates a selection of partially updatable model data structures, according to some exemplary embodiments of the invention. The data structures are preferably implemented by programmable computer, the program, computer, and memory thereof taking, for example one of the forms described hereinabove. Embodiments of "collections" of structures, as next described, are variously constructed, for example, as sequential lists, linked lists, arrays, index collections to structures, or another data structure as known in the art of computer programming.

In some embodiments, a region specification data structure 1810 is shown comprising a collection of 2-D image region specifications (<REGION_SPEC>), each of which contains a reference to a particular homology group (<HOMOLOGY_GROUP>), as well as a collection of features (<FEATURE 1>, 1<FEATURE 2>, . . . ) which are associated with the region.

In some embodiments of the invention, a region specification comprises a reference to a structured collection of data which describes and/or references, for example, a 2-D projection image or image region. Additionally or alternatively, the region specification specifies a path through such a region, such as a vascular segment centerline, or other morphologically descriptive structure.

In some embodiments of the invention, a homology group reference is a form of tag (a number, string, or other identifier) which is used in common among all region specifications belonging to the same homology group. Optionally, another structure describes the homology group itself, for example in a reciprocal form such as homology group specification 1830. This provides a potential advantage for ready homology group lookup. Additionally or alternatively, lookup is performed on the fly, for example, by inspecting the region specification collection.

In some embodiments of the invention, a feature is any feature which is calculated for the data associated with the region specification. Such features can comprise, for example, vascular segment width metrics (for one or more points along the vessel, one or more radii, diameter, up to a fully circumferential specification), segment length, flow resistance, flow capacity, pressure levels, tortuosity, or any other vascular and/or vascular-related parameter, for example as described herein and/or in a document included by reference herein. Optionally, features are included directly, and/or referenced by the region specification structure. Optionally, features are scalar value, arrays, lists, or any other data structure appropriate to representing feature characteristics.

Optionally, features include specifications of how a particular region specification is related anatomically to other region specifications. Additionally or alternatively, a homology group specification contains such information. Additionally or alternatively, a separate vascular tree-specifying structure is used which specifies such relationships, for example, in terms of homology groups.

With specific reference to partial updating and the use of homology groups, it can be seen that as new data becomes available, it is a straightforward process to add a new region specification 1810 to the current collection, with a homology group referencing a particular vascular structure selected as appropriate, even if the actual vascular structure represented is in a significantly different state than other members of the same homology group. Optionally, differences in state (for example, with stent/without, data acquired at different states of disease progression, differences of manipulation, and/or difference of pulse cycle phase) are recorded with the region specification, for example, as an additional feature.

In some embodiments, at the time when a calculation is performed based on the features of some subset of the available region specifications, selection is optionally performed, for example, on the basis of homology group, state-identifying and/or other features, features as evaluated relative to other members of the same homology group, aspects of the region specification data directly. The model itself is thus able to incorporate many different alternative, even mutually inconsistent, views of the same vasculature. For partial updating at a finer structural level, a single regional specification (for example, based on an image taken of a specific vessel after stenting, or a regional specification which models the effects of such stenting) is swapped into a regional specification selection which is otherwise based on pre-stenting vascular information.

It should be understood that the feature of record-level selection, addition, and removal of data enabled by structures such as those of FIG. 18B is combinable with sub-record modifications such as described in relation to FIGS. 18A and 19.

In some embodiments, a region specification data structure 1820 comprises a collection of 2-D image region specifications (<REGION_SPEC>), each of which contains a reference to another region specification in the same homology group (/<NEXT_REGION>), as well as a collection of features (<FEATURE 1>, /<FEATURE 2>, . . . ) which are associated with the region.

In most respects, in some embodiments, region specifications 1820 share the characteristics of region specification 1810. A difference of region specification 1820 is the structuring of the homology group as a linked list—referencing by a /<NEXT_REGION> member another region specification in the same homology group. Optionally the linkage is to one or more groups; the next region name is exemplary only. This demonstrates that a homology group is potentially implemented as an association among other data structures; the group can be expanded or contracted by adjusting linkages.

At block 1830, in some embodiments, a data structure is shown comprising a collection of homology group specifications (<HOMOLOGY_GROUP>), each comprising a collection of 2-D image region specifications (<REGION_SPEC>), and/or references to the collection.

In some embodiments, a homology group structure 1830 is provided that contains references to the region specifications belonging to it, analogous to the structure of one column of the data structure of FIG. 18A, except that entries are provided as needed, rather than in a full matrix. Optionally, region specifications are contained within the structure; additionally or alternatively, the structures are in referenced. For example, any of region specifications 1810, 1820, and/or 1835 can be referenced from a separate homology group structure 1830.

At block 1835, in some embodiments, a data structure is shown comprising a region specification which is optionally contained and/or referenced by another structure, such as a homology group structure 1830. The primary difference from regions specification structure 1810 is that homology group association is according to how it is referenced/contained, rather than by what it itself references/contains.

Output Modules

Returning the discussion to the elements of FIG. 2A, output modules 130 are divided, for purposes of exposition, into views 135 and indices 140. Some embodiments of output modules combine functions of each output module type. Output modules described herein provided as exemplars, without limitation of the form which an output generated based on the vascular tree model 102 can take.

Figure 5E:
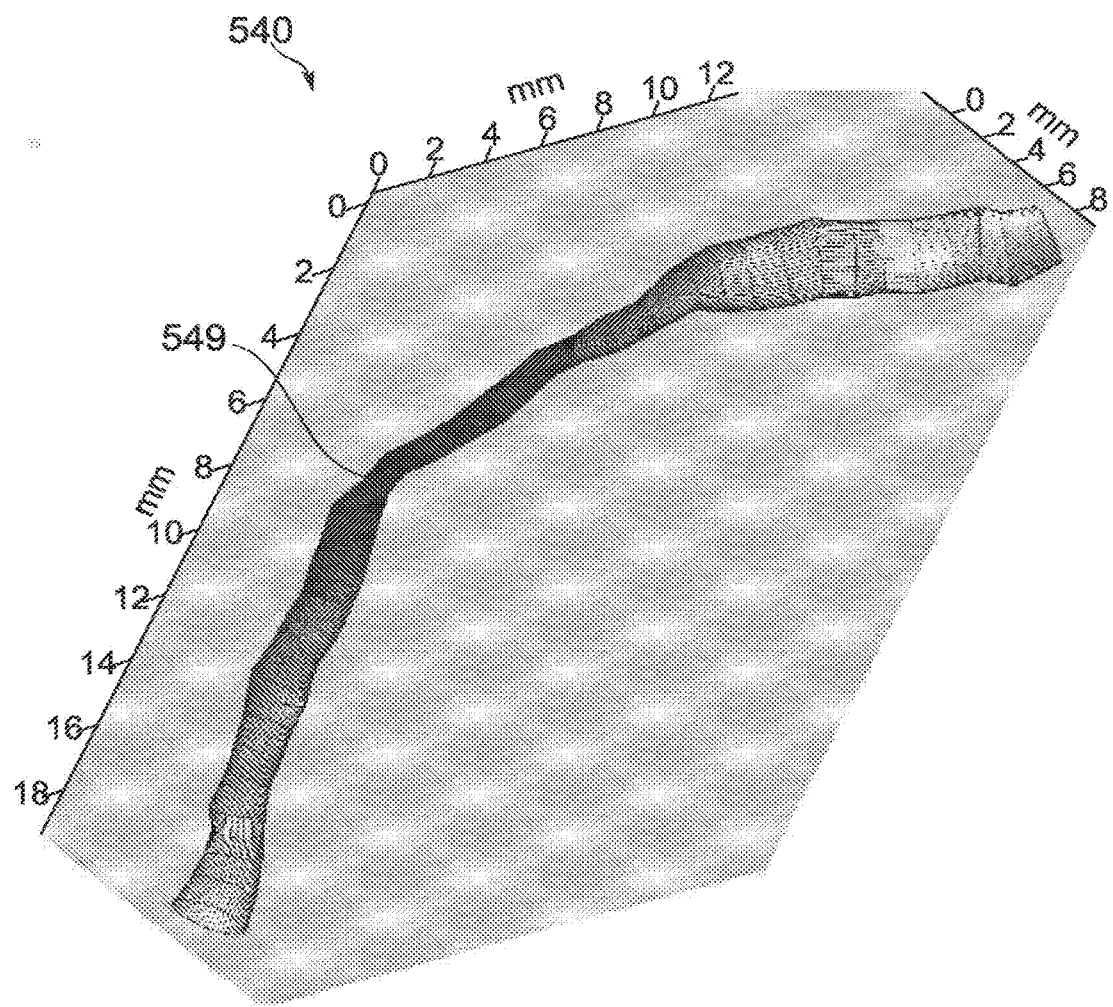
Figure 20A:
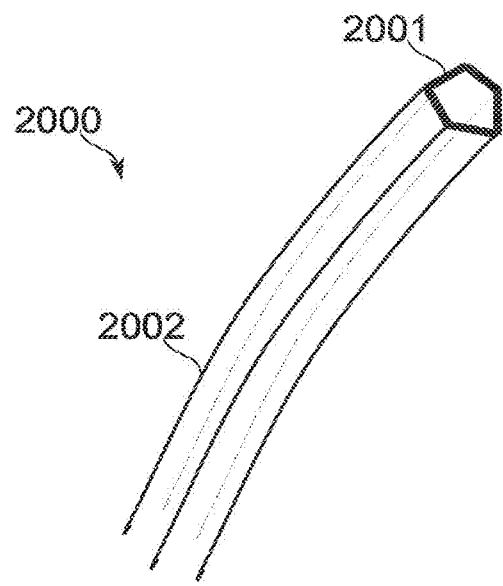
FIG. 20A shows a vascular segment, having a polygonal cross section, according to some exemplary embodiments of the invention.

In some embodiments of the invention, a vascular tree model is viewable as a 3-D model. The 3-D model is, for example, a 3-D disc model (such as shown in FIG. 5E), and/or a 3-D mesh model, or any other 3-D representation of the data. A 3-D view can be built, for example, by combination of the 3-D skeleton with corresponding 1-D graphs of vascular width. When vascular width is calculated across more than one cross-section of the vessel (for example, for more than one 2-D image), the width shown can be an average, a radially varying width, or any other width, chosen according to the requirements of the output's function. For example, reference is now made to FIG. 20A, which shows a vascular segment 2000, having a polygonal cross section 2001. Optionally, the dimensions of the various polygonal sides vary as a function of distance along the extent of segment body 2002. Optionally, the number of polygonal sides modeled varies along the extent of the segment.

In some embodiments, 1-D metric graphs for display are generated from the 1-D graphs 230 of the vascular tree model, for example as shown in FIG. 5B. A schematic view of a tree graph 240 can be generated for display, similar, for example, to that of FIG. 5C. The original images, too, remain available for display in some embodiments of the invention. In some embodiments, the various views of the representational modes of the vascular tree model are linked together in the viewing interface, for example, a computer screen or projection device. For example, a displayed 3-D model can serve as an anchoring metaphor for navigating the vasculature. Selection of a segment, for example, allows display of associated 1-D graph information, highlights a corresponding segment in a displayed tree graph and/or 2-D image, and/or allows selection for display of one or more 2-D images which comprise representations of the cross-section of the selected vessel.

Figure 20B:
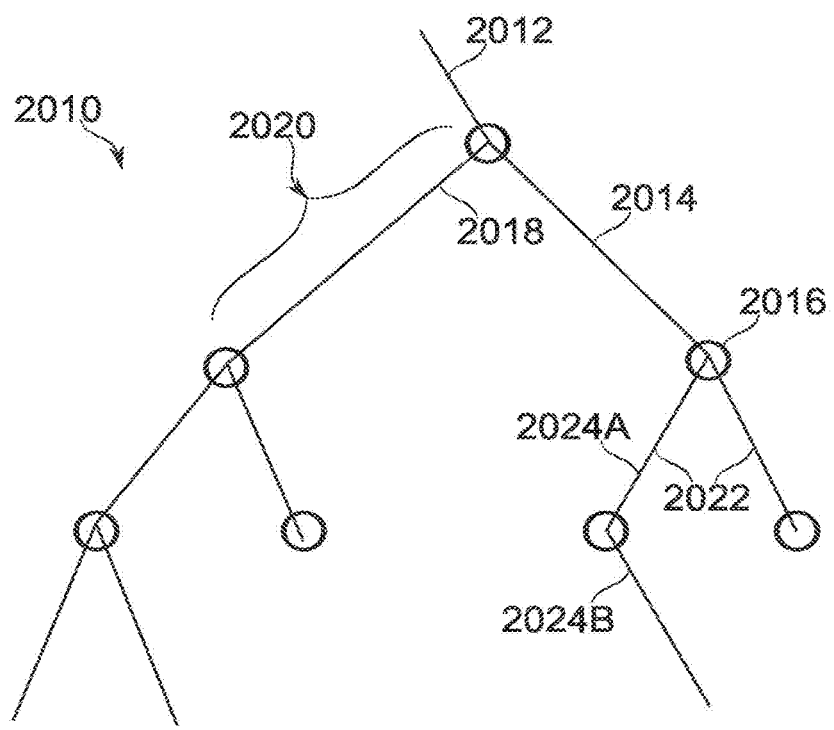
FIG. 20B shows elements of a vascular tree skeleton representation, according to some exemplary embodiments of the invention.

Reference is now made to FIG. 20B, which shows elements of a vascular tree skeleton representation 2010, according to some exemplary embodiments of the invention. In some embodiments, a vascular tree representation comprises a root or trunk 2012, which is a segment element having no "ancestor" elements, and for which every other connected segment element is a segment of the root segment's crown. In some embodiments, the other connected segment elements (for example, segment 2014) comprise branches of the vascular tree (each branch except the terminal branches themselves has a crown comprising its own branch segments). In some embodiments, branches split off at branch nodes 2016. Typically, branches are bifurcations; however trifurcations are also optionally modeled. In some embodiments, segment elements are associated at points 2018 along their extent with segment metric or characteristic data, for example, width, resistance (or resistivity), or another local characteristic of the vascular segment. In some embodiments, characteristics are associated with the segment as a whole; for example, the whole extent 2020 of a segment is associated with a resistance comprised of individual resistances along its length, with an average width, or another "segment-global" parameter or characteristic. In some embodiments of the invention, bifurcations branches 2022 share the relationship of connected branches and/or child branches of a parent branch 2014; in some embodiments, all branches in an established parent/child relationship comprise a network of connected branches. In some embodiments, a node breaks an unbranched segment region into a split map of two segment regions, for example, branch regions 2024A, 2024B. Branches, in some embodiments, provide a convenient anchor for other data, such as 2-D image data, 1-D representations (functions of length) of vascular segment characteristics, allowing such characteristics to be linked in the order of their vascular topology, potentially without the formation and/or use of a 3-D representation of the vascular tree as a whole. Additionally or alternatively, the skeleton representation comprises and/or is mapped to a 3-D representation of the vasculature—for example, each skeleton point is assigned a location in a 3-D space.

In some embodiments, an output module comprises the calculation of one or more additional metrics from the vascular tree model, and/or provision of one or more indexes based on vascular tree model metrics. For example, a fractional flow reserve (FFR) is calculated, in some embodiments, by comparison of a representation of the imaged vasculature which is virtually-updated to an astenotic (open) state with the vasculature as originally imaged. FFR index calculation is described, for example, in International Patent Application No. IL2014/050043 filed Jan. 15, 2014, by the Applicant, the contents of which are included herein by reference in their entirety. Additionally or alternatively, a vascular scoring algorithm is applied to the model in order to assess clinical situation, and provide assistance in selecting a treatment option. Automated vascular scoring is described, for example, in International Patent Application No. IL2013/050889 filed Oct. 24, 2013, by the Applicant, the contents of which are included herein by reference in their entirety.

In either case, the contents of the model are optionally updated according to the parameters calculated as part of index determination. Here and throughout the descriptions, it is to be understood that the described divisions between modules, while convenient for purposes of exposition, do not necessarily correspond to—and do not limit embodiments of the invention to—separation of function in implementation. Functions, methods, and structural details described are optionally comprised within any organizational structure of a system which embodies the invention. This includes aspects such as the sources of inputs, the destinations of outputs, and program design patterns. As illustrative examples, the distinction between output modules 130 and virtual updaters 101 is altered in some embodiments to allow: complete combination of the roles of each in a single module, transfer of functions described in connection with one module to the other module, and/or diversion or sharing of output described as provided from a virtual updater 101 to the model to an output module 130.

Exemplary Virtual Updates

Reference is now made to FIGS. 3A-3F, which illustrate virtual updater module embodiments operating to transform among a variety of model source and model destination representations, according to some exemplary embodiments of the invention.

FIGS. 3A-3F also serve as introductions to embodiments of virtual updaters for vascular stenosis regions which are described in relation to FIGS. 6-9 hereinbelow.

In some embodiments of the invention, the vascular tree model comprises mapping relationships among different encodings of the data. In some embodiments of the invention, input data (such as image data), and/or parameters of interest derived from the input data, are mapped to a plurality of positional frameworks. In some embodiments, 2-D image data, for example, are typically obtained together with x, y positions comprising pixel positions within an image frame. Additional mapping frameworks for data comprise, for example, spatial position in a 3-D space, position relative to position along a vessel segment, position within a tree of vessel segments relative to branch node points, position relative to a 3-D skeleton comprised of nodally-connected vessel segments, and/or another positional framework suited to the analysis of a parameter of interest. Optionally, the positional framework comprises a time-representing axis, used, for example, in the recording, extrapolation or interpolation of a time-varying parameter of interest.

While FIGS. 3A-3F are labeled and discussed in terms of stenosis-like modifications (widening and narrowing of vessels), it is to be understood that a virtual update can be to any desired vascular parameter of interest. Furthermore, a virtual update comprises, in some embodiments, the addition of a new parameter of interest to the model framework. A parameter of interest is, for example: vascular width, vascular resistivity to flow, a vascular wall characteristic such as and/or corresponding to roughness or elasticity, tortuosity, contrast density along the wall, or another vascular parameter. Vascular parameters, in some embodiments, are derived from the pixel intensity of features in vascular images. In some embodiments, one or more vascular parameters are derived from intravascularly-obtained measurements, such as measurements made using a sensor and/or radiation source (for example, sound, electrical, magnetic, electromagnetic, and/or nuclear) advanced through a blood vessel by means of a catheter.

Parameters of interest, in some embodiments, vary with time. Variability is over a relatively short term (millisecond or seconds) in some embodiments, for example, vascular width as a function of pulse phase and/or pulse pressure. In some embodiments, time variation is encoded over a longer term, for example, in order to compare vascular metrics obtained at and/or representing times separated by a period of days, weeks, months, or years. In some embodiments, measurements of a target parameter taken at different times reflect variation in a condition, for example, the presence or absence of a drug, recent exertion or rest state of a patient, or another condition. In such cases, the time scale separating conditions is typically on the order of seconds, minutes, or hours.

In some embodiments of the invention, "virtual" parameters are calculated as alterations to recorded parameters, and/or parameters inferred from recorded data. In some embodiments, an initial representation is used as a source of information from which a second, "virtual" representation is derived. FIGS. 3A-3F show a range of examples where the parameter of interest is a degree of stenosis in one or more vascular segments. Stenosis in turn is potentially represented based on vascular width, or, m particular, based on vascular width relative to some baseline condition.

It should be noted that an object of the descriptions relating to FIGS. 3A-3F is to illustrate in general how multiple cross-referenced representations of vascular data can be used to virtually update one another, with the input and output being chosen according to need and/or convenience of processing. This approach can be contrasted with a model and use thereof where a full 3-D reconstruction of the vascular tree is the central data object. In particular, it contrasts with a method which generates most modifications to and/or manipulations of the data based on the 3-D reconstructed version of the vascular tree, or extracted and/or reduced portions thereof.

The relevance of the difference is seen, for example, by considering that each transforming step in an image processing chain potentially introduces error due, for example, to approximations and/or simplifying assumptions. A 3-D vascular model acquired using present imaging technology is not a snapshot, and comprises assumptions about, for example, heart motion, body motion due to breathing, and accuracy of calibration. Where data is sampled incompletely or irregularly, the 3-D model may comprise interpolations, potentially without explicit recognition of this in the representation which is made available. Furthermore, calculations on 3-D models are potentially more intensive than calculations on lower-dimensional representation. Even though a 1-D model, for example, can be generated from a 3-D model—this might be attempted to allow real-time manipulation of the model—it will continue to reflect any distortions due to errors in the assumptions that generated the 3-D model in the first place.

On the other hand, the approach of using a 3-D skeleton largely to link various 2-D views of the heart data allows 1-D modeling to be based on uniformly-potentially simultaneously-sampled pixels, for example, a single image as obtained using an X-ray angiography imaging machine. Potentially, the original 2-D view itself is directly useful for calculations in real time, without introducing issues of distortion and/or aliasing that might arise from virtual sectioning of a 3-D reconstruction.

While embodiments of the present invention are capable of producing full 3-D reconstructions of a vascular tree, it is explicitly recognized that each of several different data representations and/or positional frameworks for data has its own strengths relative to a 3-D representation—for example, in terms of precision, accuracy, computational demands, and ease of understanding. In some embodiments of the invention, full 3-D representation (such as a representation comprising a 3-D mesh of the overall vascular tree wall) is bypassed altogether. In some embodiments, 3-D representation as such is primarily used to provide a common framework relating non-3-D representations which serve as the direct basis of computations for determining one or more vascular metrics. It is even possible, in some embodiments, that a 3-D representation used in generating a vascular tree is afterwards discarded, while the relational information established through its use is retained for subsequent operations.

In some embodiments, the updated representation becomes part of the vascular model, for example by means of indexing to one or more of the model's positioning schemes. The returning arrows of FIGS. 3A-3F indicate such updating in some embodiments of the invention. It should be understood that the updating can be either by replacing an original representation, or by adding a layer of representation to the model (for example, the model can represent two or more different times and/or conditions). In some embodiments, an updated representation is propagated to other representational modes. For example, an updated 1-D representation of vascular segment width is optionally propagated to a virtually constructed 2-D image where pixel opacities representing vascular wall positions are changed to match the characteristics of the 1-D representation.

Figure 3A:
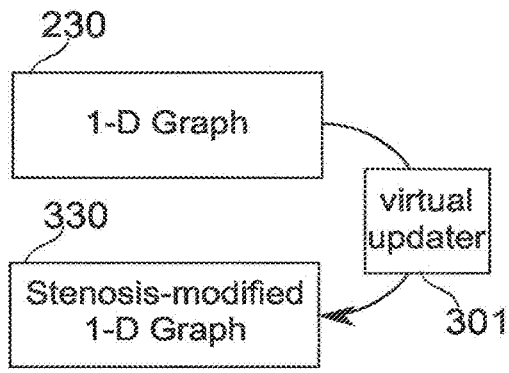
FIGS. 3A-3F illustrate virtual updater module implementations operating to transform among a variety of model source and model destination representations, according to some exemplary embodiments of the invention.
Figure 3B:
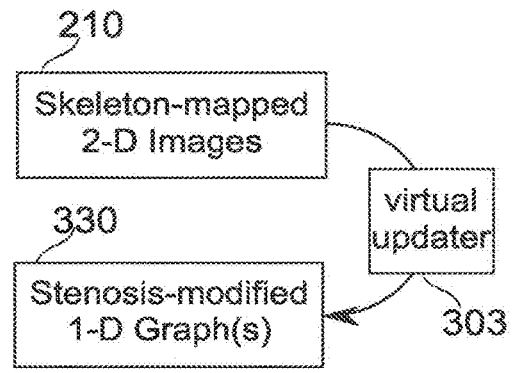
Figure 3C:
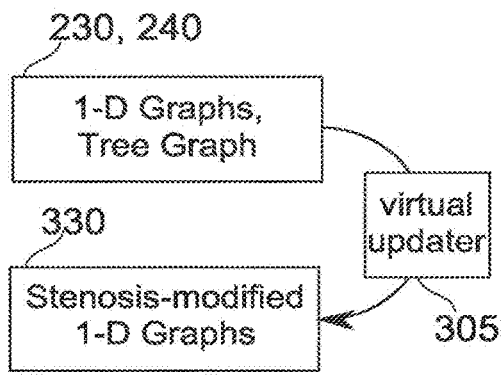
Figure 3D:
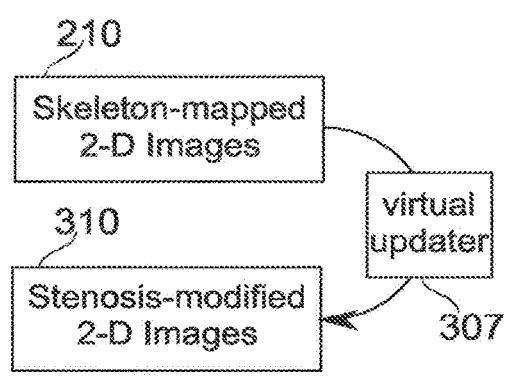
Figure 3E:
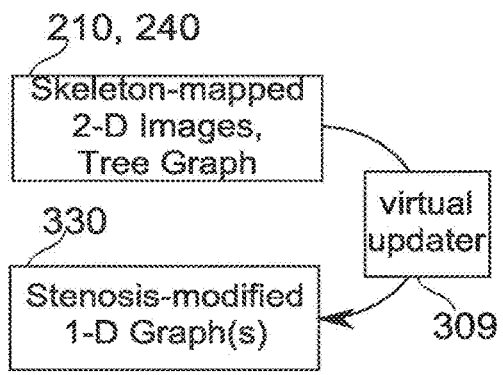
Figure 3F:
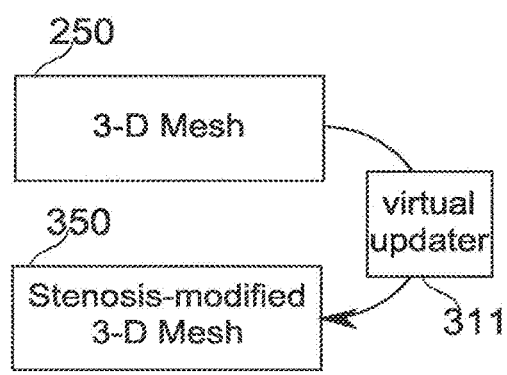

Thus, for example, an input 1-D graph 230 can represent vascular width as a function of distance along the vessel (FIG. 3A). A virtual updater 301, in some embodiments, operates on this function to produce a virtual vascular width graph 330.

In some embodiments, a stenosis-opening 1-D graph, for example, represents a pre-stenosis vascular state determined by using non-stenosed vascular portions of the input graph 230 to interpolate through a stenosed region. This is described, for example, in relation to FIGS. 7A-7B, hereinbelow.

Additionally or alternatively, the expected deployed diameter and length of an implantable stent is used to adjust the input 1-D graph 230 and produce a stenosis-modified graph 330. Alternatively, the 1-D graph 230 is time-progressed, for example, by extrapolation from one, two, or more previously recorded vascular states, in order to project a future, more highly stenosed 1-D graph model 330 of the blood vessel. Optionally, extrapolation comprises use of a standard curve used to estimate development of a lesion over time based on one or more reference measurements of occlusion state.

In some embodiments, a virtual updater operates to convert among two or more different positional frameworks in calculating a stenosis modification. Thus, for example, in FIG. 3B, input to a virtual updater 303 of vascular skeleton-mapped 2-D images 210 is used, in some embodiments, to produce a stenosis-modified 1-D graph 330 directly, for example, as described in relation to FIG. 6, hereinbelow. Additionally or alternatively (FIG. 3D), one or more source 2-D images 210 is converted by a virtual updater 307 directly to a stenosis-modified 2-D image 310.

In the case of another embodiment of a virtual updater 305 (FIG. 3C), information from a vascular segment's own 1-D graph 230 is optionally supplemented by information from neighboring segments, encoded in a tree graph 240, to produce a stenosis-modified 1-D graph 330. This is described, for example, in relation to FIG. 9, hereinbelow.

Vascular width at vascular branch points is potentially difficult to calculate due to the absence of an unambiguous wall across the branch location, and/or due to a lack of one or more segment-end anchor widths to interpolate from In some embodiments of a virtual updater 309 (FIG. 3£), the relationship of segments known from a segment tree graph 240 is used to link together portions of vascular skeleton-mapped 2-D images, such that interpolation across the branch can be made from the 2-D image data 210 available. The result, in some embodiments, allows determination of a 1-D width graph for all or part of one or more vascular segments in which stenosis narrowings are largely removed.

In some embodiments of the invention (FIG. 3F), a 3-D mesh 250 is "part of the model", in the sense that it is a direct object of operations which determine a stenosis modification, and/or is modified by a virtual updater 311 to a new 3-D mesh 350 which is integrated into the reciprocal positional relationships represented in the model. Although this has potential drawbacks for real-time tasks, there is a potential advantage in fidelity, for example, in cases where a lesion is radially asymmetric such that its characteristics are not well-represented in cross-section.

Stenosis Determination

Stenosis Determination—Image-Based

Figure 6:
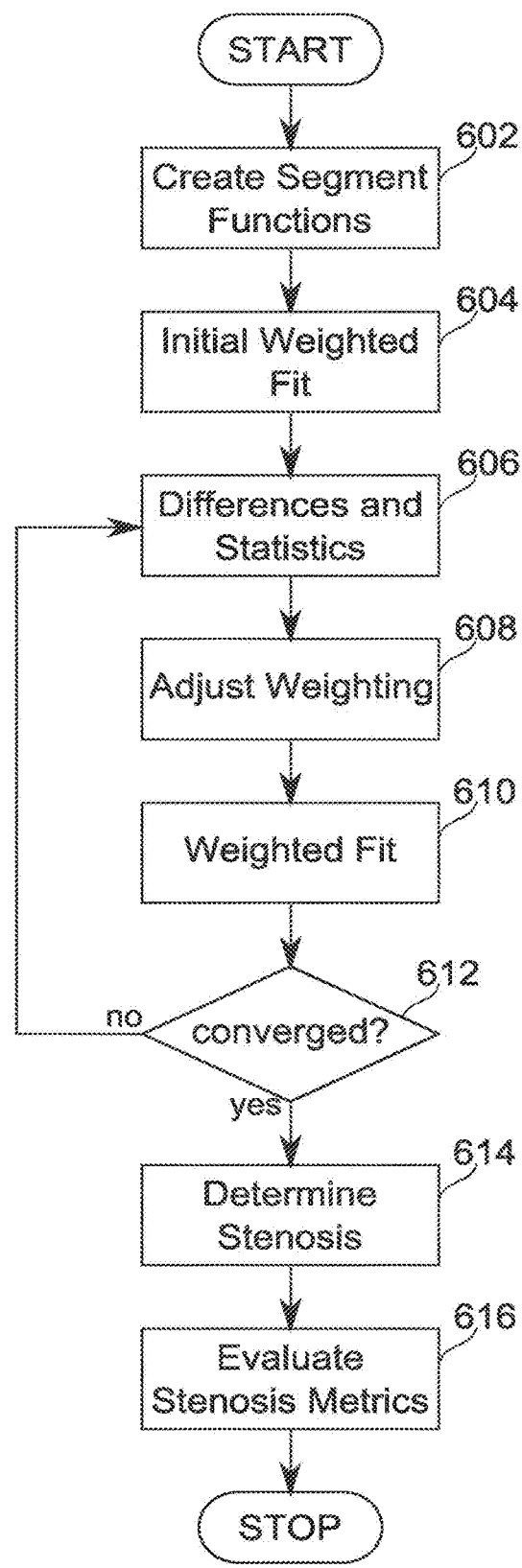
FIG. 6 is a simplified flowchart of a method of determining the presence and/or associated measurements of stenotic lesions, according to some exemplary embodiments of the invention.

Reference is now made to FIG. 6, which is a simplified flowchart of a method of determining the presence and/or associated measurements of stenotic lesions, according to some exemplary embodiments of the invention.

In some embodiments of the invention, stenosis in the imaged anatomy is determined relative to a "virtually revascularized" model of the anatomy. The virtual revascularization, in some embodiments, comprises determination of a vascular tree model which removes narrowings and/or other obstructions which are determined to comprise anatomical changes that are likely due to vascular pathology.

At block 602, the flowchart starts, and each vessel segment is converted to a one-dimensional function $f(s)$ of diameter vs. distance, and/or extracted in this form from a vascular tree model. Optionally, the function yields vessel radius or another metric comprising information about the vessel lumen cross-section, such as diameter or area. In some embodiments, distance is obtained from the Euclidean distance formula, integrated at points along the vessel segment, for example:

$$s = \int \sqrt{dx^2 + dy^2 + dz^2}$$

where s is the integrated distance at a point along the vessel segment. The integral notation and other uses of "integration" herein should be understood as potentially implemented by an approximation summing finite elements and/or other by another approximation appropriate for discrete image pixel (2-D) or voxel (3-D) samples. Additionally or alternatively, integration is potentially over a continuous, image-data derived function, for example one obtained by spline fitting and/or interpolation.

In some embodiments, the diameter of the vessel at a given point is taken from a diameter measured in a representative 2-D image of the vessel. In some embodiments, the diameter comprises an average of the diameters measured from a plurality of 2-D projections visualizing that point (for example, all available 2-D images). Optionally, the diameter is instead calculated based on the open area of a 3-D model of the vessel, approximating the vessel lumen cross-section as circular. Optionally, the lumen cross-section area is used directly. Alternatively or additionally, radius is used. In the discussion that follows, it is to be understood that "diameter" is replaceable by another metric of lumen openness, with the method changed as necessary.

In some embodiments of the invention, an iterative process of virtual revascularization now begins for each segment (looping over each segment is not shown).

At block 604, in some embodiments, an initial reference diameter is chosen to comprise a statistical fit (for example by a linear, least mean squares method, optionally modified by a weighting function) to vessel diameter along the vessel segment length. In some embodiments, points near either end of the segment are weighted more than other segments. It should be noted that in some embodiments, determination of an unstenosed diameter at segment ends, for example, near a bifurcation, is carried out by a module specialized for bifurcation analysis, for example, as described hereinbelow in relation to FIGS. 8A-8B. It should also be noted that in some embodiments, refinement of a determination of an unstenosed diameter for one or more segments is determined with reference to one or more constraints applied in consideration of a plurality of segments, for example, as described hereinbelow in relation to FIG. 9. Optionally, the point weightings are adjusted so that best-fit deviations from wider (potentially less-diseased) points along the segment are weighted as more important than deviations from narrower points. This provides a potential advantage by allowing less-diseased regions of the vessel to dominate the determination of the virtually revascularized vessel width. The weighting determinations are adjusted during subsequent revascularization operations. Optionally, the weighting function scaling is adjusted according to the distribution of widths in the selected segment. Optionally, the weighting function comprises a cutoff threshold, for example, such that vascular regions less than 70%, 60%, 50%, or another larger, smaller, or intermediate fraction of another vascular width are weighted as irrelevant to the true vascular width. Optionally, the weighting function comprises a graded reduction in weight away from a target width. Optionally, the weighting function reduces weight either larger or smaller than a target width; or only smaller than a target width. Optionally, the weighting function is adjusted by assessment of uncertainties due, for example, to the proximity of a branch region. Optionally, the weighting function is adjusted to have a larger target size at either end of the vessel, for example, to account for normal vascular narrowing along its length.

At block 606, in some embodiments, differences between fit and measured points are determined, and statistics (for example, mean, standard deviation) are calculated based on the determined differences.

At block 608, in some embodiments, weighting adjustments are made, such that certain outliers from the linear fit are reduced in weight. The outliers are, for example, points which have statistically meaningful differences from the fit. Meaningful differences include, for example, being more than two standard deviations away from the best-fit line compared to the population of diameters overall.

At block 610, in some embodiments, the best fit (typically linear) is redetermined. It should be noted that embodiments of the invention are not limited to a linear fit, but linearity is a convenient model for capturing the observation that vessels decrease in diameter more-or-less monotonically along their length away from the end proximal to the heart.

At block 612, in some embodiments, a test is performed to see if the best fit line has converged within some limit of stability. If not, processing continues with another fitting round at block 606. If the best fit has converged to a stable solution, processing continues with block 614.

At block 614, in some embodiments, the best fit function/(s) is used together with the original data function $f(s)$ to determine stenosis, for example:

$$\text{stenosis} = 100 * \left(1 - \frac{f(s)}{\tilde{f}(s)}\right)$$

At block 616, the segment function is optionally evaluated for additional metrics related to lesion depth, length, and position. For example, an output of the process, in some embodiments, comprises pairs of values s1, s2, such that for $s_1 \leq s < s_2$, s is within a stenotic lesion. The flowchart then ends.

Stenosis Determination—1-D Graph-Based

Figure 7A:
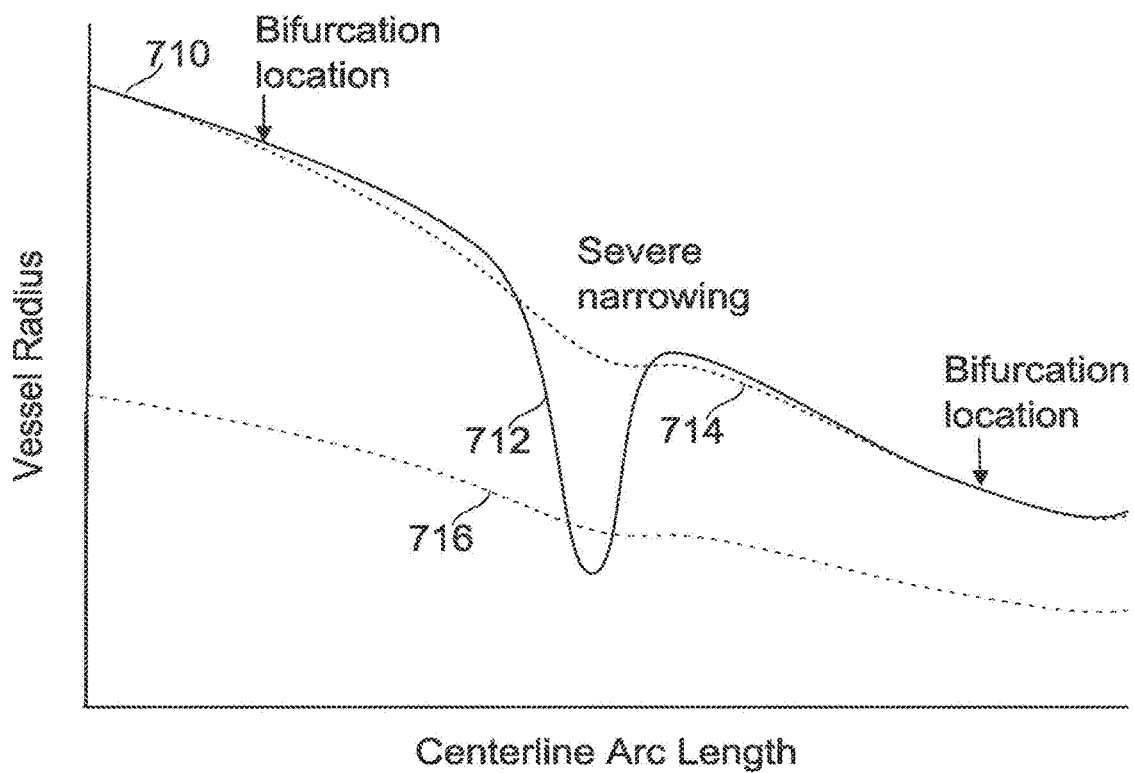
FIGS. 7A-7B schematically illustrate an example of a stenotic determination, according to some exemplary embodiments of the invention.
Figure 7B:
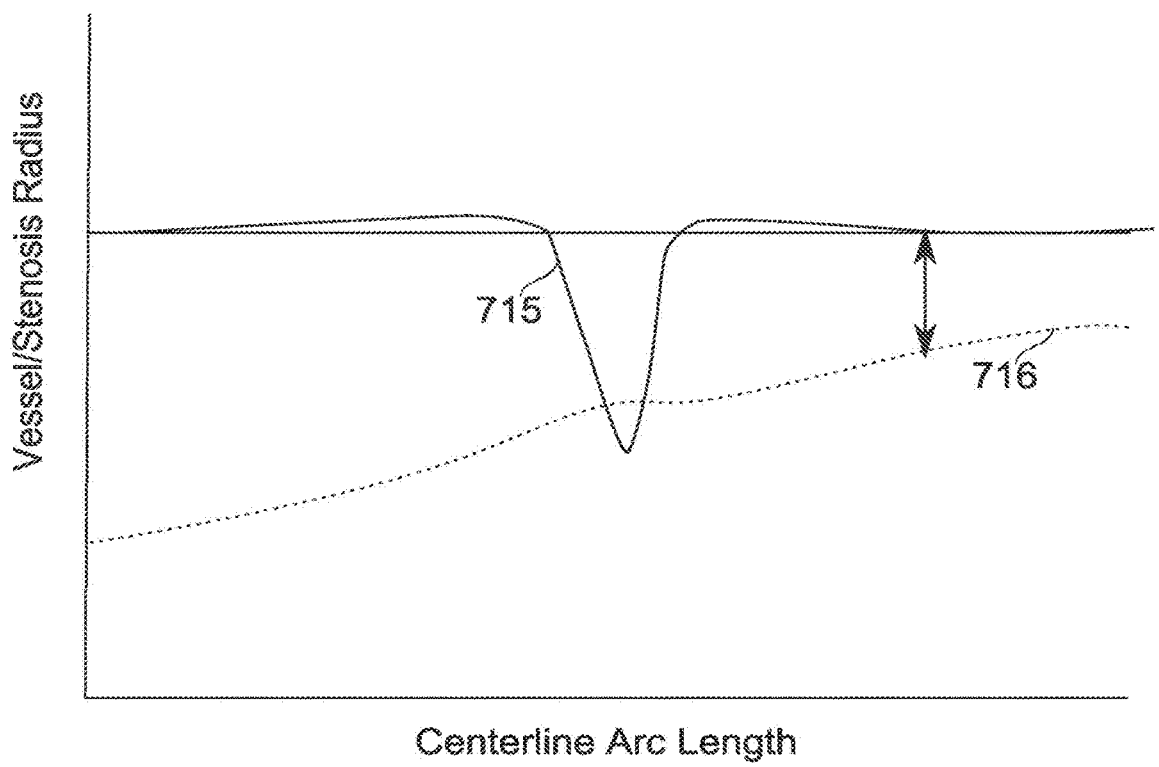

Reference is now made to FIGS. 7A-7B, which schematically illustrate an example of a stenotic determination, according to some exemplary embodiments of the invention.

The plot 710 in FIG. 7A shows radius (Vessel Radius) along a vessel segment (Centerline Arc Length). In some embodiments of the invention, measurement of stenosis is extracted from such a one-dimensional function $r=f(s)$, where r is the vessel radius, and s is the arc-length (vascular segment length).

In some embodiments of the invention, for example, a severe stenosis 712 is automatically identified by means of a high-pass filter. Plot 715 is the high-pass filter result. Subtracting the plot 715 from plot 710 obtains plot 714, which approximates the un-stenosed vessel width.

Further calculations based on this determination are performed in some embodiments, for example, in the context of generating a vascular state score index. Plot 716 represents the half-width of plot 715, being, for some embodiments of a vascular score, the threshold between a scored and an unscored stenosis. Inverted and superimposed on plot 715, a sufficiently severe stenosis reveals itself where the plot 715 crosses inverted plot 716. Additionally or alternatively, a very positive and/or negative slope along a portion of plot 715 indicates a region of abrupt change which potentially indicates a stenotic lesion.

In some embodiments of the invention, a lesion length is determined, for example by a metric such as width at a percentage occlusion relative to the maximum occlusion. In some embodiments, this percentage is 5%, 10%, 20%, or another percentage. In some embodiments, a lesion length is determined by a slope inward from the vascular wall above a threshold, for example, a change of 1 part in 3 (occlusion depth-to-length), 1 part in 5, 1 part in 10, or another larger, smaller, or intermediate slope. In some embodiments, a second or higher slope derivative is the basis of a total lesion length determination.

Stenosis Determination—Furcation Locations

Figure 8A:
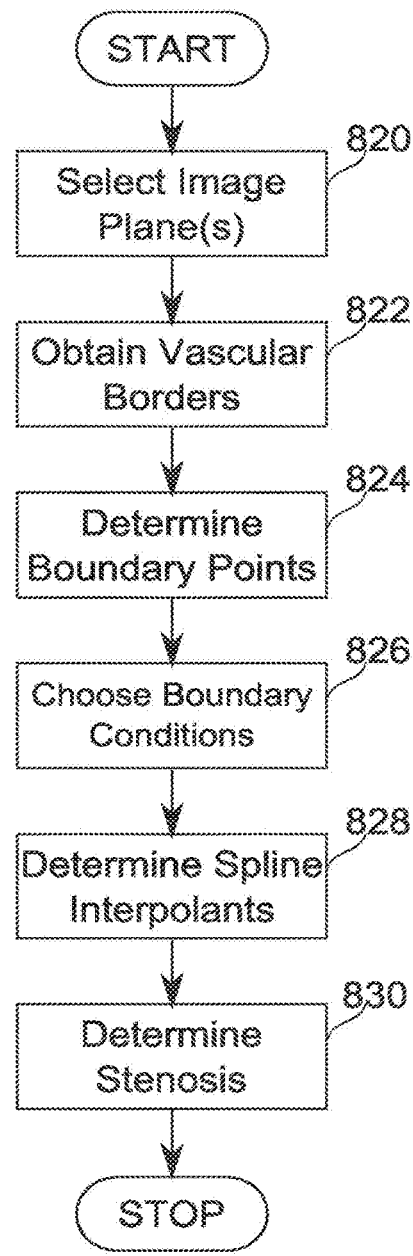
FIG. 8A is a simplified flowchart of a method of determining the presence and/or associated measurements of stenotic lesions in the region of a vessel bifurcation, according to some exemplary embodiments of the invention.
Figure 8B:
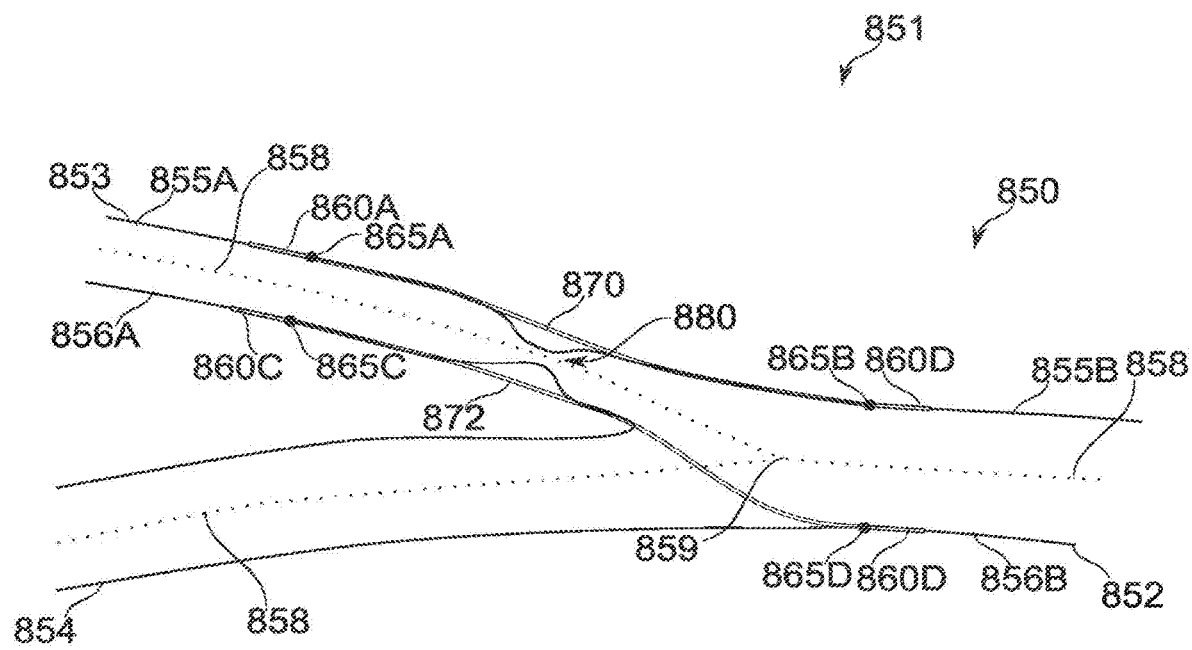
FIG. 8B schematically illustrates elements used in the method of FIG. 8A, according to some exemplary embodiments of the invention.

Reference is now made to FIG. 8A, which is a simplified flowchart of a method of determining the presence and/or associated measurements of stenotic lesions in the region of a vessel bifurcation, according to some exemplary embodiments of the invention. Reference is also made to FIG. 8B, which schematically illustrates elements used in the method of FIG. 8A, according to some exemplary embodiments of the invention.

In some embodiments of the invention, diameters determined along a blood vessel segment are potentially ill-defined at a bifurcation (or trifurcation) where abrupt changes in diameter occur, or where the definition of a diameter, radius, or cross-sectional area is indeterminate. In some embodiments, a procedure is implemented whereby diameters at such boundaries are defined more clearly.

The flowchart begins, and at block 820, in some embodiments, at least one image plane 851 passing through a bifurcation 850 is selected as a reference plane for analysis. In some embodiments, every image plane in which a bifurcation is identified as appearing is selected during some iteration of the method. In some embodiments of the invention, determination of these image planes in turn, and/or of the region of the planes in which the bifurcation appears, proceeds from the relationship between image planes and a three-dimensionally reconstructed vascular tree skeleton.

In some embodiments, the image section is manually selected. In some embodiments, the image plane is selected to be a plane which includes vessel center points 858 of at least two vessels at a determined distance from the vessel (for example, 1 mm, 2 mm, 3 mm or a greater or larger distance), and a point 859 near the center of the region of bifurcation. Optionally a different plane is selected for each pair of trunk 852 and branch vessels 853, 854 (trunk and a first branch, trunk and a second branch). The method is described herein below with respect to one plane of analysis selected for one branch point vascular segment pair (a trunk 852 and a branch 853), but it is to be understood that the analysis is optionally carried out on two more vascular segment pairs at a given segment junction. It is also to be understood that unstenosed diameter within more than one plane is optionally determined, and results from this plurality of determinations composed into one or more metrics describing unstenosed vascular morphology. For example, in some embodiments, a plurality of planes is selected, and an average or other statistically determined unstenosed vessel diameter selected from the set of planes analyzed. In some embodiments, unstenosed vessel widths determined in a variety of directions corresponding to different image planes are composed into an approximation of the shape of the vessel lumen circumference at different locations along its length.

At block 822, in some embodiments, for each vessel segment in a pair (for example a pair comprising a trunk vessel 852 and a branch vessel 853), data sets describing each of two vessel borders $(x_b, y_b)$ falling within a selected image plane are determined. The border data sets 855A, 855B, 856A, 856B are, for example, determined by the locations along the vessel segment length which represent a transition from low contrast to high contrast. The transition point is determined, for example, by a threshold, a peak rate of contrast change, by a simple edge detection convolution, by a Frangi filter, or another appropriate boundary-finding method. For convenience of exposition, the vessel border data sets $(x_b, y_b)$ are referred to hereinbelow as the "left" border 856A-856B and the "right" border 855A-855B, it being understood that the designation of left and right in this context is potentially arbitrary.

At block 824, in some embodiments, for each of the trunk 852 and branch 853 segments chosen and for each border, a boundary point 865A-865D away from the bifurcation is chosen as a reference and/or spline interpolant termination point. The reference point may be considered as a trusted and/or anchor point, far enough from the point of a potentially lesioned bifurcation that it provides an unstenosed reference diameter for the vessel at that point. In some embodiments, the distance chosen is, for example, 1-2 mm, 2-4 mm, 1-5 mm, or another larger or smaller distance from the core of the bifurcation. In some embodiments, the distance is chosen as a function of a previously estimated vascular width, for example, 2, 3, 4 or a greater or smaller multiple of the previously estimated vascular width.

At block 826, in some embodiments, boundary conditions 860A-860D are determined at each of the points comprising a reference point location. In some embodiments, a first derivative up to a derivative of order n is determined, for example by examination of border point locations from 1 to n data nodes away from the selected node point. The result, in some embodiments, is a set of four boundary conditions-two for the left wall, and two for the right; one of each wall pair being from the trunk vessel segment, and one from the branch vessel segment.

At block 828, in some embodiments, a spline interpolant 870, 872 is determined for each of the left and right walls which runs between the boundary conditions determined for each wall. Each such spline interpolant may be considered as an "unstenosed" border data set $(x_i, y_i)$ corresponding in portions to one or the other of the original image border data sets $(x_b, y_b)$ for one wall of both the trunk and branch vessel segments, and in a central portion to the region of the bifurcation. Additionally or alternatively, the left- and right-wall spline interpolants may be considered as bounding the lumen of the open or unstenosed vascular segment through the region of bifurcation. In some embodiments, the interpolants are optimized (while preserving the boundary conditions) to maximize contrast differences across the surfaces of the interpolants. This corresponds, ideally, to adjusting the interpolant diameter to the diameter of the vascular wall, and to adjusting the interpolant center position to the center of the blood vessel. Contrast is determined, in some embodiments, by a simple edge detector, by the output of a Frangi filter, or by another means of edge detection known in the art. In some embodiments, positions within the core of the bifurcation are ignored for purposes of fit determination. In some embodiments, constraints on maximum curvature are included, to prevent bulges from forming during the optimization procedure. In some embodiments, regions where there is insufficient contrast available locally, for example, where a spline crosses the opening into a branch, are neglected in the optimization calculation.

At block 830, in some embodiments, the lumen bounded by the unstenosed border data sets $(x_i, y_i)$ is compared to the lumen bounded by the corresponding data-derived border data sets $(x_b, y_b)$, to determine an absolute and/or relative degree of stenosis at a region 880 in the lumen comprised within the region of bifurcation. Optionally, the comparison is made, for example, after conversion of relative border locations to diameters, radii, areas, or another metric as a function of position along the vascular segment length and/or away from the region of bifurcation. Optionally, the two-dimensionally determined model is referred back to a three-dimensional model by making reference to 2-D to 3-D mappings determined during a phase of 3-D vascular tree reconstruction. Optionally, the degree of stenosis is analyzed as for stenotic regions in FIG. 6 and/or FIGS. 7A-7B. The flowchart ends.

Identification of Homologous Data Representations

Figure 17A:
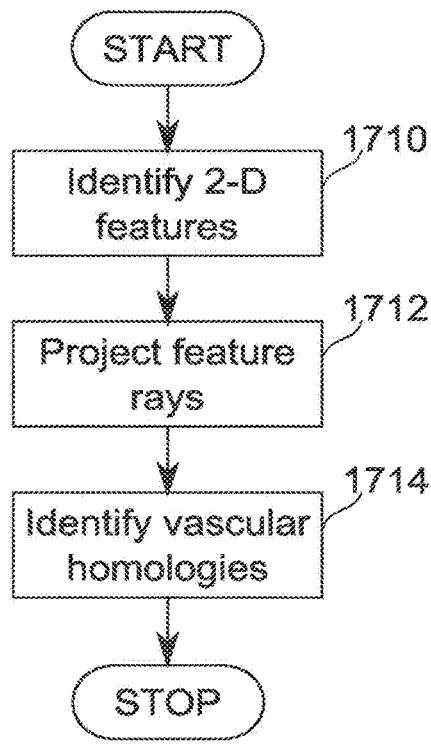
FIGS. 17A-17C are flowcharts schematically representing determinations of common representation relationships among 2-D data sets (images), according to some exemplary embodiments of the invention.
Figure 17B:
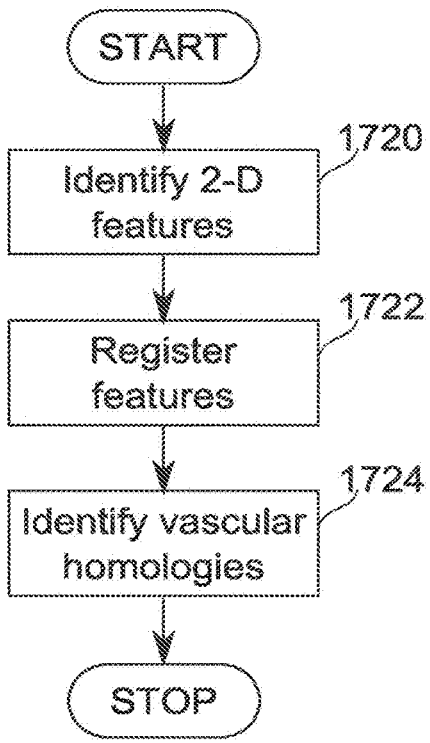
Figure 17C:
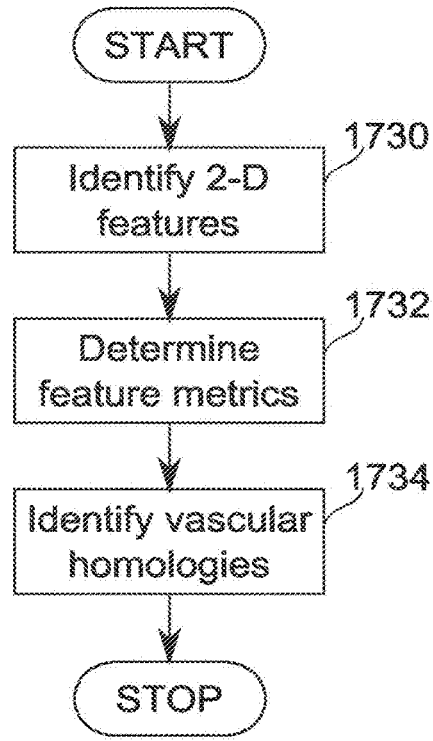

Reference is now made to FIGS. 17A-17C, which are flowcharts schematically representing determinations of common representation relationships among 2-D data sets (images), according to some exemplary embodiments of the invention.

In some embodiments of the invention, a task in the calculation of vascular anatomy and/or functional parameters is the determination of homologies among portions of the data (for example, 2-D image data) which have been acquired from a vasculature for analysis. FIGS. 17A-17C outline exemplary methods of establishing such homologies. In some embodiments, 2-D data sets comprising inputs are 2-D angiography images, for example, of the coronary arteries of a heart. In some embodiments, the images are acquired by X-ray projection imaging of a heart after injection of a radio-opaque contrast agent.

FIG. 17A describes a 3-D projection-type method of establishing by comparison of global characteristics such as general position that two 2-D image regions represent a common vascular structure.

At block 1710, in some embodiments, 2-D features of the vascular images are identified. In some embodiments, the 2-D features identified comprise vascular segments. Preferably, the vascular segments are the vascular segments of specific interest for the metric. The parts of the vascular segments identified are, for example, vascular centerlines, from vascular walls, vascular branch points, and/or any other imaged vascular feature. Vascular segments are identified from the 2-D image, for example, by contrast differences, edge detection and/or another method of vascular tracing.

It is a potential advantage to perform common representation (homology) identification directly from the vascular features of interest, as this avoids an intermediate step of mapping. However, in some embodiments, non-vascular features are identified, and/or features are identified on the basis of contrast, without special reference to their vascularity. In some embodiments, a "feature" is, for example, any configuration of pixel values which characterizable such that it is statistically or otherwise likely to be uncommon in appearance. Optionally, the characterization is relatively invariant to projection angle. For example, the characterization remains about the same (within, for example, 10%, 20%, or a greater or lesser fraction of some value), for variations of projection angle of about 10°, 20°, 30°, 45°, 60°, 90°, or another greater, lesser, or intermediate change of projection angle.

At block 1712, in some embodiments, back-projection of rays from the vascular segments (and/or other features) from the image plane (the plane of projection) toward the projection source is performed.

At block 1714, in some embodiments, vascular homologies are identified. In general, coronary vascular segments fan out over the surface of the heart, such that where rays from two different images of the same vascular segments (most closely) converge, they can be considered to intersect the same vascular segment-thus establishing their homology as representing a common object (a segment). It should be noted that exact intersection is not required for this, since main vascular segments themselves are in general well separated from one another over the heart's surface. The closest match is thus very likely to identify the correct matching.

In regions where segments approach each other to connect (at branch points, for example), potential ambiguity is resolved if necessary, for example, by following along the extent of the feature to regions where separation is clearer. Potential ambiguities at crossing points, if they occur, are resolved, for example, by noting vascular orientation, width, or other criteria of continuity.

In some embodiments, homology groups are bounded, for example, by vascular branch points; additionally or alternatively, other homology group boundaries are selected, such as "percentage along the vessel", break points at or near regions of stenosis, or another criterion. In some embodiments, homology groups are defined as potentially incompletely (or over-completely) overlapping regions; for example, regions are mapped to one another as comprising at least some threshold percentage of each others' vascular segment length, where the percentage is, for example, 80%, 90%, 95%, 100%, or another greater, smaller or intermediate value. This is a potential advantage for handling image regions, for example, where a vascular segment is long enough to characterize it, but is partially cut off on one end.

In embodiments where the features originally back-projected are non-vascular (or not previously determined to be vascular), determination of homology optionally includes a further operation—for example, two vascular segment projections which are closest in their respective projections to feature data which are themselves determined to be homologous, are also considered homologous.

FIG. 17B describes an image registration-type method of establishing vascular homologies.

At block 1720, in some embodiments, 2-D features are identified, for example as described in relation to FIG. 17A. In some embodiments, features preferably identified as useful have a uniquely identifiable orientation, and/or lack self-similarity over small translations (for example, vascular boundaries at branch points, sharp vascular curves, and/or background features comprising at least two non-parallel feature boundaries within a sufficiently small region). Preferably, vascular features are identified as for FIG. 17A, but these are potentially distinct from features use for image registration.

At block 1722, in some embodiments, 2-D images are registered to one another based on feature similarities (for example, of contrast, size, and/or orientation) among their features. Optionally, registration comprises transformation of one image through the parameters of a matrix or other transforming element into the 2-D coordinate system of the other image (or of both to a third coordinate system).

Optionally, the transformation element includes one or more parameters describing non-rigid warping of one or both images. Optionally, the transformation is chosen to minimize differences of distance or other dissimilarity (such as scale or orientation) among features having similar properties, and/or among features as such, considered as patterns of landmarks distributed over the images.

Between two images having only moderately different projection angles, such a 2-D only registration scheme potentially allows identification of homologous features without the use of 3-D back projection. For example, matched images are taken from angles within 10°, 15°, 20°, 25°, or another larger, smaller, or intermediate angle. In general, the larger the angle, the more approximate the match is expected to be. However, the tendency of the cardiac vessels to distribute over a surface potentially allows the approximation to be close enough for matching identification.

Optionally, images are sub-divided into smaller regions during registration, such that vessels extending through each registration sub-region potentially better approximate extension through a planar region (rather than a general surface, such as a heart surface, which is curved). This provides a potential advantage for reducing distortion of features outside regions of best mapping.

At block 1724, in some embodiments, vascular homologies are identified. As for 3-D back-projection in block 1714, the closest (in transformed position) vascular features are optionally assigned to the same homology group. Optionally, similarity criteria are set for homology to avoid matching as homologous segments which spuriously overlap after application of the registration transformations. The similarity criteria may comprise criteria of relative and/or absolute length, width, orientation, contrast, or another similarity criterion.

In some embodiments, homologies between more widely separate angles are determined by homology matching transitively through intermediate angles.

FIG. 17C describes a feature metric-type method of establishing vascular homologies.

At block 1730, in some embodiments, 2-D features are identified, for example as described in relation to FIG. 17A. In this method, the identified features are vascular segments, as it is aspects of the segments themselves which are to be compared in determining homologies. Optionally, an aspect of the features identified is the larger vascular tree which the segments make up—for example, the topology of connections among vessels of the vascular tree.

At block 1732, in some embodiments, vascular feature metrics are determined. Features identified are chosen to serve as elements of the identification template for vascular homology. For example, vascular width, for a round-cross section vessel lumen, is assumed to be invariant as a function of projection angle. Vascular width as a function of (relative) distance along a vessel potentially comprises some variability, since a vessel can be curved to show longer in projection at some regions than at others, but is generally expected to be similar within some threshold for sufficiently short sections of homologous vessels, particularly at segment endpoints. In some embodiments, branching angles at vascular bifurcations are measured. It is to be understood that although to some degree such rules are heuristic (and thus subject to exceptions), it is potentially sufficient for as little as one segment homology match to occur with certainty, in order to identify homologies among vascular segments to which they connect.

At block 1734, in some embodiments, vascular homologies are determined. For images taken at relatively close angles, similarities among metrics such as branch length and branch angle (for the same vascular feature to which homology is to be established) are expected to be relatively high (low difference of length/angle size). Optionally, transitive homologies are used, for example, as described in relation to FIG. 17B. In some embodiments, homology is determined by fitting characteristics observed from 2-D images to a particular position within the branch ordering of the vascular tree.

It should be understood that the above three methods, or another method of homology identification, can be used either separately, or in any suitable combination. For example, both 3-D back-projection and feature metric identification are applicable independently as cross-checks of one another. Additionally or alternatively, one method provides candidates for the other to select among. For example, where 3-D back-projection based on "nearest ray approach" identifies two vascular segments (for example, parallel segments) as potential homology candidates, comparison of further vascular segment metrics such as length, orientation, and/or estimated width is used in addition to select the best homology candidate.

In embodiments for which an at least partial 2-D vascular tree structure is available (for example, by analysis of 2-D centerlines), the unambiguous identification of homology between any two vascular segment projections in two different 2-D images potentially allows identification of the homologous relationships of every other (vascular tree-connected) vascular segment projection common to those two images. In some embodiments, this is used as a check on consistency; in some embodiments, it is relied on for some or most homology determinations. It should be understood as well that the number of vascular segments which need to be identified is not necessarily all segments visible. For example, for some methods of measuring FFR, it is sufficient to have segment identifications of any stenotic segment and the segments which are in its crown. Furthermore, the resolution to which segments are identifiable places a limit on the identification of homologies. With present imaging technologies for angiography (in particular, for X-ray angiography), a 0.5 mm limit is typical, and potentially sufficient, particularly for the determination of measurements of anatomy/function affecting clinical treatment. As imaging technology improves, this lower limit will potentially be reduced.

For example, in some embodiments, images for use are obtained such that the trunk segment is shown in each 2-D image. Where contrast dye injection is used with imaging, the trunk segment can be identified from information such as the point from which filling begins, from which washout initiates, the point furthest from the dye-filling ends of the contrast-filled region, or another dye-related parameter. Other trunk identification features include the widest terminal point of the tree, the segment indicated by the direction of vascular tapering, and/or a stereotypical position relative to the image frame. Optionally, manual input from an operator is used to select, refine, and/or confirm homology starting points. Optionally, all homology determination is automatic.

From homologous identification of the trunk segment of a vascular tree, homology relationships of other segments in a determined connectivity relationship to that tree are readily identified by their branch order and branch direction. With respect to the methods of FIGS. 17A-17C: in some embodiments, one or more of these methods is applied only to one or more "anchor" segments, with the homology identification of other vessels following from this initial determination. In some embodiments, the whole vascular tree (including the trunk, or including all crown collaterals, for example) is not available in each image. Optionally, identifications of homology are bridged across gaps by using an additional anchor segment.

FFR from 2-D Images, Based on Segment Homologies

Figure 16:
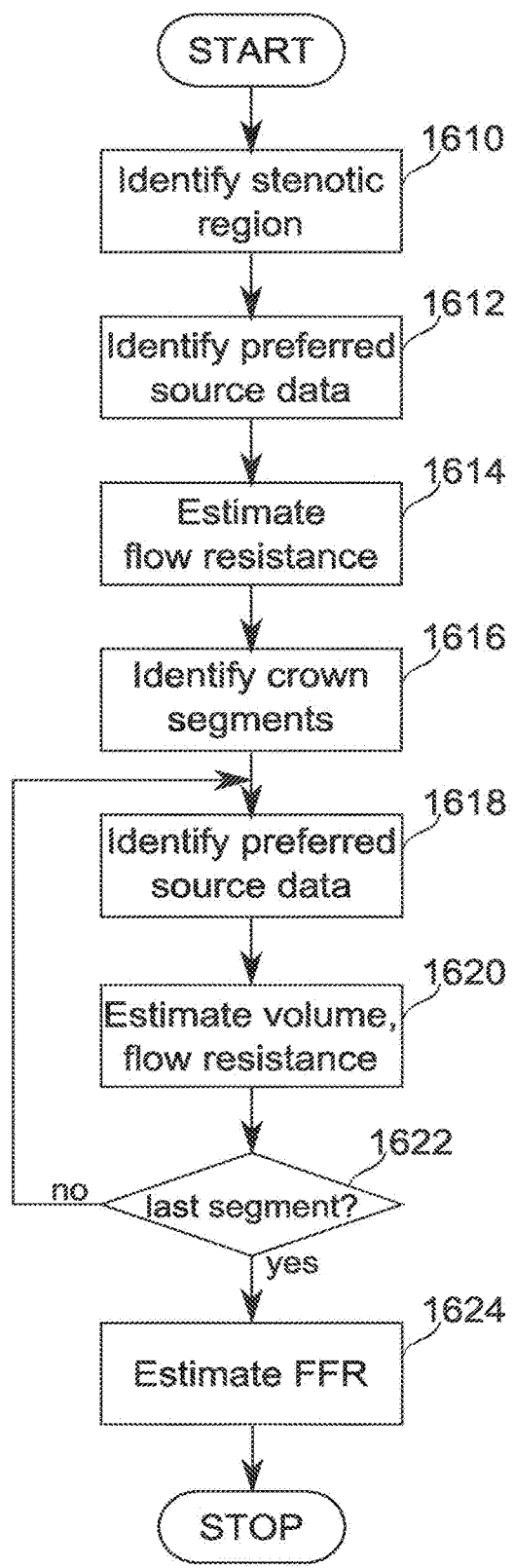
FIG. 16 is a flowchart schematically representing calculation of a fractional flow reserve from 2-D (image) data, according to some exemplary embodiments of the invention.

Reference is now made to FIG. 16, which is a flowchart schematically representing calculation of a fractional flow reserve (FFR) from 2-D (image) data, according to some exemplary embodiments of the invention.

At block 1610, in some embodiments, stenotic regions are identified. Identification of stenotic regions from a 2-D image is described, for example, in relation to FIGS. 6 and 7A-7B.

At block 1612, in some embodiments, preferred starting data for calculation of stenotic vessel metrics is identified. In some embodiments of the invention, identification of the preferred starting comprises identification of homologous representations in the data of the stenotic vascular segment (for example, as described in relation to FIGS. 17A-17C). Selection of the preferred starting data is from among these homologous representations.

In calculating FFR, a relevant metric is the resistance to flow of one or more segments considered. Calculation of the resistance of a segment from an image providing length and radius information is described, for example, in International Patent Application No. IL2014/050043 filed Jan. 15, 2014, by the Applicant, the contents of which are included herein by reference in their entirety. In embodiments where FFR is to be used in planning clinical interventions, the contribution of a stenotic segment to resistance to flow is generally the most sensitive portion of resistance determination compared to the resistance of downstream (crown) vessels.

In general, a projection image of a segment is liable to foreshortening, which potentially affects the value of length used (and/or the radius described as a function of offset along the vascular segment). An aspect of applying Equation I, accordingly, is determination of a value to use as the segment's true length. For a sufficient number of well-chosen imaging planes, the projection in which a vascular segment appears longest is optionally taken as approximating the true length of the vascular segment. Additionally or alternatively, the extent of a segment back-projected into 3-D (for example, the course of the path of closest approach between rays in a brute-force, two-image back-projection such as described in relation to FIG. 17A) provides an estimate of the vascular segment length. Additionally or alternatively, the registration method of FIG. 17B also allows estimation of vascular length from the effects of transformations applied to match segments.

In some embodiments, the image data chosen as the source data are the same as the data used to directly estimate the stenotic segment's actual length. In some embodiments, the source data comprise one or more 2-D image portions to which a suitable length calibration is applied to adjust for the effects of foreshortening. Estimates are optionally performed on a single representative image for each segment/segment condition. Alternatively, estimates are made for two largely orthogonal (but approximately longitudinal) views of the segment, allowing, for example, calculation of a minor and major axis of the segment, and/or averaging of separately estimated values. Additionally or alternatively, estimates of vascular metrics are made using any number of the 2-D images for which a sufficiently extended longitudinal view of the segment of interest is available.

Where a plurality of measurements are available (for example, from a plurality of corresponding 2-D images), the result used in subsequent calculations is optionally a selection from these measurements, or a combination such as an average. Optionally, subsequent calculations are carried out using several of the available measurements separately. This is made feasible by the reduction of the image dataset to a relatively small number of numbers such as, for example, a resistance for each image angle and segment. A potential advantage of using measurements sourced from several different images and/or angles is preserving the ability to build up a probability profile for report metric values which takes into account aspects of measurement error.

Although the blocks of FIG. 16 are described in relation to the calculation of FFR, it should be understood that the considerations relating to selection, calibration, and use of selected sections of 2-D images in the context of determining anatomical and/or functional metrics of a vascular tree apply as well (changed as appropriate) to other metrics. Metrics relevant to vascular function and/or anatomy include, for example: vascular width, tortuosity, flow resistivity, elasticity, auto-regulatory capacity, wall thickness, wall roughness, vascular lumen contrast density (and/or another feature which potentially reveals thrombus), contrast density along the vascular wall (and/or another feature which potentially reveals arterial hardening), and/or other flow characteristics such as possible turbulence patterns.

At block 1614, in some embodiments, flow resistance is estimated.

For example, the following equation describes resistance in branch (where "branch" indexes over vascular segments of interest) as a function of length 1 and radius r:

$$R_{branch} = \frac{8 \times 0.035_{g/cm \cdot s}}{\pi} \sum \frac{dl_i}{r_i^4} \quad \text{Equation 1}$$

This is described also, for example, in International Patent Application No. IL2014/050043. Suitable calibration of length is, for example, as described in relation to block 1612.

At block 1616, in some embodiments, crown segments to the stenotic vessel are identified and selected for further calculations. Crown segments comprise vessel segments downstream of the stenotic vessel segment. Optionally, if there is more than one stenotic vessel segment, each stenotic vessel segment has its own set of crown segments. Determination of crown segments is based, for example, on a model of the vascular tree representing vascular segment connectivity. The vascular tree model is derived, for example, from one or more 2-D images of vascular tree. Optionally, the model is based on a suitable sequence of skeletonization, edge detection, and/or other operations to determine vascular segment centerlines and their connectivity. Optionally, crown segments which identified but below a threshold of diameter which can be accurately determined from available data (for example, due to resolution limitations) are left out of the selection.

Potentially, resistance due to vessels smaller than the crown vessels distinguishable in the acquired images is treated as a lump resistance, or simply disappear into the choice of constants in the final FFR calculation. Compared to the flow effects of a lesioned area, errors in crown vessel estimate potentially only weakly affect the outcome, due, for example, to their already normally low flow resistance values.

Blocks 1618-1622 are performed per identified and selected crown segment.

At block 1618, in some embodiments, preferred source data for calculation of crown segment metrics is identified. For each crown segment to be involved in the FFR calculation, corresponding image data for metric extraction is selected (and optionally combined and/or used for calculations in parallel), for example according to techniques and/or considerations described in relation to block 1612.

At block 1620, in some embodiments, the volumes and flow resistances of the vascular segments of the crown of the stenotic segment are estimated from the 2-D image data (suitably calibrated for foreshortening effects). Volume is calculated, for example as the volume of a summation of cylinders of radius r and calibrated length 1 along the vascular segment image length.

At block 1622, in some embodiments, if there is another crown segment to analyze, flow returns to block 1618. Otherwise, flow continues with block 1624.

At block 1624, in some embodiments, the FFR is estimated. FFR index calculation is described, for example, in International Patent Application No. IL2014/050043 filed Jan. 15, 2014, by the Applicant, the contents of which are included herein by reference in their entirety. For example, the resistances of the stenotic segment and each crown segment are considered in series and/or in parallel (according to their relative locations in the crown) to determine total flow Q5. Optionally an astenotic version of the stenotic segment is determined, for example, according to descriptions of virtual revascularization herein, and the flow QN recalculated. The relative flows then comprise an estimate of FFR:

$$FFR = \frac{Q_S}{Q_N} \qquad \text{Equation 2}$$

Potential advantages of the method of FFR just described are that it allows bypassing some or all of the computationally intensive operations needed to generate a full 3-D tree. Another view of this method is as a demonstration of the separate treatment of the problems of data-region homology, target metric calculation, and global structure. While a full 3-D model (for example, a mesh or stacked-disk model) can potentially be used to address any or all of these problems, there is a potential advantage in treating them in processing as separate aspects. For example, this allows each to be solved by the level of computational effort the problem requires to give satisfactory results-without drawing in extraneous intermediate results. In some embodiments, this separation also allows separation of real-time problems from non-real-time problems, and/or problems requiring precision from problems where the result need only be approximate, suggesting, and/or indicative.

For example, in some embodiments, a detailed (for example, high resolution, mesh, small-cylinder, and/or full skeleton vascular tree) 3-D model is used together with one or more of the above calculations. For example, a 3-D model optionally is generated to present a convenient interface for navigation and/or interaction with a vasculature model. Optionally, the 3-D model is generated in detail before a procedure where real-time responsiveness is required, for example, from already available imaging data. Optionally, the 3-D model used is generated to relatively permissive (low resolution/low accuracy) requirements of an "interaction" model, which shows the vasculature status of the patient as an approximation suitable for manipulation. Optionally, the calculation model is mapped to the 3-D model, for example, on the basis of segment homology, but is itself based on data analyzed separately from the analysis used to create the model.

Stenosis Determination—Vascular Tree- and Graph-Based

Figure 9:
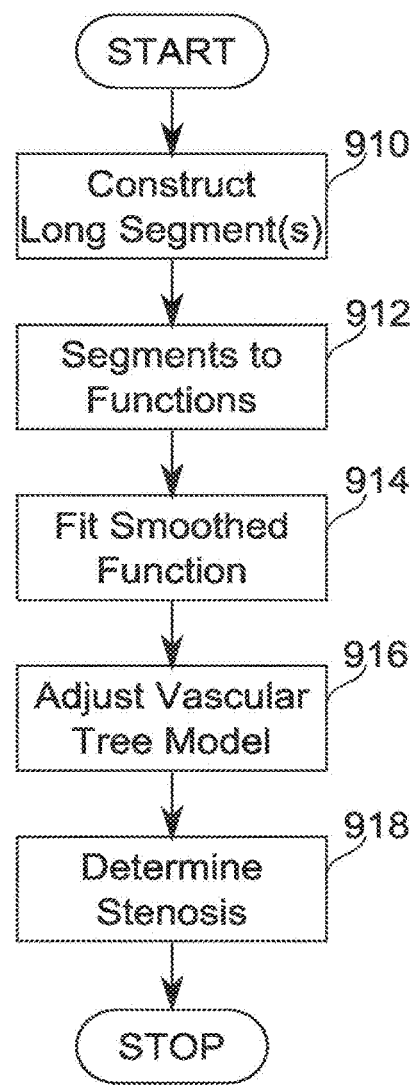
FIG. 9 is a flowchart describing in broad outline a method for refining a revascularized model of a vascular segment using information from neighbor segments, according to some exemplary embodiments of the invention.

Reference is now made to FIG. 9, which is a flowchart describing in broad outline a method for refining a revascularized model of a vascular segment using information from neighbor segments, according to some exemplary embodiments of the invention.

In some embodiments of the invention, a method is provided which takes into account constraints applicable to the morphometric relationships between vascular segments in determining an unstenosed vascular model. Potentially, this allows more accurate determination of an unstenosed vascular model, and/or reduces the occurrence of artifacts which do not reflect reasonable anatomical situations. The method uses information about the branched structure linking vascular segments (for example, a vascular tree graph 240), and information about vascular width (for example, 1-D graphs 230).

The flowchart begins, and at block 910, one or more long segments are constructed by the concatenation of a plurality of interconnected shorter segments into single functions. In some embodiments, the shorter segments are defined by branch points, and the construction of long segments comprises trimming off different branch alternatives for different long segments. In some embodiments, each possible long segment implied by the underlying vessel segment hierarchy is constructed.

At block 912, in some embodiments, long segments are converted to functions, for example, to a one dimensional function of arc-length. In some embodiments of the invention, the function describes radius, diameter, cross-sectional area, and/or another metric related to a degree of stenosis as a function of position along the segment.

At block 914, in some embodiments, a smoothed function $\check{f}(s)$ is fitted to the data of $f(s)$. The fitting, in some embodiments, is subject to a similarity criterion, for example, minimization of $|f(s)-\check{f}(s)|$. Ask The fitting, in some embodiments, is subject to a smoothness criterion, for example, minimization of $|\check{f}''(s)|$.

In some embodiments, the fitting further comprises the criterion of minimizing $\check{f}'(s)$, for example, such that this value is everywhere non-positive. A potential advantage of this criterion is that it takes advantage of an observed property of healthy vascular trees, which are seen to narrow monotonically when moving from trunk to branch. Thus, for example, a case may arise in which an entire segment is narrowed, thus providing no healthy region as an internal reference. In such a case, a single undiseased downstream segment nevertheless potentially signals that the unstenosed diameter of the highly diseased upstream segment should be larger than the observed vessel diameter.

At block 916, in some embodiments, an adjusted unstenosed model of a vascular segment is referred back to the original vascular tree model.

At block 918, in some embodiments, a degree of stenosis is calculated from the adjusted unstenosed vascular segments, for example as described herein above with reference to FIG. 6 and/or FIGS. 7A-7B. The flowchart ends.

Model Updating

Model Updating for Vascular Assessment

Figure 10:
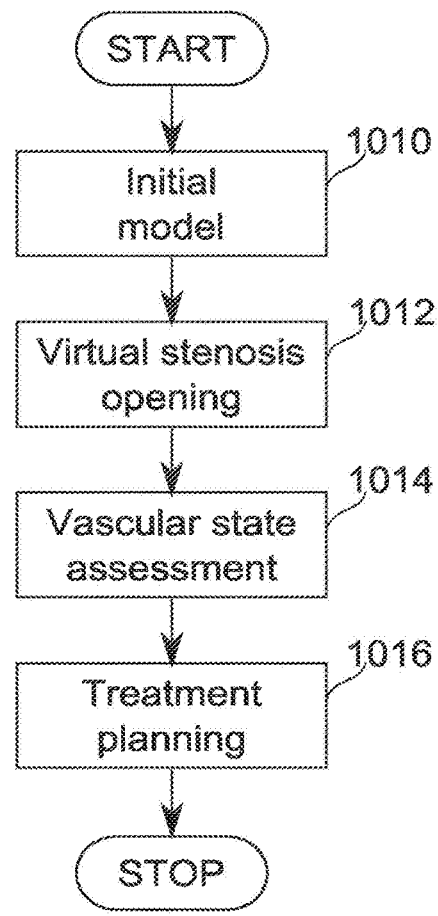
FIG. 10 is a flowchart illustrating in broad outline the use of virtual stenosis opening in the context of clinical diagnosis and treatment planning, according to some exemplary embodiments of the invention.

Reference is now made to FIG. 10, which is a flowchart illustrating in broad outline the use of virtual stenosis opening in the context of clinical diagnosis and treatment planning, according to some exemplary embodiments of the invention.

In some embodiments of the invention, virtual stenosis opening and/or other computational ("virtual") vascular tree model modifications are used as part of the assessment of a clinical situation. In some embodiments, the assessment occurs in real time, for example, during a catheterization procedure during which imaging occurs. Potentially, real-time clinical assessment based on a vascular tree model which is rapidly generated and/or updated provides feedback which is useful in immediate treatment planning.

At block 1010, m some embodiments, an initial model of the coronary vasculature is created, for example using source images from X-ray angiography reconstructed into a vascular tree model as described hereinabove.

At block 1012, in some embodiments, virtual stenosis opening occurs based on the reconstructed vascular tree, for example as described with respect to FIGS. 6-9 hereinabove. It should be understood one or more additional or alternative model-based virtual updates to the vascular tree are also possible at this stage. For example, in some embodiments, model adjustment optionally comprises computation of the effects of a shunt around a lesion, similar in the effect achieved by a coronary bypass. The shunt is optionally modeled as an actual shunt (vessel arranged in parallel with the native circulation), or more abstractly as a bypass-equivalent opening of a stenosed area.

It is a potential benefit to be able to rapidly perform both "virtual PCI" and "virtual CABG" operations in real time, for example to establish more clearly the relative complexity and potential benefits of alternative procedures. This benefit is potentially realized even though CABG is generally postponed to a later-scheduled procedure, for example, insofar as it assists in the rapid evaluation of borderline cases where the decision to proceed with PCI or CABG is initially uncertain.

More generally, the scope of block 1012 embodiments encompasses model adjustments which reflect any modification to the vasculature which can be achieved by a treatment intervention, by means including direct functional parameter adjustment (for example, increasing flow to 50% higher by "computational fiat"), the introduction of simulated data (for example, image data, either automatically or manually generated, comprising a new vessel "sketched in", or a stenotic lesion "rubbed out"), and/or computationally performed model adjustments such as are described hereinabove for determining a level of vascular stenosis automatically.

At block 1014, in some embodiments, a vascular state assessment is performed. In some embodiments, the state assessment comprises use of one or more model states (for example, the current state and a virtually astenotic state) to determine an index or functional parameter which bears on the clinical situation, for example a vascular state score such as Syntax Score, or an index such as the flow fractional reserve.

At block 1016, in some embodiments, treatment planning occurs. In some embodiments, planning is assisted by the assessment results of block 1014. Treatment planning which is assisted comprises, for example, a decision to go forward with percutaneous coronary intervention (PCI), or to instead make another recommendation, such as scheduling coronary artery bypass surgery (CABG). Assistance, in some exemplary embodiments, takes the form of supplying a coronary vasculature state index, such as the Syntax Score index. An aspect of generating a Syntax Score assessment is the evaluation of stenotic lesion severity. Other parameters relevant to a vascular state score vascular state score include the presence of thrombosis, vascular tortuosity, and/or relative vascular branch diameters. Each of these is potentially represented within the vascular tree model, for example within one or more of the representational modes detailed hereinabove. Additionally or alternatively, they are generated as intermediates used only within a vascular scoring output module. In some embodiments of the invention, FFR calculation is performed within one or more segments of the imaged vasculature, to determine if there is a likely clinical value to intervention in the form of increased flow after treatment.

Additionally or alternatively, one or more "virtual stents" can be applied to the vascular tree model, adding interactivity to the information on vascular status supplied by a FFR and vascular state scoring. In simple embodiments, a virtual stent is implemented, for example, as a notch constraint to a 1-D graph of vascular segment width, wherein the vessel width is set to be no narrower than some minimum width over some length representing the extent and diameter of a vascular stent. Other embodiments of virtual stent modeling are described in relation to FIG. 11, hereinbelow.

Figure 11:
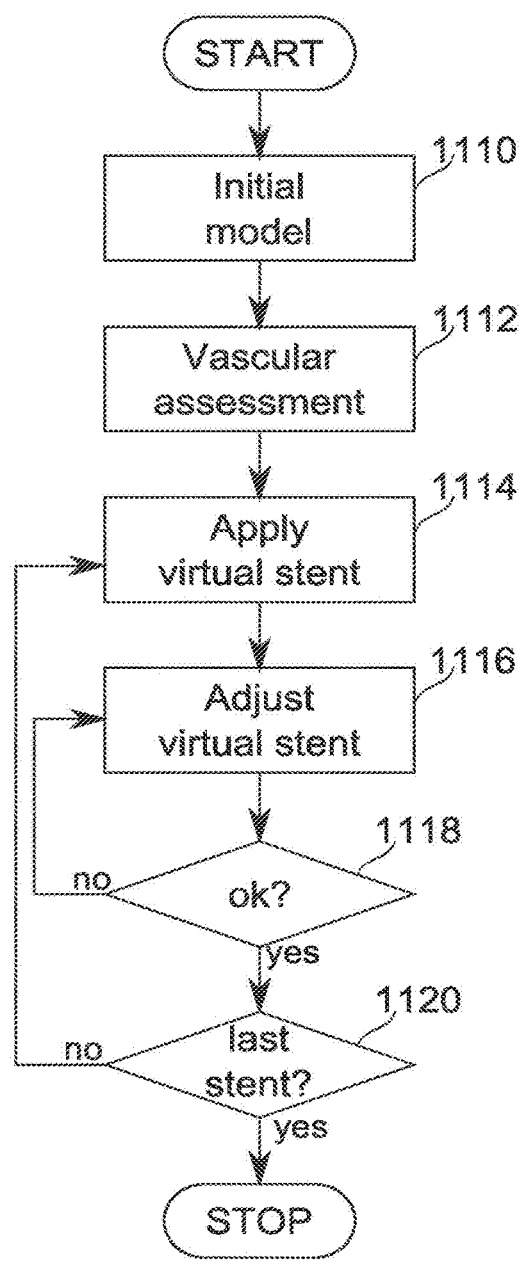
FIG. 11 is a flowchart illustrating m broad outline the use of virtual stent modeling in the context of clinical treatment planning, according to some exemplary embodiments of the invention.
Figure 12:
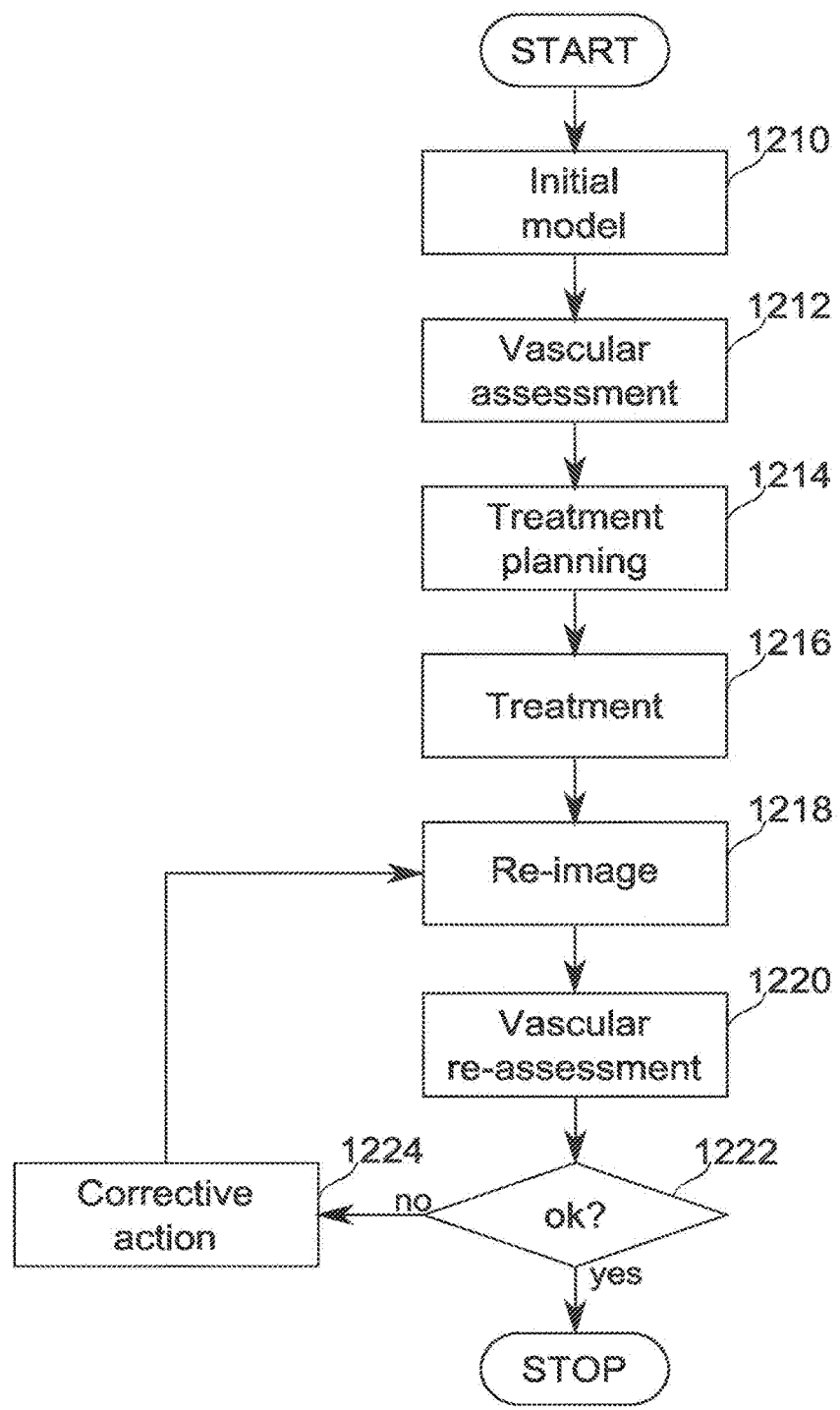
FIG. 12 is a flowchart illustrating in broad outline the use of a real-time updatable vascular tree model in verifying treatment outcome, according to some exemplary embodiments of the invention.
Figure 13:
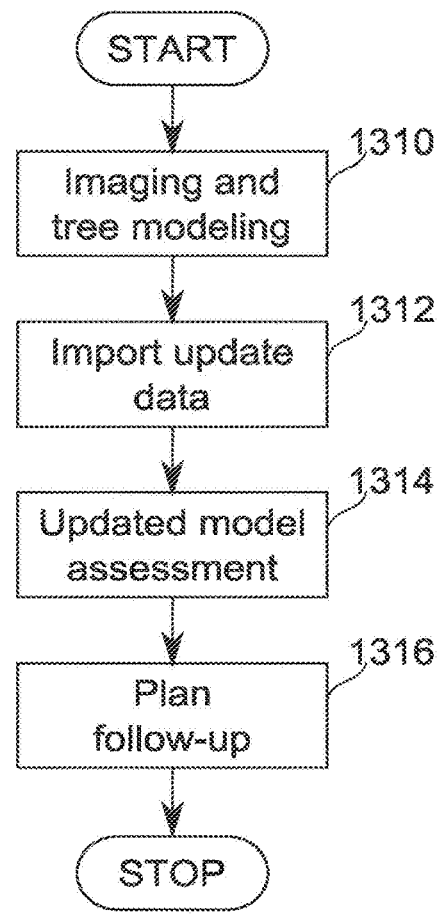
FIG. 13 is a flowchart illustrating m broad outline the use of an updatable vascular tree model in making disease progression and or comparative state vascular assessments, according to some exemplary embodiments of the invention.
Figure 14:
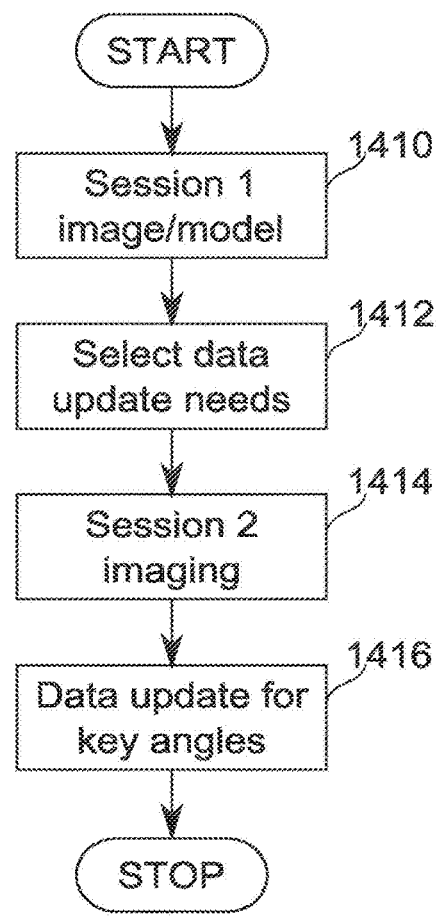
FIG. 14 is a flowchart illustrating in broad outline incrementally updating of a vascular tree model, according to some exemplary embodiments of the invention.

It is to be understood that the broad outlines of the method of FIG. 10 are applicable to be filled out in alternative embodiments based on any of the systems and methods described herein (for example, the treatment planning of FIG. 11)—or to fit within or alongside the context of other methods, including those of FIGS. 12-14.

Model Updating for Procedure Planning

Reference is now made to FIG. 11, which is a flowchart illustrating in broad outline the use of virtual stent modeling in the context of clinical treatment planning, according to some exemplary embodiments of the invention.

In some embodiments of the invention, treatment planning comprises making decisions about how and where to intervene, as well as understanding the relative risks of success or failure. These are described with respect to FIG. 11 in most detail in terms of the implantation of a "virtual stent" (to mimic the planned implantation of a real vascular stent), but it is to be understood that alternative PCI treatments such as angioplasty are additionally or alternatively simulated, in some embodiments. For example, angioplasty effects are optionally simulated as full or partial removal of an occlusion, according to the expected results of the intervention. In some embodiments of the invention, CABG intervention, or another non-PCI intervention is simulated. Even when there is no expectation to actually proceed to CABG, providing this capability during a PCI planning stage provides potential benefit by allowing, for example, a worst-case what-if scenario to be partially rehearsed in advance. Additionally or alternatively, it is a potential benefit for skill and judgment development to be able to review alternative scenarios within a common framework.

At block 1110, in some embodiments, the initial vascular tree model is generated, for example according to one or more of the methods described hereinabove.

At block 1112, in some embodiments, vascular assessment is performed, for example, as described in relation to FIG. 10, hereinabove.

At block 1114, in some embodiments, a virtual stent is applied to the vascular tree model. A notch-like 1-D simulated stent is described in relation to block 1016 of FIG. 10. Optionally, the simulation comprises modifications of vascular width beyond the length of the stent, reflecting, for example, the elasticity of the vascular wall. In some embodiments, the stent is simulated in 2-D. It is implemented, for example, by forming a stent-shaped deformation in a vascular wall's 2-D image, then re-importing the modified image into the model. Potentially, this provides an advantage by preserving information about the implantation site's curvature and surrounding environment, which potentially affects the parameters of stent implantation. Updating of 2-D images taken from more than one angle is optionally performed, for a more complete assessment of the implant environment. In another exemplary implementation, stent implantation is simulated in 3-D, either within the vascular tree model itself, as part of a viewable output module, or both.

At block 1116, in some embodiments, the position and/or dimensions of the virtual stent are adjusted. In one exemplary scenario, an initially selected stent is too short relative to a lesion, such that occlusion potentially remains after the stent is deployed. A longer stent is selected. In another exemplary scenario, the stent selected does not fit in the required space, for example due to constraints of curvature and/or vascular branching, and must be shortened or narrowed. In yet another exemplary scenario, it is unclear which of two alternatives is preferable until each has been virtually implanted. In a further scenario, trials are made with a stent which is deployable to an adjustable diameter, to find a preferred balance between degree of occlusion opening and risk of injury by over-expansion. At this block also, another PCI or non-PCI treatment is optionally simulated, for example balloon angioplasty.

Optionally, other aspects of the planned treatment are evaluated at this stage. For example, the effects of misplacement from a precise target position are simulated, as part of evaluating whether or not the expected positional tolerances are appropriate to all eventual situations.

At block 1118, in some embodiments, a determination is made as to whether or not the virtual stent or other planned treatment is acceptable as planned. Planned placement is validated by viewing of a model view, and/or by automatic assessment to verify that the planned stent does not fall outside of recommended parameters for its projected location. In some embodiments, a vascular state index, FFR, or other assessment tool is used to determine that the functional effects of the stent are likely to be adequate to the requirements. If the stent plan is validated, the method continues at block 1120. Otherwise, planning returns to block 1116 for further adjustments.

At block 1120, in some embodiments, a determination is made as to whether or not another stent implantation (or other intervention) should be performed. The FFR and vascular state indexes optionally calculated during validation of the previous planned interventions potentially also serve to indicate whether additional interventions are called for. If another stent or other intervention is indicated, the method returns to block 1114. Otherwise, the flowchart ends.

Model Updating for Procedure Verification

Reference is now made to FIG. 12, which is a flowchart illustrating in broad outline the use of a real-time updatable vascular tree model in verifying treatment outcome, according to some exemplary embodiments of the invention.

In some embodiments of the invention, the real-time updatability of the vascular tree model with new data allows verification of the functional effects of treatment to be performed within the time-frame of the procedure, based on images acquired during and/or after the treatment phase of the procedure. Such images are typically acquired in any case for the sake, for example, of verification of placement and avoidance of injury.

Initial generation of the model potentially requires a few minutes, for example, 2-5 minutes, 4-10 minutes, 8-15 minutes, or another range of times having the same, intermediate, larger or smaller bounds. However, once established, the integration of new images is potentially even more rapid, on the order of a few seconds or less. This is because the calculations devoted to finding homologies among images need not be repeated in full-homology between any single new image and any other image already mapped to the model, for example, is potentially sufficient to determine the positions of vascular segments the new image contains.

At block 1210, in some embodiments, the initial model is created. At block 1212, in some embodiments, vascular assessment is performed, and at block 1214, in some embodiments, treatment planning is performed. Each of these blocks is described, for example, in relation to one or more of the figures presented hereinabove.

At block 1216, in some embodiments, treatment is performed. This comprises, for example, PCI treatments such as stent implantation and/or balloon angioplasty.

At block 1218, in some embodiments, verification imaging is performed (re-imaging). The imaging is optionally according to the same protocol that was used to acquire the original model images. However, it is a potential advantage to re-acquire a more limited set of images, according to the needs of verification. The ability of the vascular tree model to absorb arbitrary vascular imaging data on broadly equal terms with the data originally used in its generation potentially allows less image data to be acquired, without significantly degrading the quality of assessments that can be performed. This is described also, for example, in relation to FIG. 14, hereinbelow.

At block 1220, in some embodiments, vascular re-assessment is performed, according to the requirements of the procedure. In addition to the assessment options available before intervention, at least two additional types of assessment option are available post-intervention: assessment relative to the original vasculature, and assessment relative to one or more planned vascular states.

Assessment relative to original vasculature allows direct before-and-after comparisons, which potentially identify unexpected changes (for example, due to injury), or simply a direct verification that the location of a previously noted stenotic lesion is now clear and/or occupied by a stent implant.

Assessment relative to the planned state of the vasculature (which comprises, for example, the original vasculature, as modified by virtual stents, virtual angioplasty, or another procedure) potentially identifies some of the same information. Additionally or alternatively, it can also serve to validate the projected effects of the virtual procedures. Where actual results differ from those projected, it is possible, in some embodiments, to use this difference to update the parameters of the virtual stent module, for example to modify the risk of mis-positioning, the expected elasticity of the vascular wall, or another parameter of the model or module.

At block 1222, in some embodiments, a determination is made as to whether or not the effects of the treatment in block 1216 are acceptable. If not, corrective action is taken at block 1224, and, optionally, re-imaging takes place at block 1218 followed by another re-assessment. If treatment results are acceptable, the flowchart ends.

Model Updating for Progression, Comparative State, and/or Comparative Modality Analysis Reference is now made to FIG. 13, which is a flowchart illustrating in broad outline the use of an updatable vascular tree model in making disease progression, comparative state, and/or comparative modality vascular assessments, according to some exemplary embodiments of the invention.

At block 1310, in some embodiments, imaging and vascular tree reconstruction is performed, for example as described hereinabove.

At block 1312, in some embodiments, update data is imported from an imaging and/or DAQ procedure. In some embodiments, the update data is from a separate imaging and/or DAQ procedure, occurring at any time before, during, or after the acquisition of images from which the vascular tree was reconstructed in block 1310.

In some embodiments of the invention, the updating data comprises data taken using one or more imaging or other DAQ modalities, before, during, and/or after the data used in the original vascular tree construction. Imaging and DAQ modalities comprise any of the imaging/DAQ methods mentioned hereinabove, for example, X-ray angiography CT, MRI, PET, OCT, and/or IVUS. Optionally, modality by which the data is obtained is not the same as the modality by which the data comprising the original vascular tree reconstruction. Optionally, the coverage of the imported data of the reconstructed vascular tree is incomplete, comprising only, for example:
- a portion of the reconstructed vascular segments, \
- one image plane,
- a set of images which does not provide 3-D information, and/or
- a set of images which provides incomplete 3-D information.

Insofar as the newly imported data is imported by a data updater 104 and related to one or more of the mappings/taggings of the vascular tree reconstruction 102 (for example, one of the 1-D, 2-D, or 3-D mappings described hereinabove), it is potentially usable in conjunction with a virtual updater 101, and/or output module 130 which is configured to receive data having such a mapping. Imported data is potentially relevant to assessing changes in diagnostic state, prognosis for future change, for treatment planning, or for other reference.

At block 1314, in some embodiments, an assessment based on the updated model (and/or plurality of models) is performed. There are different uses to which embodiments of a data-updated model are applicable.

In some embodiments of the invention, a vascular tree model (and/or a plurality of homologous vascular tree models) comprises data taken at different times—the difference in time ranging from milliseconds to years or any period in between—where the difference in time comprises a diagnostically significant difference in vascular state. Such a state difference comprises, for example, one or more of the following:
- progression of disease state (over periods of weeks, months or years), for example: changes to and/or development of vascular lesions such as stenosis, changes to vascular tortuosity, or other developments in chronic vascular disease state;
- vasculature motion due to physiological function (over periods of several milliseconds to seconds), potentially including, for example: bulk vascular motion from heartbeat and/or respiration, and/or phasic expansions/contractions of vascular diameter due to changes in blood pressure and/or autoregulation; and/or
- changes in vascular condition due to differences in a manipulated state (over periods of seconds, minutes, hours, or another suitable period), the manipulated state being, for example: performance of a treatment procedure (such as angioplasty, stent implantation, or surgery; an exemplary description is provided in relation to block 1220 hereinabove), differences in exertion and/or administration of drugs (such as drugs comprising vasodilation and/or vasoconstriction activity).

Relating the data of multiple imaging/DAQ sessions and/or modalities through the vascular tree model potentially derives one or more of the following exemplary advantages:
- New data is rapidly integrated into a 3-D and/or otherwise inter-related data structure, where it can be quickly searched for and/or reviewed without incurring the delays of a new vascular tree reconstruction phase. The method described in relation to FIG. 12, exemplifies real-time verification of an implantation procedure.
- Data acquisition (for new data) can be concentrated on vascular regions where differences are of greatest concern, while still relating the region of interest to the vasculature overall. The method described in relation to FIG. 14, for example, relates also to this advantage.
- Substantially contemporaneous data, even of multiple modalities, can be related to provide a multi-parameter view of a given region of the vascular tree. For example, the detailed structural information provided by IVUS imaging is given context, in some embodiments, by its relationship to the plane of view of an X-ray angiogram image.
- Old data, even when taken using a different imaging/DAQ modality, can be related to new data; for example, by means of a view module 135 which registers data views according to their tagged/mapped locations, and presents them to allow direct comparison (by homologous marks, side-by-side presentation, alternating overlapped presentation, or another display means). Potentially, this allows progression of disease to be inferred using historical data as a baseline, even if the older data is "stereoscopically incomplete".

At block 1316, in some embodiments, results of the assessment are integrated into a plan of action. Use in verification is described, for example, in relation to FIG. 12. Use in planning of imaging is described, for example, in relation to FIG. 14. In an exemplary scenario-based on the observed rate of progression of a state of vascular occlusion-a schedule for follow-up visits is determined, and/or a patient is advised about possible effects of their recent lifestyle on halting or advancing their disease.

Need-Basis Image Data Updating

Reference is now made to FIG. 14, which is a flowchart illustrating in broad outline incremental updating of a vascular tree model, according to some exemplary embodiments of the invention.

At block 1410, in some embodiments, a first imaging/DAQ session occurs, and the resulting data is used to produce a vascular tree reconstruction, for example as described hereinabove.

At block 1412, m some embodiments, data update needs are selected. For example, after an implantation procedure in a particular vascular branch, verification imaging can be concentrated on views showing that branch most clearly. A potential advantage of such concentration is to reduce overall radiation dosage to a patient, and/or to allow increased radiation exposure for the image(s) most relevant to the verification. The option for such selectivity also pertains to long-term follow-up visits, where a particular vascular region has been previously identified as needing monitoring.

At block 1414, in some embodiments, the images are obtained in a second session. It is to be understood that the distinction among "sessions" can comprise different visits or catheterization procedures, but can also comprise different phases of a single procedure, separated by the availability of a vascular tree reconstruction and the decision to guide additional imaging based on its availability.

In some embodiments of the invention, the second session comprises switching the imaging modality from the modality used for initial vascular tree reconstruction. Potentially, this removes or reduces a requirement for dangerous irradiation. For example, a vascular model established using X-ray angiography images is updatable, in some embodiments, using IVUS in a vessel of particular interest.

At block 1416, in some embodiments, the update occurs, for example, by providing an appropriately configured data updater 104 with the newly acquired images or other acquired data.

Exemplary Systems
Exemplary System for Vascular State Scoring

Figure 15:
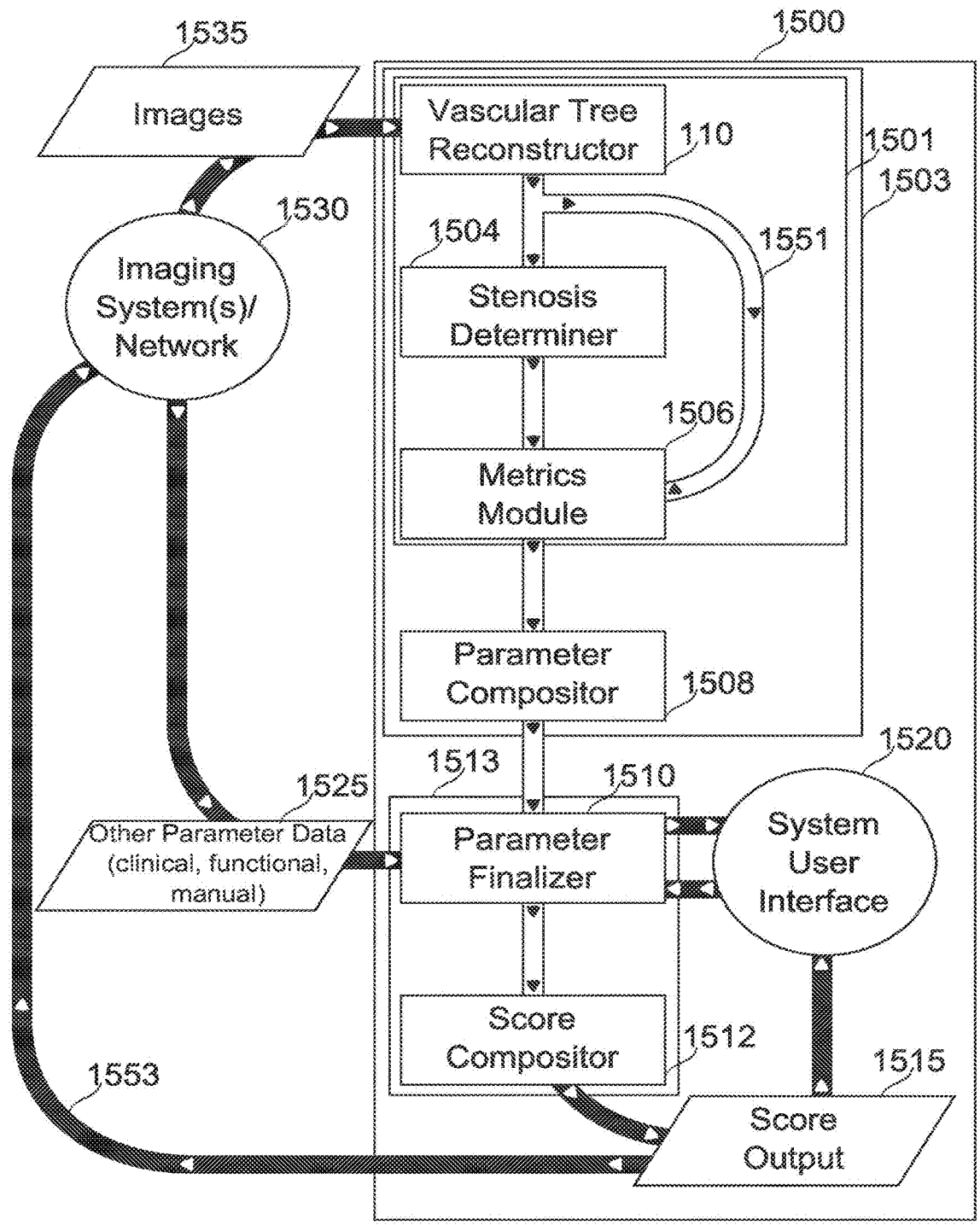
FIG. 15 is a simplified schematic of an automatic vascular state scoring system, according to some exemplary embodiments of the invention.

Reference is now made to FIG. 15, which is a simplified schematic of an automatic vascular state scoring system 1500, according to some exemplary embodiments of the invention.

Vascular state scoring system 1500 provides an exemplary implementation of a system which comprises a vascular tree reconstructor 110, having a stenosis determiner 1504 and/or a metrics module 1506 which act as examples of virtual updaters 101. Parameter compositor 1508, parameter finalizer 1510, and/or score compositor 1512 represent exemplary output modules 130, 140 and/or components of one or more exemplary output modules. Score output 1515 represents a component of an exemplary view-style output module 135.

It is to be understood that such a system is optionally provided with additional instances of virtual updaters 101, and/or output modules 130; and/or provided with one or more data updaters 104. For example, an output module 140 (not shown), in some embodiments of the invention, calculates a fractional flow reserve (FFR). FFR is calculated, for example, based on the calculated ratio of flow rate in the originally derived vascular tree reconstruction, and a virtually astenotic reconstruction produced by stenosis determiner 1504. Optionally, a view modules 135 is provided to present the calculated results of the PPR-calculating module.

In FIG. 15, broad white pathways (for example, pathway 1551) denote simplified paths of data processing through the system Broad black pathways (for example, pathway 1553) denote external data connections or connections to the system user interface 1520. Black pathway data content is labeled by overlying trapezoidal blocks.

The vascular tree reconstructor 110, in some embodiments of the invention, receives image data 1535 from one or more imaging systems or a system-connected network 1530. Stenosis determiner 1504, in some embodiments, determines the presence of stenotic vascular lesions based on the reconstructed vascular tree. In some embodiments, metrics module 1506 determines additional metrics related to the disease state of the vascular tree, based on the reconstructed vascular tree and/or determined stenosis locations and other measurements.

In some embodiments, metrics extractor 1501 comprises functions of vascular tree reconstructor 110, stenosis determiner 1504, and/or metrics module 1506. In some embodiments, metrics extractor 1501 is operable to receive image data 1535, and extract from it a plurality of vascular state metrics, suitable, for example, as input to parameter compositor 1508.

In some embodiments, parameter compositor 1508 converts determined metrics into subscore values (for example true/false values) which comprise parameters that "answer" vascular state scoring questions, and/or are otherwise are mapped to particular operations of a vascular state scoring procedure.

In some embodiments, subscore extractor 1503 comprises functions of vascular tree reconstructor 110, stenosis determiner 1504, metrics module 1506, and/or parameter compositor 1508. In some embodiments, subscore extractor 1503 comprises functions of metrics extractor 1501. In some embodiments, subscore extractor 1503 is operable to receive image data 1535, and extract from it one or more vascular state subscores, suitable as input for score calculator 1513.

Parameter finalizer 1510, in some embodiments, ensures that parameter data provided is sufficiently complete and correct to proceed to final scoring. In some embodiments, corrections to automatically determined parameters are determined at finalizer 1510, optionally under operator supervision through system user interface 1520. In some embodiments, lacunae in automatically provided parameter data are filled: for example, by user input from system user interface 1520; or by other parameter data 1525 provided, for example, from another diagnostic system or a network providing access to clinical data.

Score compositor 1512, in some embodiments, composes the finalized outputs into a weighted score output 1515 based on the determined parameters for the score. The score is made available, for example, over the system user interface or to networked resources 1530.

In some embodiments of the invention, score calculator 1513 comprises functions of the parameter finalizer 1510 and/or score compositor 1512. In some embodiments, score calculator 1513 is operable to receive composited parameters and/or subscores (for example from parameter compositor 1508 and/or subscore extractor 1503), and convert them to a vascular state score output 1515.

In some embodiments of the invention, intermediate results of processing (for example, the reconstructed vascular tree, various metrics determined from it, and or parameter determinations) are stored in permanent or temporary storage on storage devices (not show) of the system 1500, and/or on a network 1530.

The scoring system 1500 has been described in the context of modules which, in some embodiments of the invention, are implemented as programmed capabilities of a digital computer. It should be understood that the underlying system architecture may be implemented in various ways comprising embodiments of the invention; for example, as a single or multiple-process application and/or as client-server processes running on the same or on different computer hardware systems. In some embodiments of the invention, the system is implemented in code for execution by a general purpose processor. In some embodiments, part or all of the functionality of one or more modules is provided by an FPGA or another dedicated hardware component such as an ASIC.

As an example of a client-server configuration, a subscore extractor 1503 is implemented as a server process (or group of server-implemented processes) on one or more machines remote to a client computer which implements modules such as the score calculator 1513 and user interface 1520. It should be understood that other divisions of modules described herein (or even divisions within modules) are encompassed by some embodiments of the invention. A potential advantage of such a division is, for example, to allow high-speed dedicated hardware to perform computationally intensive portions of the scoring, while providing an economy of scale by allowing the hardware to be shared by multiple end-users. Such a distributed architecture potentially also provides advantages for maintenance and/or distribution of new software versions.

System Configuration for Addressing Medical Questions and Answers

Reference is now made to FIGS. 1B-1G, which are block diagrams of portions of the system 100 of FIG. 1A adapted for answering various forms of question related to medical situations, according to some exemplary embodiments of the invention.

In some embodiments of the invention, modules 101, 104, 130 are provided which are adapted to work together with a vascular tree model 102 to assist a clinician in asking particular medical questions efficiently and providing timely answers. It is a potential advantage for modules and/or module groups to be structured to address medical questions posed at a high level of abstraction, and to return answers arrived at substantially automatically. The capability to update a vascular tree model partially, and/or in a selected number of representational modalities, potentially allows rapid, dynamically determined vascular tree models to be produced and/or queried for properties which relate, actually or prospectively, to the past, present, and/or future clinical state of a patient's vasculature. Not only can an initial model be produced quickly, in some embodiments of the invention, but the model can also be updated (potentially even more quickly) to produce a result usable within one or more real-time clinical constraints. A wide range of clinical data types (types comprising images and other acquired or manually entered real-world data, for example, but also simulated data) is usable with the vascular tree model, in part due to the availability of several suitable levels of abstraction to which data can be mapped. A multiplicity of what-if scenarios can be rapidly generated using modest computational resources, allowing optimization according to a scheme of weighted metrics assessing scenario outcomes.

FIGS. 1B-1G present exemplary embodiments of module arrangements, and of corresponding exemplary forms of question which each arrangement is suited to formulate and answer. It is to be understood that each figure embodiment relates to a general form of question related to a medical situation, and is not limited to the specific module combinations illustrated along with each of the more general questions.

In some embodiments (FIG. 1B), there exists a question regarding choice of treatment; for example, as to whether which of a group of available treatments (for example chosen from among PCI or CABG interventions) is preferable to improve the clinical situation of a patient. More particularly, in some embodiments, a vascular state index (such as a Syntax Score index) is provided as a proxy for the clinical situation of the patient, which renders the question into a form amenable to calculation by some embodiments of the invention.

The answer is optionally evaluated automatically by an appropriately configured, computerized system Optionally, it is evaluated in real-time, for example, while a patient remains catheterized after an imaging procedure. In some embodiments, an astenotic version of the vasculature (an "astenotic baseline") is generated by a virtual updater module 101B, and the results used by an output module 130B, together with the originally generated vascular tree model, to calculate a vascular state index. In some embodiments, the vascular state index (for example a Syntax Score index), comprises an index which is expected to be correlated with a relatively improved prognosis for one or more of the available intervention, as determined, for example, through clinical studies in the field.

In some embodiments (FIG. 1C), there exists a question regarding the likely effect of a treatment under consideration; for example, as to the likely benefit for a patient's clinical situation upon performing a particular treatment. In some embodiments, the degree of flow restoration expected to one or more parts of the heart, or another parameter based on flow, serves as a proxy for the patient's clinical situation. A treatment considered, in some embodiments, is any intervention (for example, PCI, CABG, and/or drug treatment) which serves to re-open a region of stenotic vasculature.

Figure 1B:
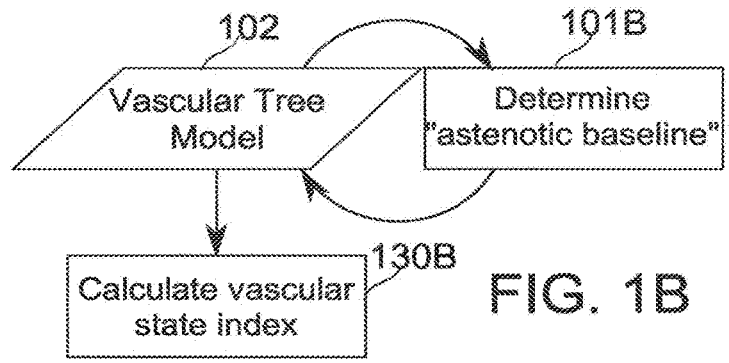
FIGS. 1B-1G are block diagrams of portions of the system of FIG. 1A adapted for answering various forms of question related to medical situations, according to some exemplary embodiments of the invention.
Figure 1C:
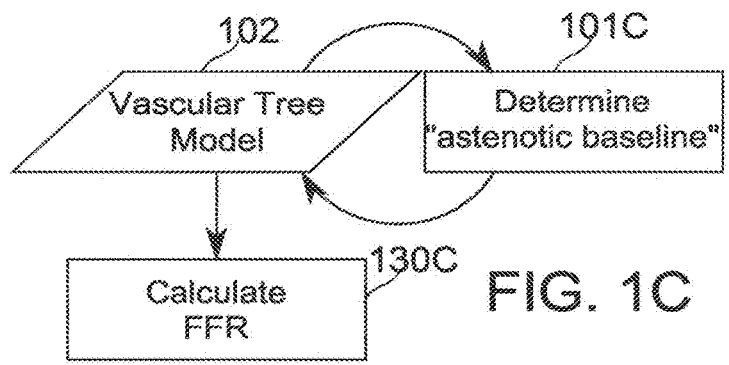
Figure 1D:
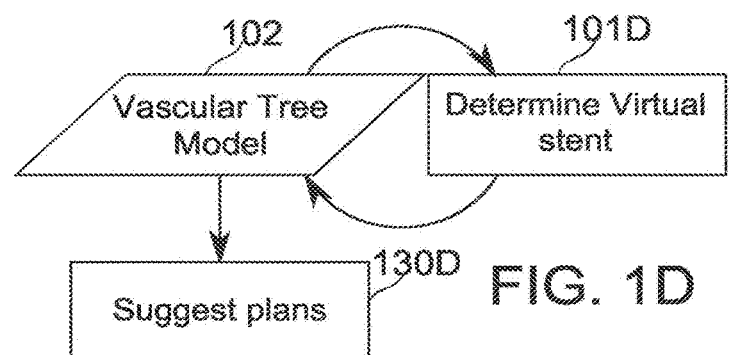
Figure 1E:
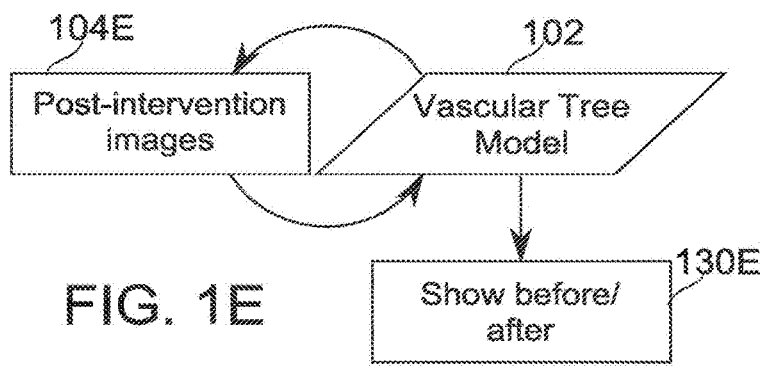
Figure 1F:
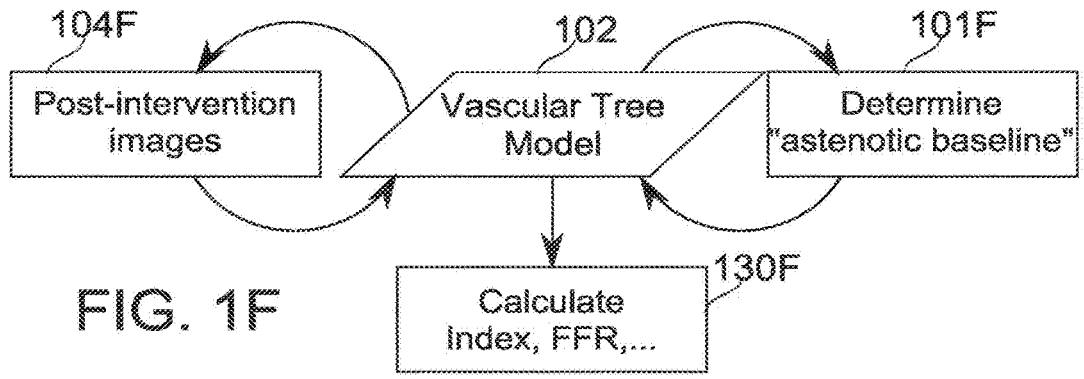
Figure 1G:
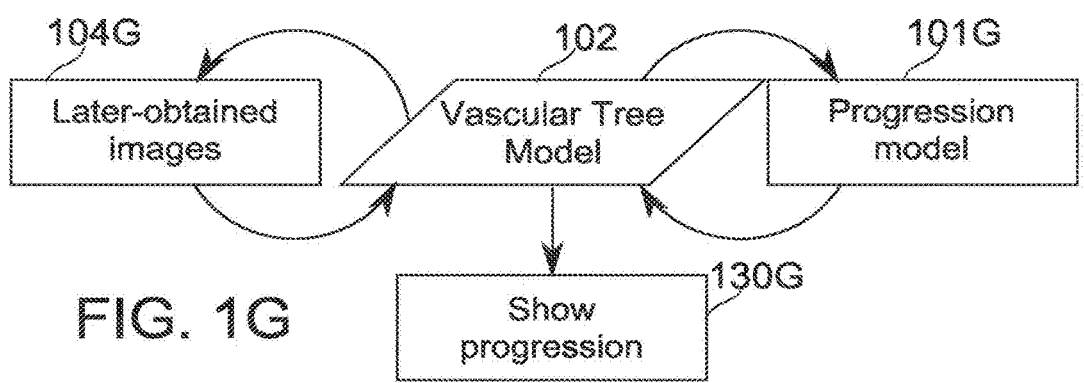

The answer is optionally evaluated under one or more real-time constraints, for example, as described in relation to FIG. 1B. In some embodiments, an astenotic version of the vasculature (an "astenotic baseline") is generated by a virtual updater module 101C, and the results used by an output module 130C, together with the originally generated vascular tree model, to calculate a fractional flow reserve (FFR) index. An FFR index provides an indication of the degree to which a specific blockage is a source of resistance to flow in the overall vascular tree.

In some embodiments of the invention, improvement to flow is indexed to perfusion requirements. For example, a clinician can add to the vascular model (for example using a data updater module 104 adapted to this purpose) estimated or measured information about relative tissue volumes in different heart regions requiring perfusion (fraction of viable tissue perfused, for example). Optionally, the information is combined with flow information and/or FFR calculation in order to determine a course of treatment most likely to relieve anoxia in viable tissue, and/or the effects thereof.

In some embodiments (FIG. 1D), there exists a question regarding planning of how a treatment option is to be carried out to improve a patient's clinical situation. In some embodiments, the question relates, for example, to where and with what specific implant or technique to perform a vascular opening procedure. In some embodiments, the opening procedure comprises placement of a stent, balloon angioplasty, or another vascular opening treatment. In some embodiments, an increase in blood flow volume, or another parameter based on blood flow and/or perfusion efficacy, serves as a proxy for the patient's clinical situation. In some embodiments, choice of one or more quantifiable target conditions for the procedure and/or its modeled results is used in guiding a computerized embodiment of the system to determine (using a virtual stent modeling module 101D) one or more suggested treatment plans, for example, by optimization of a weighted function comprising one or more of the following:

targets for vascular segment blood flow and/or tissue perfusion;

number of sub-procedures (such as balloon inflations) and/or implants required; projected overall procedure time;

characteristics of available devices for implanting, for example, self- or actively-expanding, size, and/or shape;

suitability of stenotic region for safe/stable intervention, for example according to tortuosity, nearness to branches, and/or vascular size; and/or another parameter related to the safety, stability, prognosis, and/or effectiveness of a medical procedure.

The answer presented by output module 130D, in some embodiments, comprises a plan for a treatment procedure, including, for example, selection and placement of one or more stents, placement of a catheter, locations targeted for balloon angioplasty, and/or another plan aspect which serves to guide the performance of the treatment procedure.

In some embodiments (FIGS. 1E-1F), there exists a question regarding verification that a treatment has been performed to achieve the results specified. In some embodiments, the question relates to, for example, whether vascular widening is sufficient in treated regions to restore the level of vascular function targeted. In some embodiments, results are specified, for example, in terms of a vascular width, a modeled blood flow rate, a modeled perfusion efficacy achieved, or another parameter related to the health and or function of the heart.

In some embodiments of the invention, post-procedure images are acquired, and provided to the vascular tree model 102 by a data updater module 104E, 104F adapted to the image data type.

The answer received, m some embodiments, provides an indication of the success of a procedure. In some embodiments, the indication comprises a visualization of results by an output module 130E, based on display of a model updated by data updater 104E to show post-procedure vascular images. In some embodiments, the indication comprises an index or parameter set calculated by virtual updater 101F and/or an output module 130F for a re-imaged set of vascular images. In some embodiments, the indication comprise the comparison of anticipated index or parameter values with index or parameter values actually achieved by a procedure.

In some embodiments (FIG. 1G), there exists a question regarding disease progression, monitoring, and/or follow-up of a clinical status of a patient. For example, a stenosis which is potentially in need of future treatment, but not presently, is imaged at one or more times, with later images being imported into vascular tree model 102 by data updater 104G. In some embodiments of the invention, a progression model is created using a virtual updater 101G. In some embodiments, the progression model is based on extrapolation of a changing degree of stenosis observed between a first and second time point. In some embodiments, progression is based on extrapolation according to a standard curve based on a degree of stenosis observed at a first time point and/or other parameters such as patient vital statistics. In some embodiments, the standard curve is derived from clinical studies.

The answer received, in some embodiments, is output by output module 130G as, for example, a progression graph, one or more vascular tree models virtually updated for a predicted progression, or another static and/or inactive display of predicted disease progression. In some embodiments, follow-up is scheduled based on predicted disease progression.

It is expected that during the life of a patent maturing from this application many relevant vascular treatments will be developed and the scope of the term vascular treatment is intended to include all such new technologies a priori.

As used herein, the term "about" refers to within ±10%.

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although the invention has been described m conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of identifying vascular segments represented in common by different regions of 2-D projection images of a vasculature, comprising:
   determining a group of back-projecting rays from identified vascular segments in each of a plurality of the 2-D projection images; and
   identifying respective regions for at least a subset of the 2-D projection images that commonly-represent a same identified vascular segment based on analyzing the back-projecting rays which are indicated as intersecting each other;
   wherein the group of back-projecting rays are indicated as intersecting each other based on at least a portion of a first back-projecting ray being at a distance of at least twice a sampling interval of the 2-D projection images from a second back-projecting ray.

2. The method of claim 1, wherein the back-projecting rays are determined based on imaging configuration parameters describing conditions of image acquisition.

3. The method of claim 1, wherein the back-projecting rays are determined based on parameters describing a path between an image position in a projection plane and a position of a radiation source.

4. The method of claim 1, wherein each of the plurality of the 2-D projection images are sub-divided to generate at least two sub-images comprising a higher sampling interval than each of the 2-D projection images.

5. The method of claim 1, wherein at least two 2-D projection images commonly-represent the same identified vascular segment if both of the at least two 2-D projection images commonly-represent said same identified vascular segment with a shared 2-D projection image.

6. The method of claim 1, further comprising generating a three-dimensional vascular model comprising the identified vascular segments using the subset of the 2-D projection images that commonly-represent the identified vascular segments.

7. The method of claim 1, further comprising:
   determining vascular characteristics of the identified vascular segments from the 2-D projection images that commonly-represent the identified vascular segments; and
   calculating an index indicative of vascular function for the identified vascular segments using the determined vascular characteristics.

8. The method of claim 1, further comprising:
   determining feature metrics from the identified vascular segments in each of the plurality of the 2-D projection images; and
   verifying that the 2-D projection images commonly-represent the same identified vascular segment based on similarities between the feature metrics.

9. A vascular assessment apparatus configured to identify vascular segments represented in common by different regions of 2-D projection images of a vasculature, the apparatus comprising:
   a processor communicatively coupled to a medical imaging device; and
   a memory storing non-transitory computer-readable instructions, which when executed, cause the processor to:
      determine a group of back-projecting rays from identified vascular segments in each of a plurality of the 2-D projection images; and
      identify a respective region for at least a subset of the 2-D projection images that commonly-represent a same identified vascular segment based on analyzing the back-projecting rays which are indicated as intersecting each other;
      wherein the group of back-projecting rays are indicated as intersecting each other based on at least a portion of a first back-projecting ray being at a distance of at least twice a sampling interval of the 2-D projection images from a second back-projecting ray.

10. The apparatus of claim 9, wherein the back-projecting rays are determined based on imaging configuration parameters describing conditions of image acquisition.

11. The apparatus of claim 9, wherein the back-projecting rays are determined based on parameters describing a path between an image position in a projection plane, and a position of a radiation source.

12. The apparatus of claim 9, wherein each of the plurality of the 2-D projection images are sub-divided to generate at least two sub-images comprising a higher sampling interval than each of the 2-D projection images.

13. The apparatus of claim 9, wherein at least two 2-D projection images commonly-represent the same identified vascular segment if both of the at least two 2-D projection images commonly-represent said same identified vascular segment with a shared 2-D projection image.

14. The apparatus of claim 9, wherein the memory further stores non-transitory computer-readable instructions, which when executed, causes the processor to generate a three-dimensional vascular model comprising the identified vascular segments using the subset of the 2-D projection images that commonly-represent the identified vascular segments.

15. The apparatus of claim 9, wherein the memory further stores non-transitory computer-readable instructions, which when executed, causes the processor to:
   determine vascular characteristics of the identified vascular segments from the 2-D projection images that commonly-represent the identified vascular segments; and
   calculate an index indicative of vascular function for the identified vascular segments using the determined vascular characteristics.

16. The apparatus of claim 9, wherein the memory further stores non-transitory computer-readable instructions, which when executed, cause the processor to:
   determine feature metrics from the identified vascular segments in each of the plurality of the 2-D projection images; and verify that the 2-D projection images commonly-represent the same identified vascular segment based on similarities between the feature metrics.

17. A method of relating additional data samples to a vascular tree representation of a vasculature, the method comprising:
  generating a first record of an image region of samples projected from the vasculature, the first record having a plurality of entries, each of the plurality of entries being individually mapped to said vascular tree representation;
  generating a second record of the image region of samples projected from said vasculature, the second record comprising differences compared to the first record; and
  updating automatically the first record to reflect the differences, the differences being based on 3-D projected epipolar mapping between samples of the first record and the second record.

18. The method of claim 17, wherein the update of the first record is inserted into the vascular tree representation according to said individual mapping.

19. The method of claim 18, wherein the update of the first record is inserted into the vascular tree representation in place of the first record.

20. The method of claim 17, wherein the update of the first record comprises a partial update of the first record.

* * * * *